(12) United States Patent
Shaunak et al.

(10) Patent No.: US 9,453,040 B2
(45) Date of Patent: Sep. 27, 2016

(54) GLYCODENDRIMERS OF POLYPROPYLETHERIMINE

(75) Inventors: Sunil Shaunak, Greater London (GB); Ian Alfred Teo, Greater London (GB)

(73) Assignee: IMPERIAL INNOVATIONS LIMITED, London, Greater London (GB)

( * ) Notice: Subject to any disclaimer, the term of this patent is extended or adjusted under 35 U.S.C. 154(b) by 481 days.

(21) Appl. No.: 13/818,580

(22) PCT Filed: Aug. 22, 2011

(86) PCT No.: PCT/GB2011/051577
§ 371 (c)(1),
(2), (4) Date: May 6, 2013

(87) PCT Pub. No.: WO2012/025744
PCT Pub. Date: Mar. 1, 2012

(65) Prior Publication Data
US 2015/0126468 A1 May 7, 2015

Related U.S. Application Data

(60) Provisional application No. 61/344,571, filed on Aug. 24, 2010.

(30) Foreign Application Priority Data

Oct. 7, 2010 (GB) .................................... 1016892.0
Jun. 2, 2011 (GB) .................................... 1109292.1

(51) Int. Cl.
| | | |
|---|---|---|
| *A01N 43/04* | (2006.01) |
| *A61K 31/70* | (2006.01) |
| *A61K 31/715* | (2006.01) |
| *C08B 37/00* | (2006.01) |
| *C07G 3/00* | (2006.01) |
| *C07G 11/00* | (2006.01) |
| *C07H 15/00* | (2006.01) |
| *C07H 17/00* | (2006.01) |
| *C07H 15/26* | (2006.01) |
| *A61K 47/48* | (2006.01) |
| *C07H 5/06* | (2006.01) |
| *C07H 11/00* | (2006.01) |
| *C07H 13/04* | (2006.01) |
| *C08G 73/02* | (2006.01) |
| *C07H 15/12* | (2006.01) |
| *C08G 83/00* | (2006.01) |

(52) U.S. Cl.
CPC ......... *C07H 15/26* (2013.01); *A61K 47/48192* (2013.01); *A61K 47/48207* (2013.01); *C07H 5/06* (2013.01); *C07H 11/00* (2013.01); *C07H 13/04* (2013.01); *C07H 15/12* (2013.01); *C08G 73/02* (2013.01); *C08G 73/024* (2013.01); *C08G 73/028* (2013.01); *C08G 83/003* (2013.01)

(58) Field of Classification Search
CPC ................. A61K 47/48192; A61K 47/48207; C07H 5/06; C07H 11/00; C08G 73/024; C08G 73/028
USPC ....................................... 514/53, 61; 536/53
See application file for complete search history.

(56) References Cited

U.S. PATENT DOCUMENTS

2005/0214247 A1 * 9/2005 Shaunak et al. ........... 424/78.27

FOREIGN PATENT DOCUMENTS

WO WO 2012/025745 A1 3/2012

OTHER PUBLICATIONS

Jain et al., "Poly propyl ether imine (PETIM) dendrimer: A novel non-toxic dendrimer for sustained drug delivery," European Journal of Medicinal Chemistry, vol. 45, 2010, pp. 4997-5005.
Pending Claims 1-35 filed Feb. 22, 2013, for U.S. Appl. No. 13/818,557, 4 pages.
Teo et al., "Preventing acute gut wall damage in infectious diarrhoeas with glycosylated dendrimers," EMBO Mol. Med. 4, 866-81, 2012, including Supplementary Data (38 pages).

* cited by examiner

*Primary Examiner* — Scarlett Goon
(74) *Attorney, Agent, or Firm* — Banner & Witcoff, Ltd.

(57) ABSTRACT

A glycodendrimer comprising: a) a non-toxic dendrimer polypropyletherimine core supporting on average in the range of 9 to 64 terminal carboxylic acid groups, and b) conjugated to said core in the range of 2 to 8 amino sugars or a sulphate amino sugar selected from the group consisting of glucosamine, N-acetyl glucosamine, mannosamine, N-acetylmannosamine, galactosamine, a sulphate of any one of the same and a combination thereof, wherein each sugar is linked directly through a zero length amide bond with a residue of a terminal carboxylic acid group. The invention also extends to defined populations comprising said glycodendrimer molecules, pharmaceutical compositions comprising said molecules or populations, process for preparing the molecules and formulations, and therapeutic uses of the molecules, populations and compositions.

12 Claims, 46 Drawing Sheets

Figure 1:
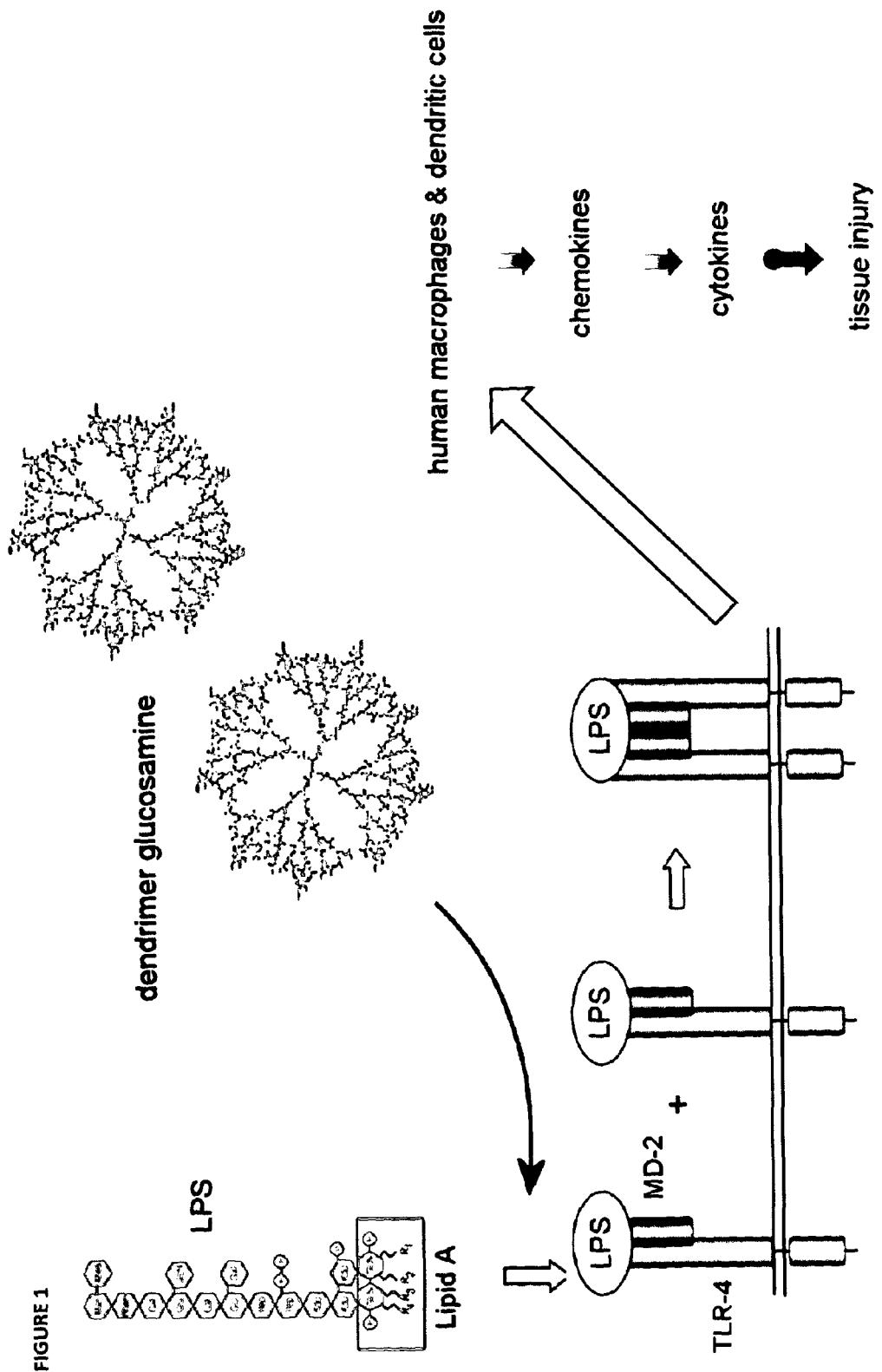

Figure 3
Pro-inflammatory cytokines
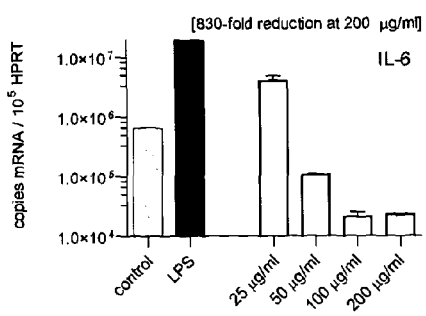
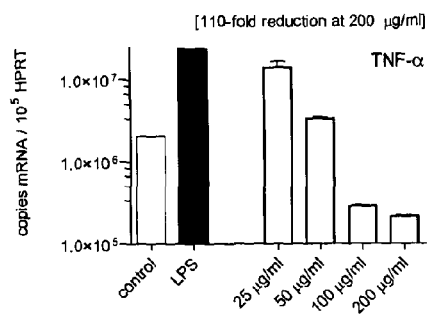
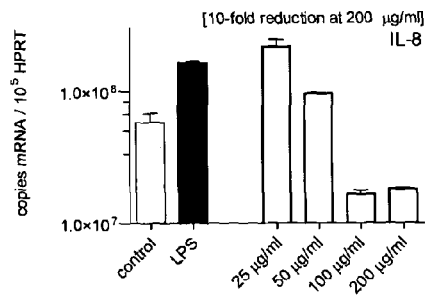
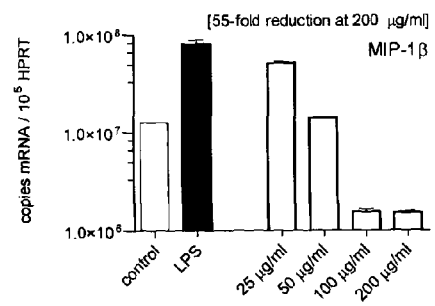
Anti-inflammatory cytokines - no significant changes
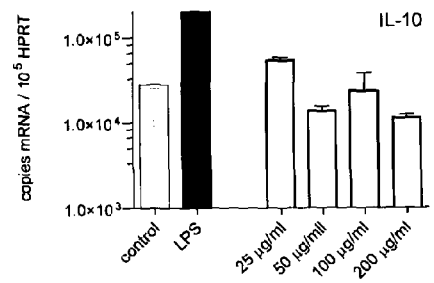
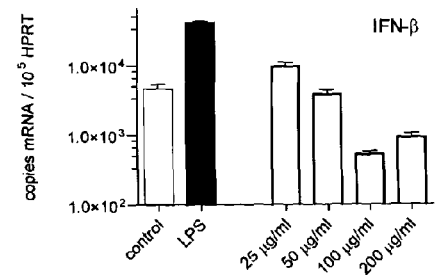

Figure 4
Pro-inflammatory cytokines
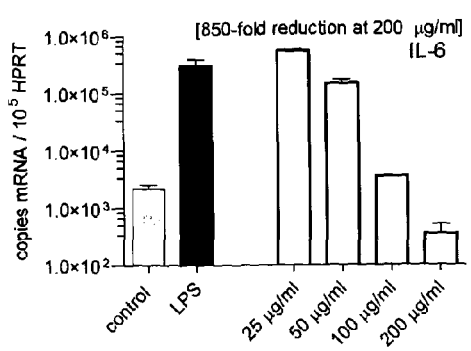
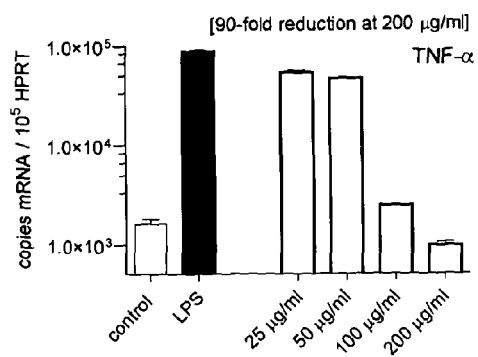
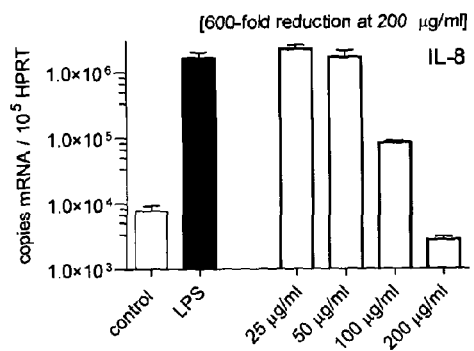
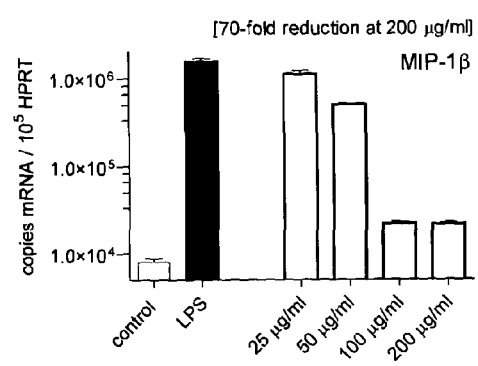
Anti-inflammatory cytokines – no significant changes
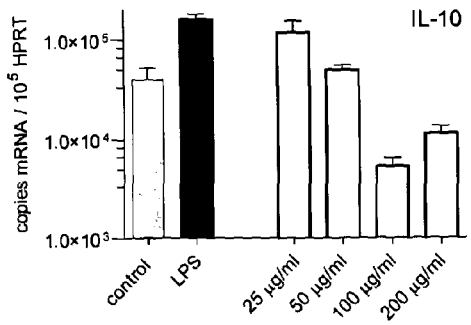
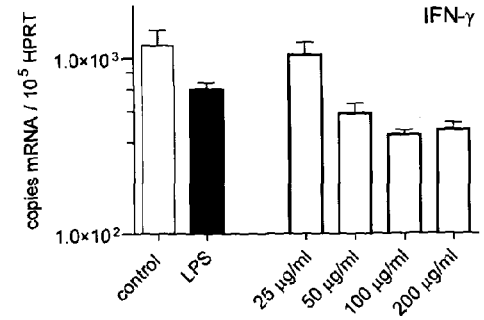

Figure 5
Pro-inflammatory cytokines
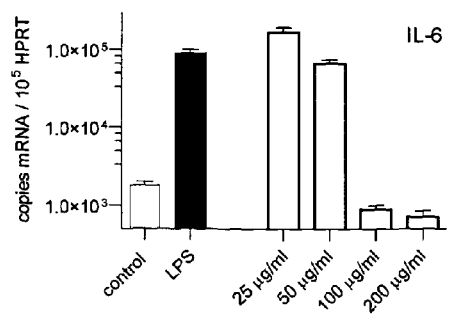
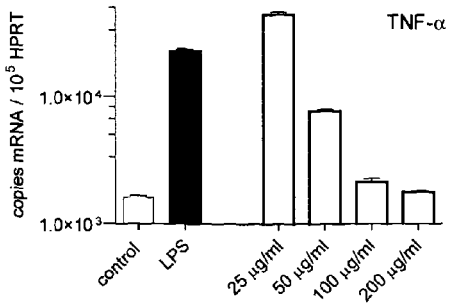
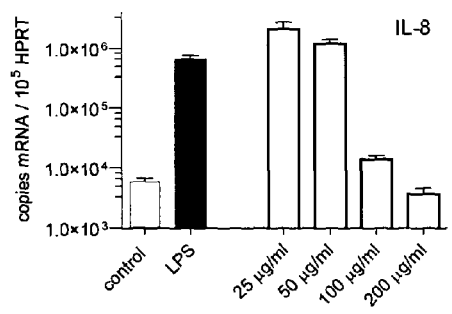
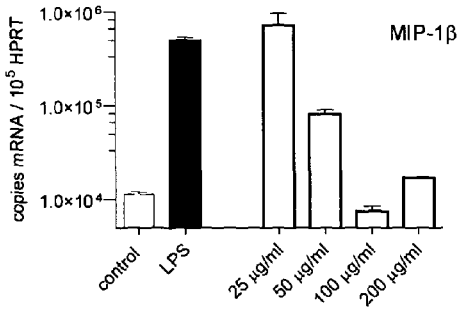
Anti-inflammatory cytokines - no significant changes
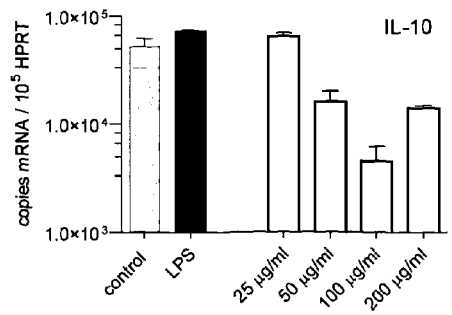
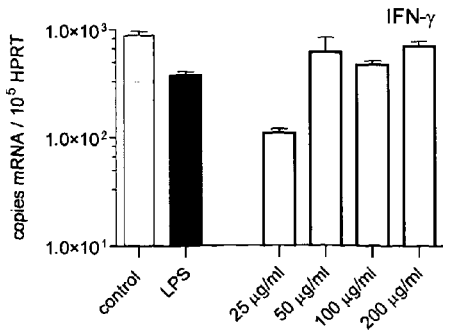

FIGURE 6
A
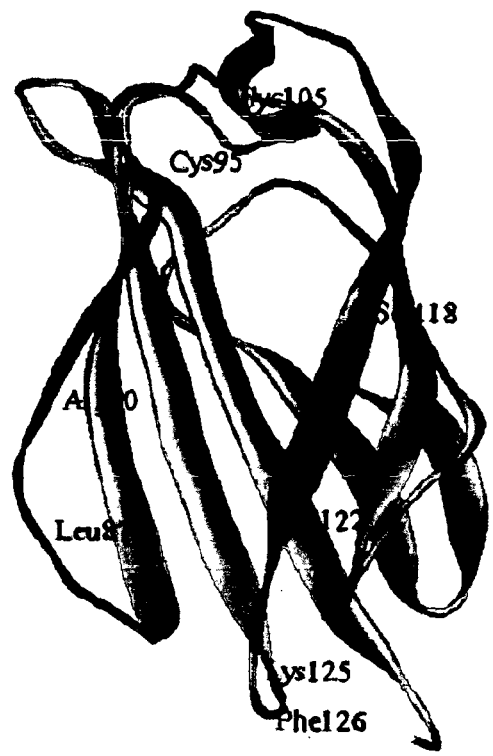
B
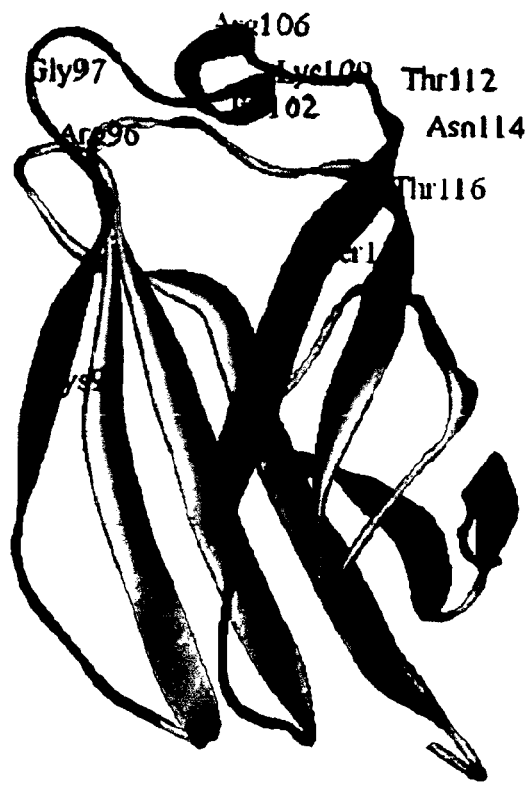

FIGURE 7
A
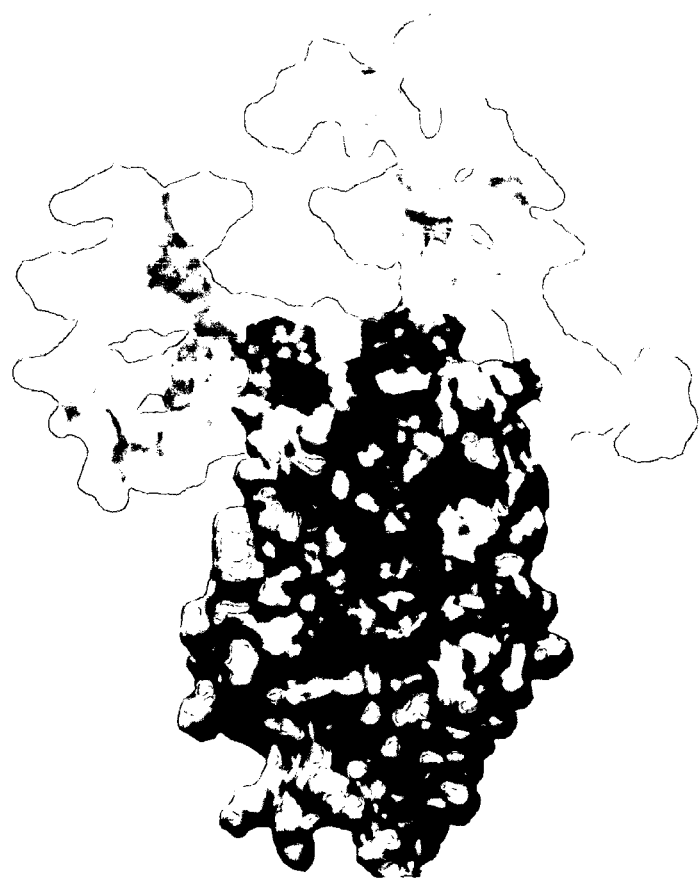
B

Figure 8
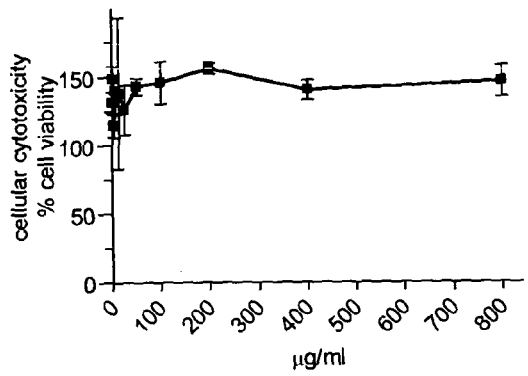
Pro-inflammatory cytokines - no significant changes
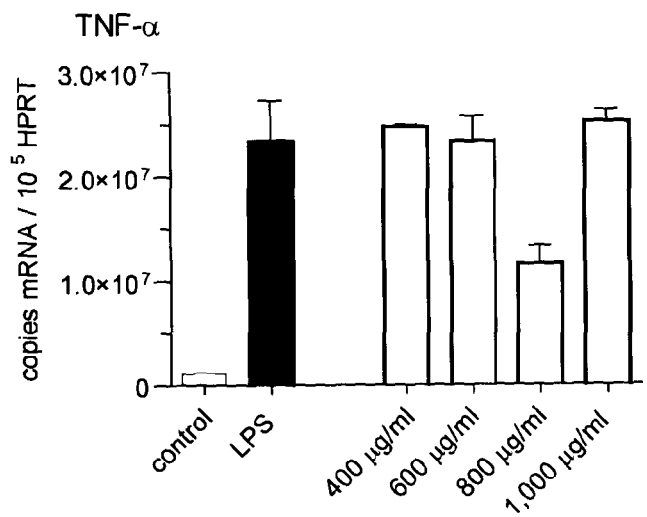
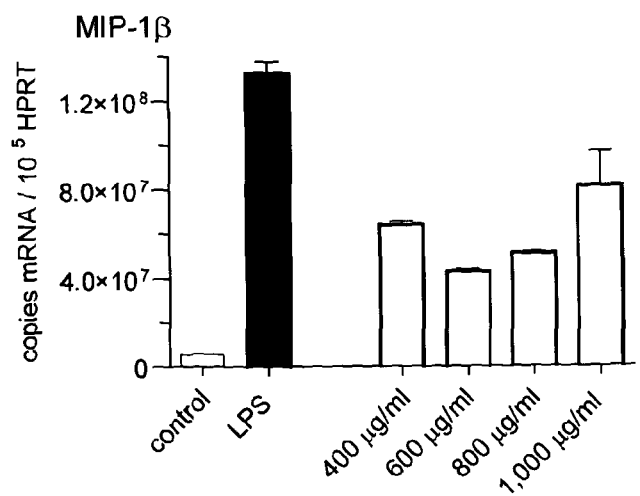

Figure 9
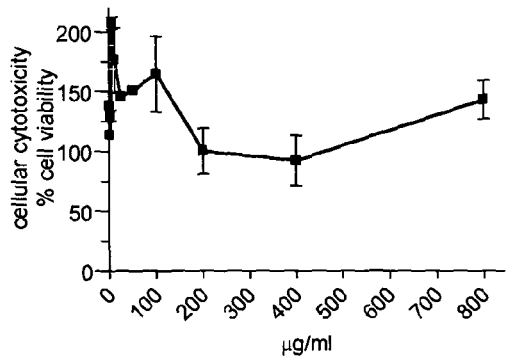
Pro-inflammatory cytokines - no significant changes
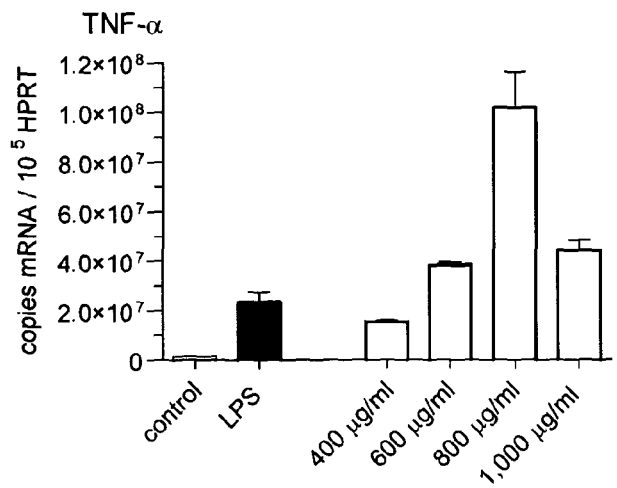
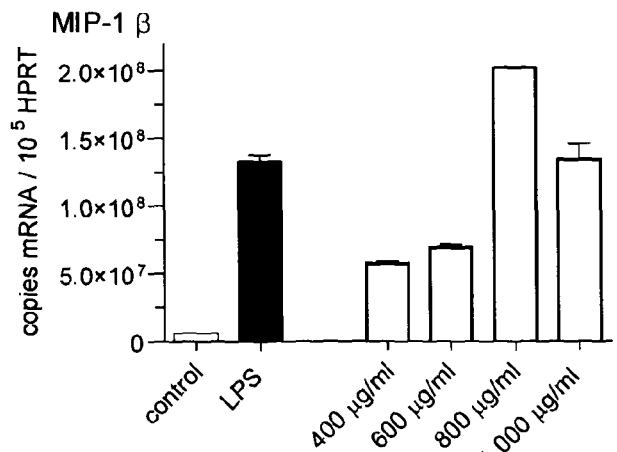

Figure 10
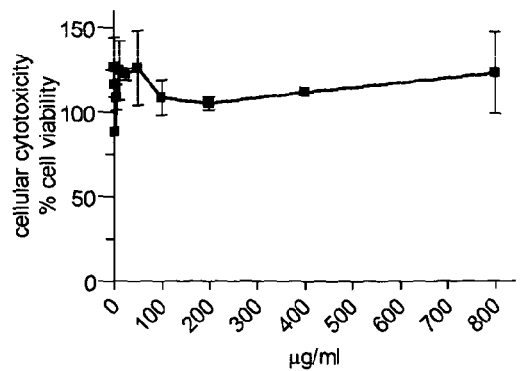
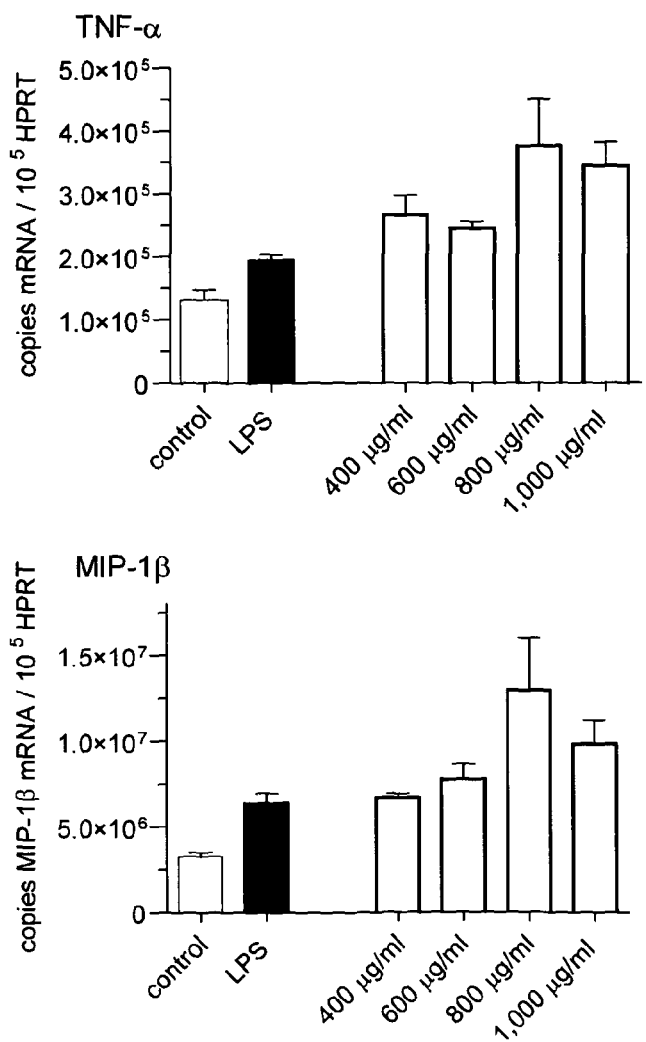

Figure 11
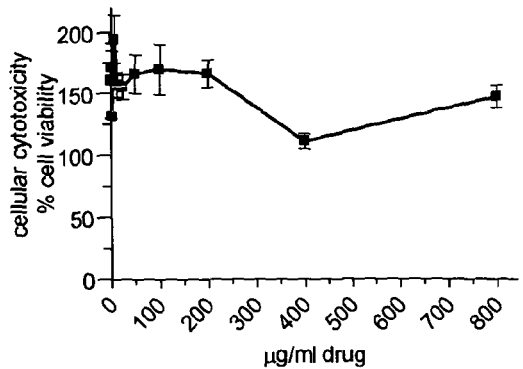
Pro-inflammatory cytokines - no significant changes
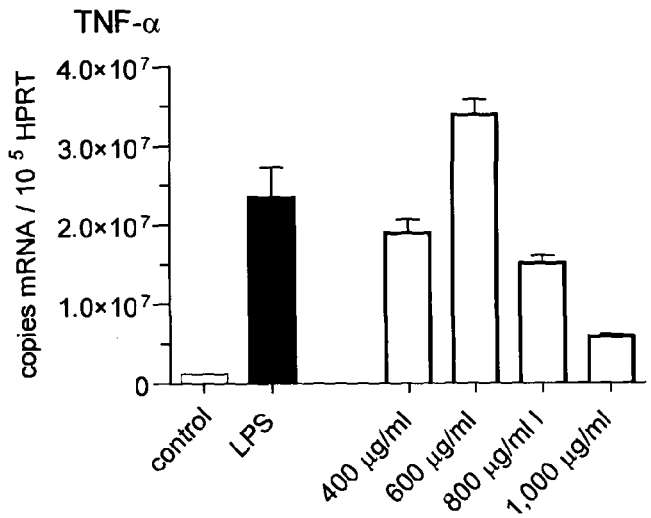
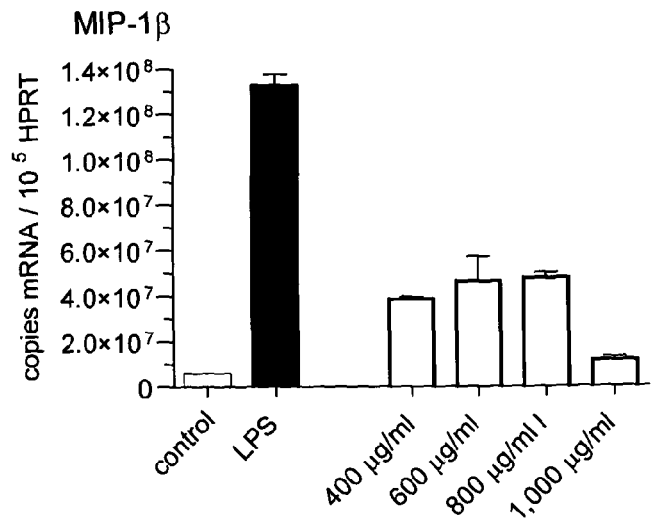

Figure 12
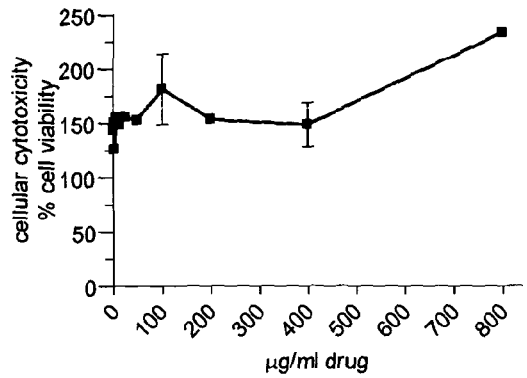
Pro-inflammatory cytokines - no significant changes
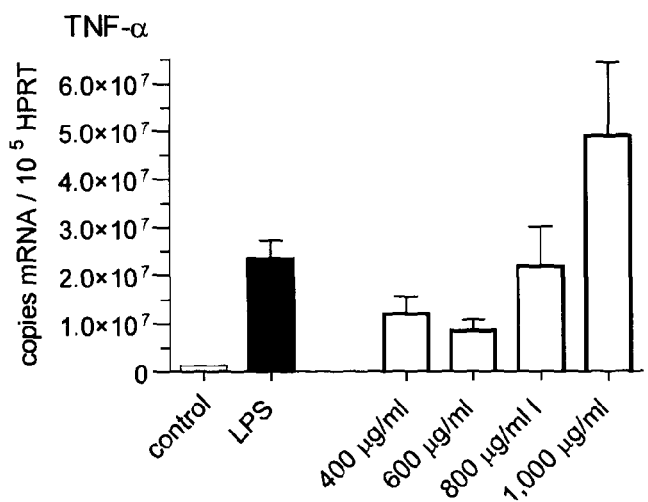
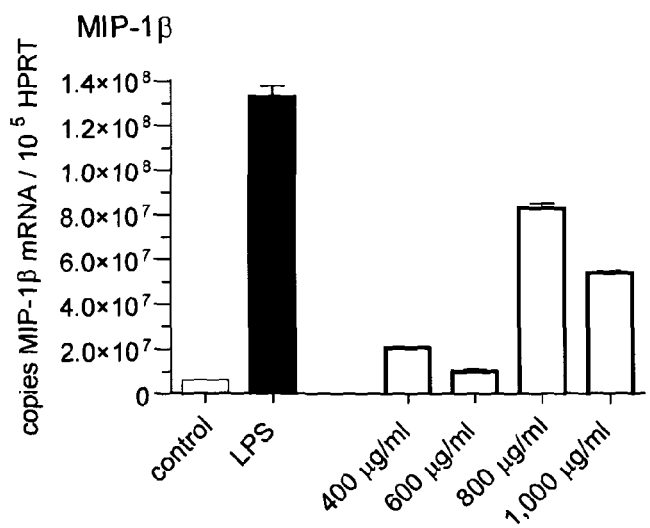

Figure 13
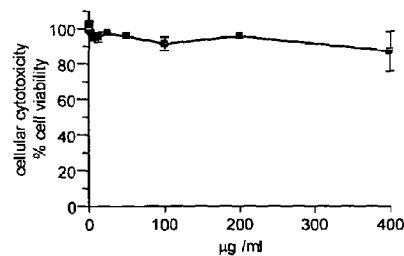
Pro-inflammatory cytokines - no significant changes
IL-6
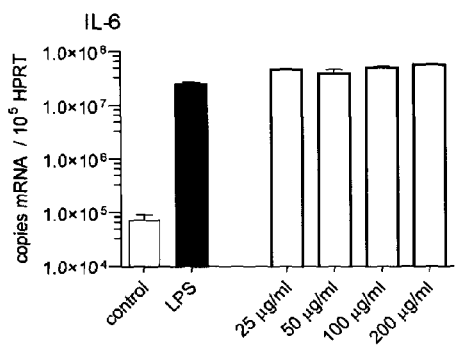
TNF-α
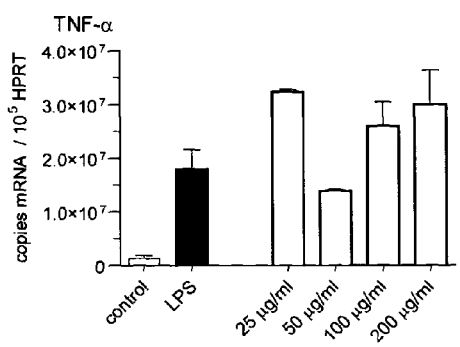
IL-8
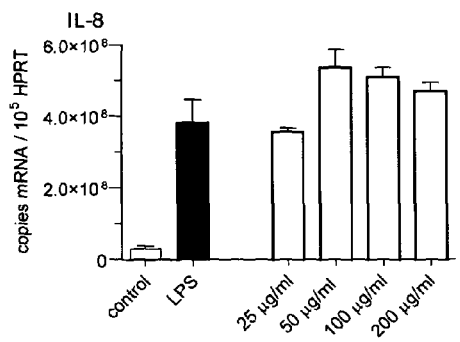
MIP-1β
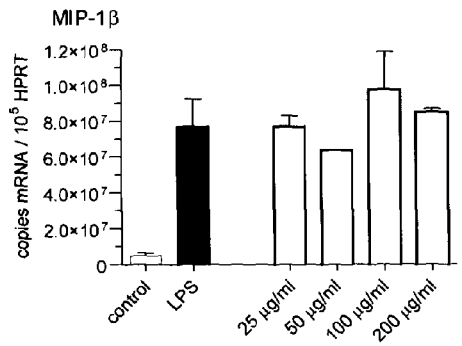

Figure 14
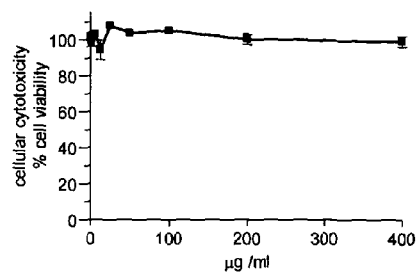
Pro-inflammatory cytokines – no significant changes
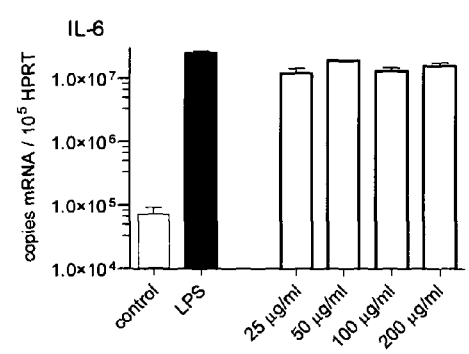
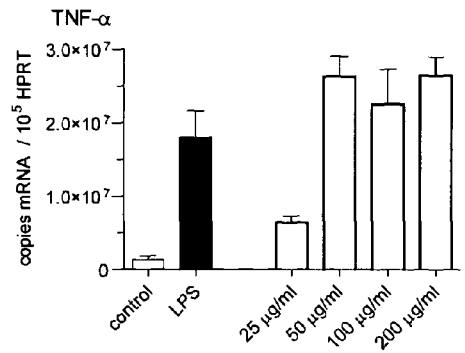
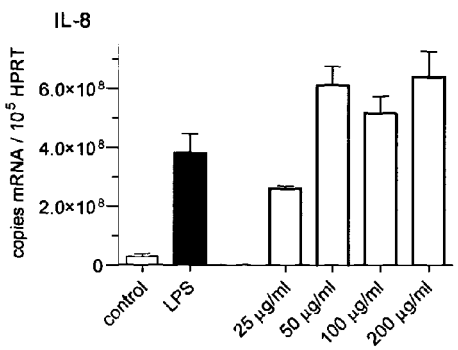
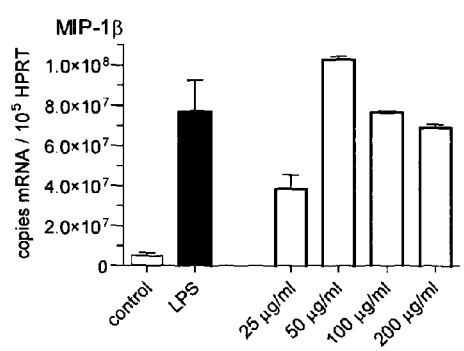

Figure 15
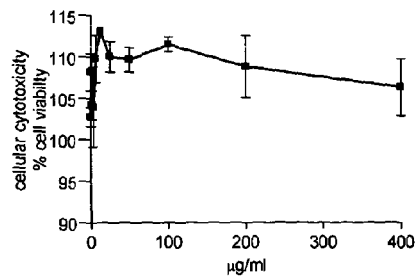
Pro-inflammatory cytokines - no significant changes
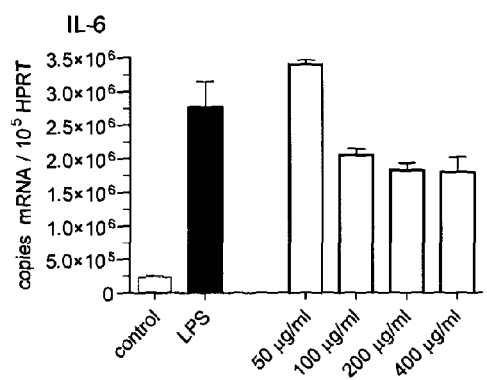
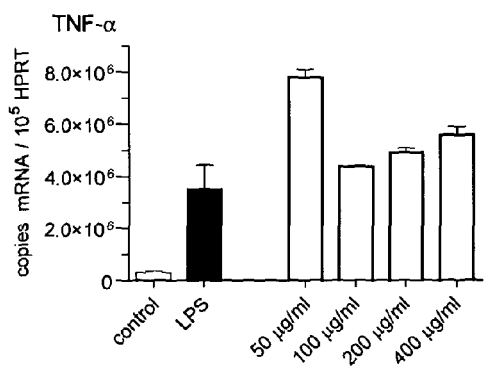
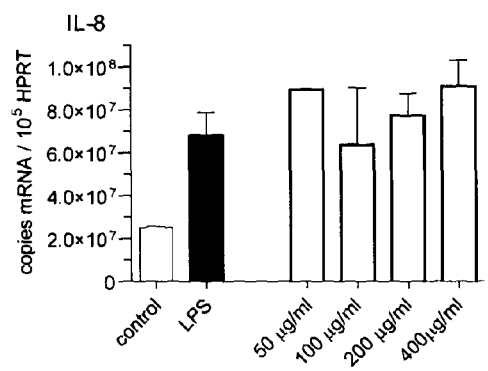
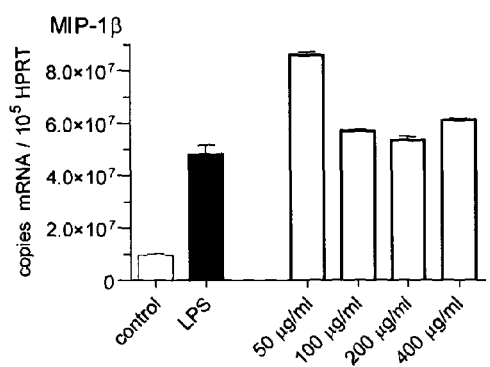

Figure 16
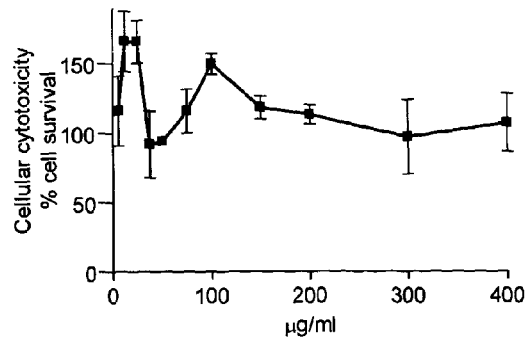
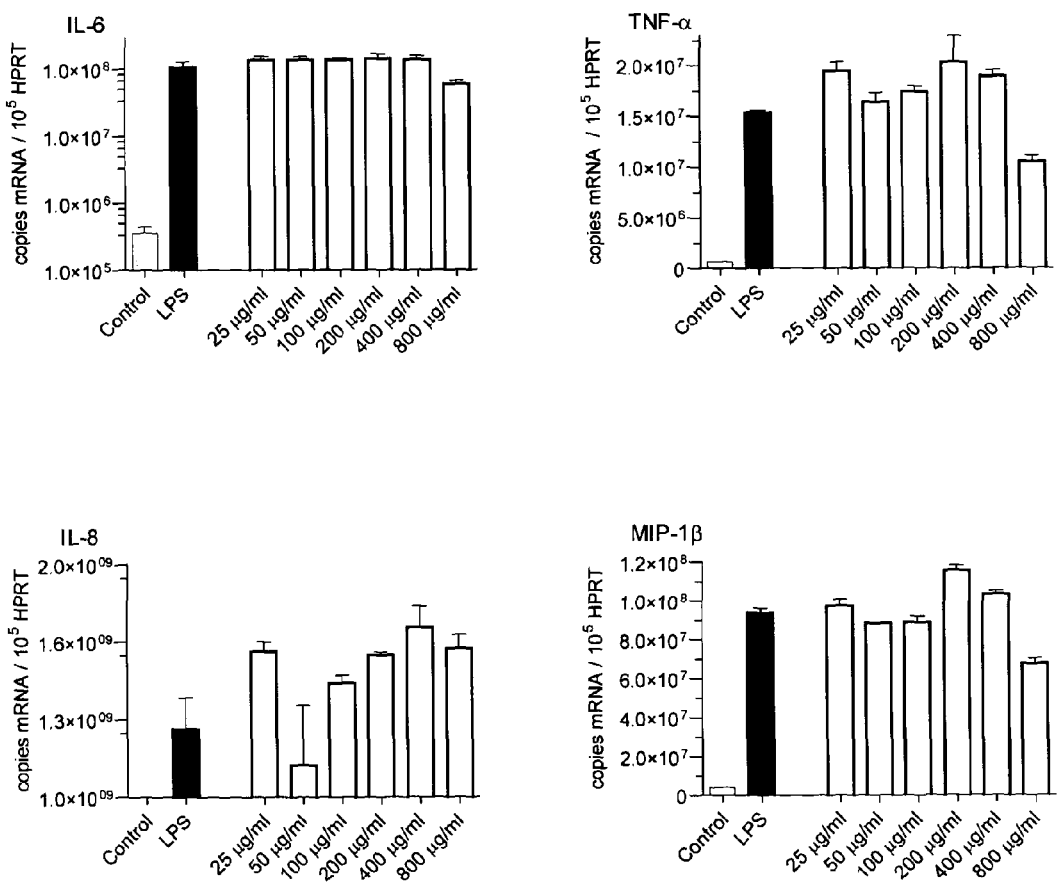

Figure 17
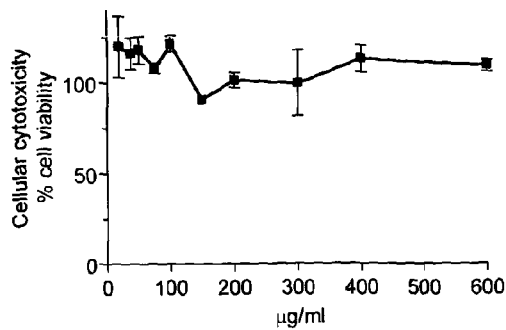
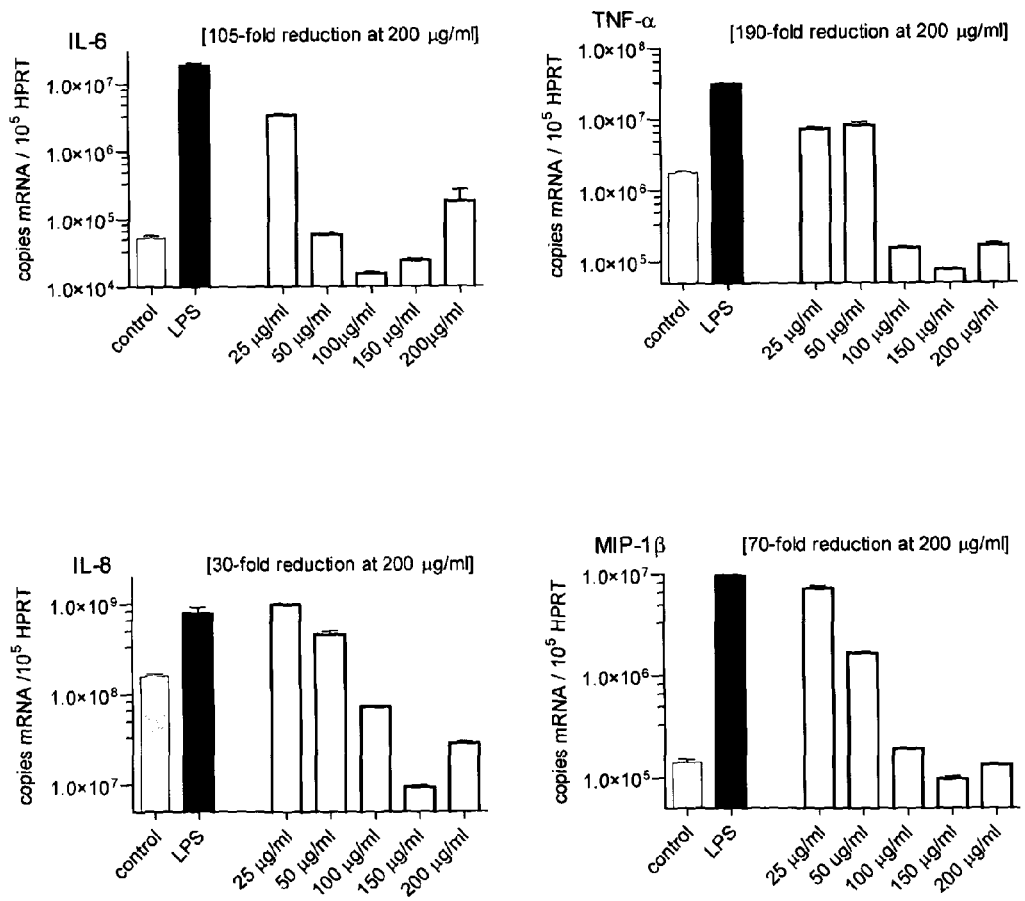

Figure 34
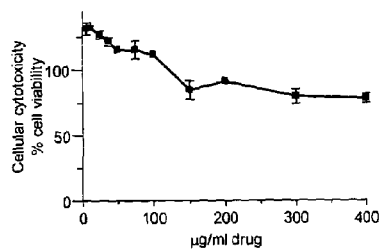
Pro-inflammatory cytokines
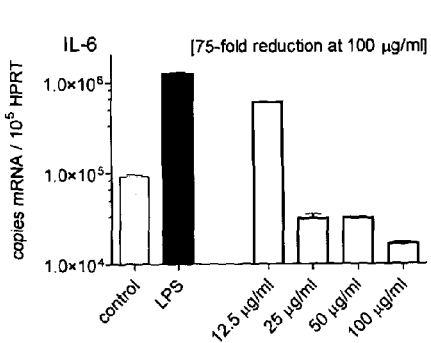
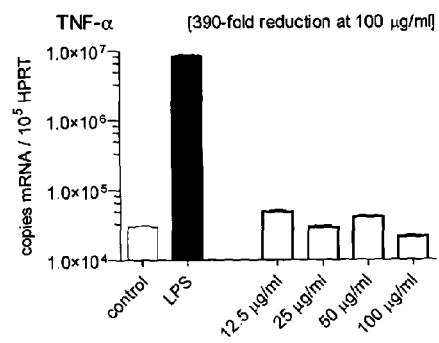
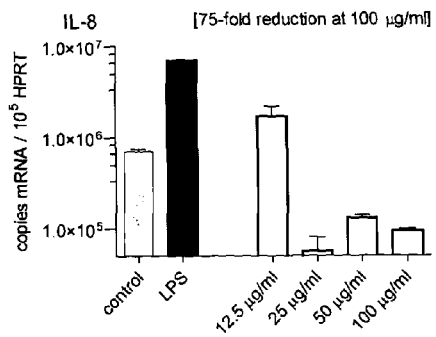
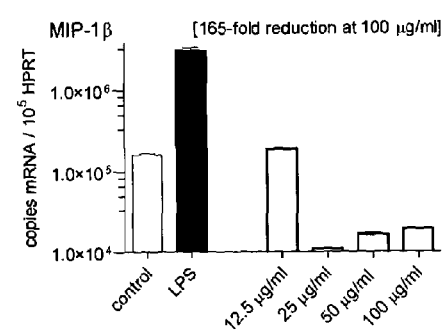

Figure 35
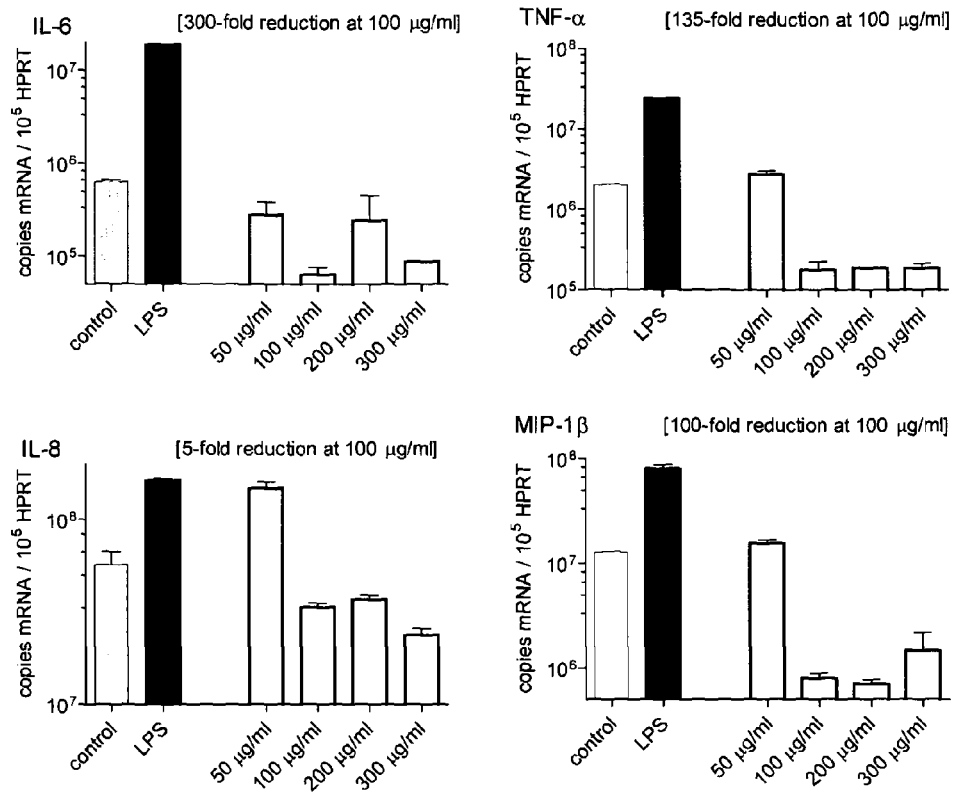
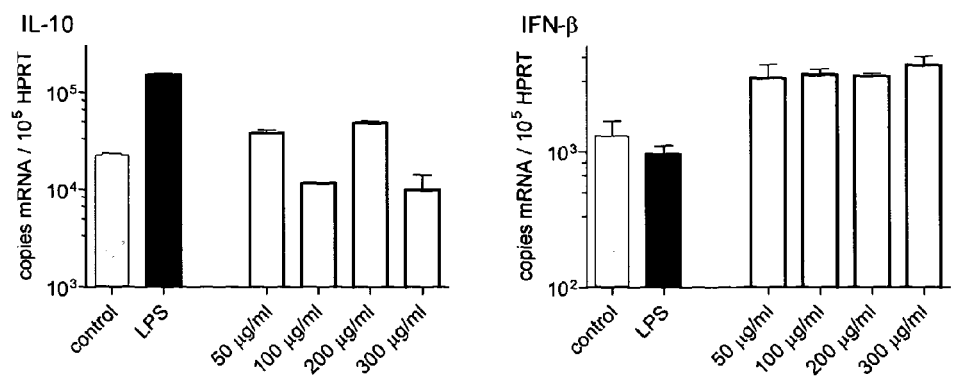

Figure 36
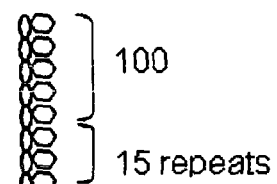 M90
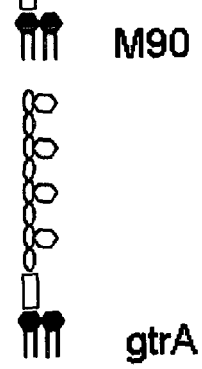 gtrA
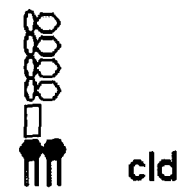 cld
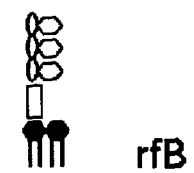 rfB
 waaL Figure 39
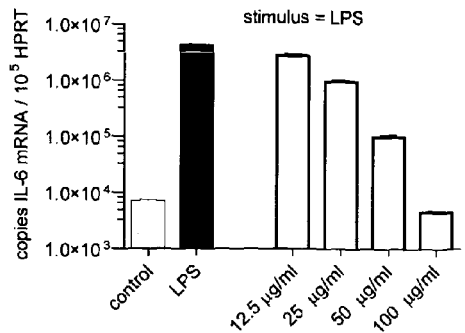
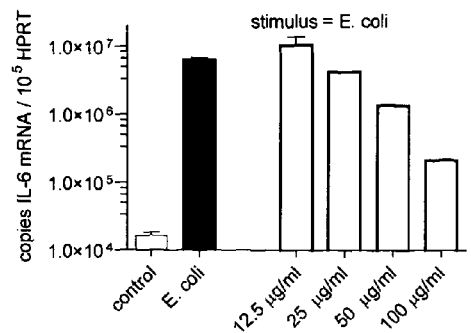
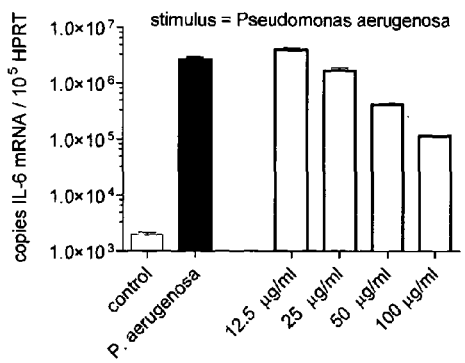
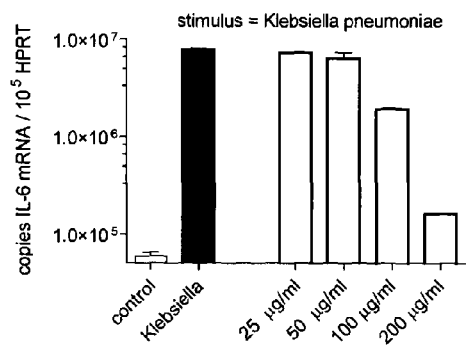
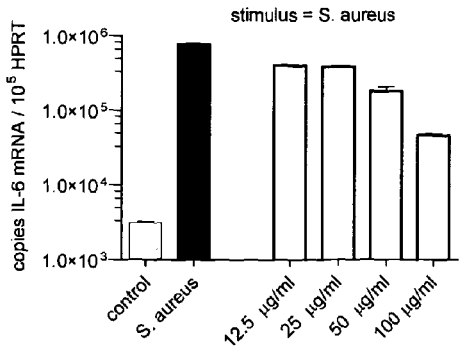
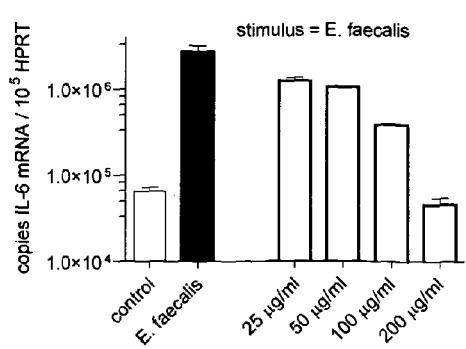

Figure 42    1H NMR spectrum of polypropyletherimine-(COOH)16.14HCl core.
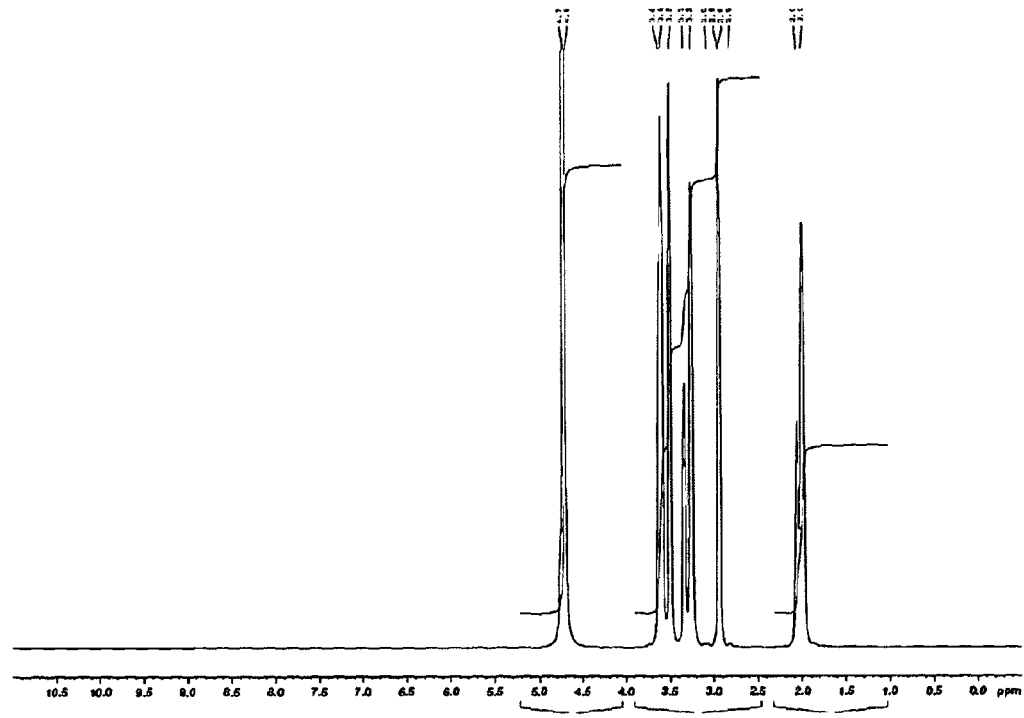
Figure 43    1H COSY NMR spectrum of polypropyletherimine-(COOH)16.14HCl core
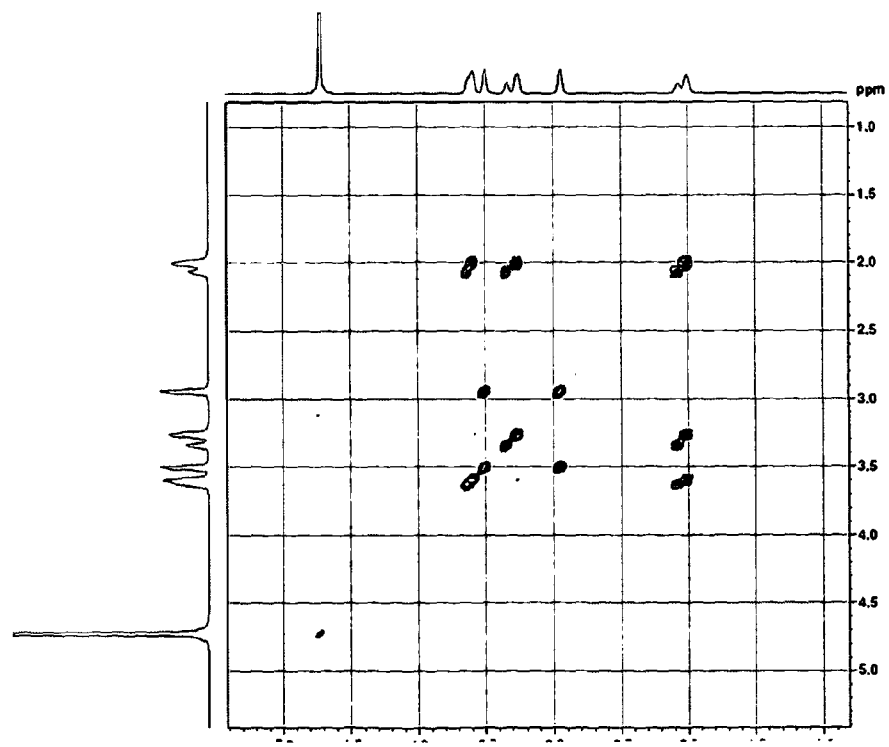

Figure 44    13C NMR spectrum of polypropyletherimine-(COOH)16.14HCl core
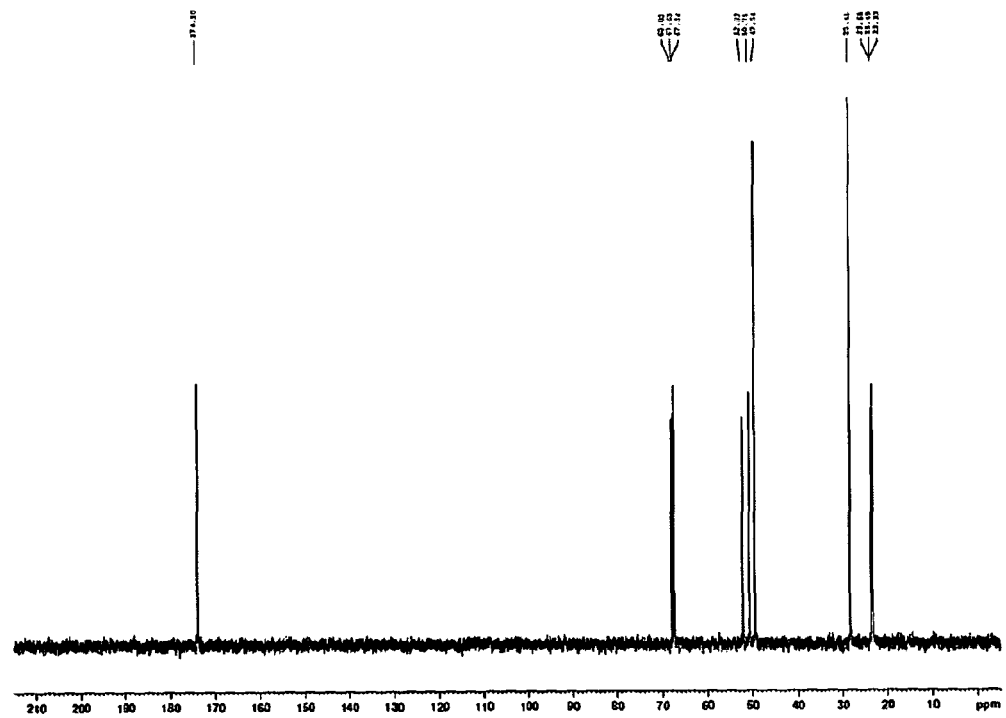
Figure 45    DEPT -135 13C NMR spectrum of polypropyletherimine-(COOH)16.14HCl core
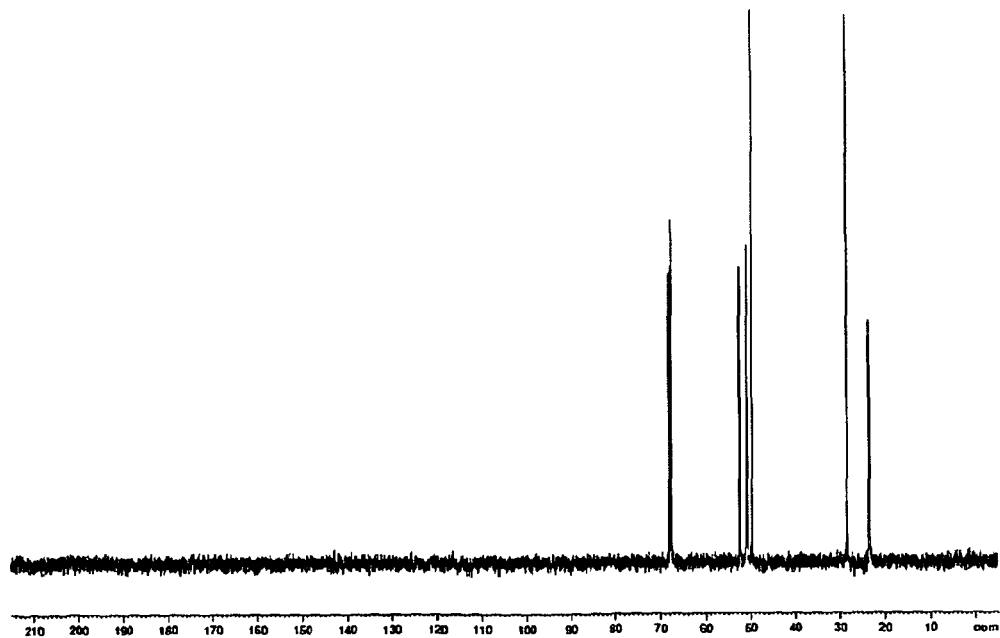

Figure 46
Identity:-
MALDI-MS of polypropyletherimine-(COOH)$_{16}$.14HCl core.
Acquired using DHB matrix in MeCN:H2O. 1:1.
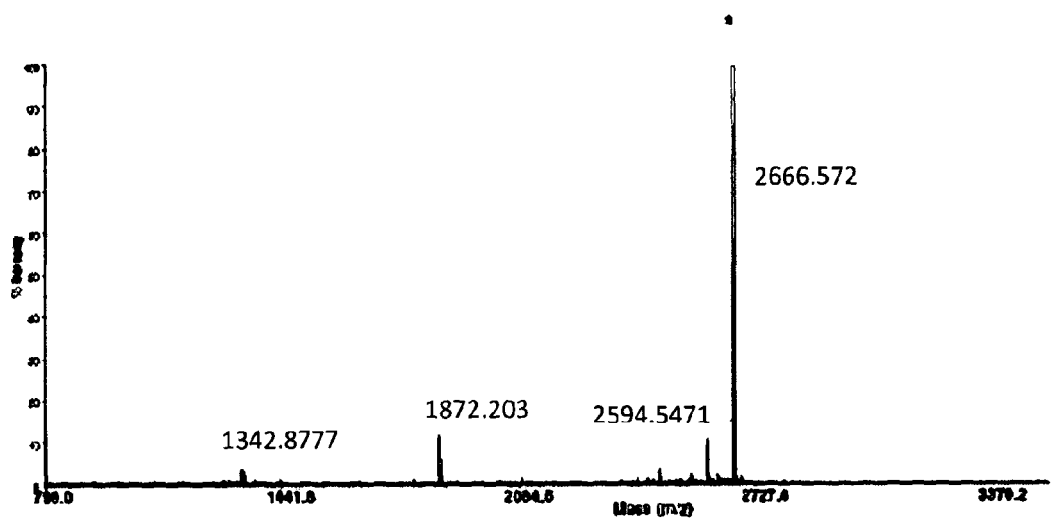
Schematic of the chemical structure of polypropyletherimine-(COOH)$_{16}$.14HCl core.
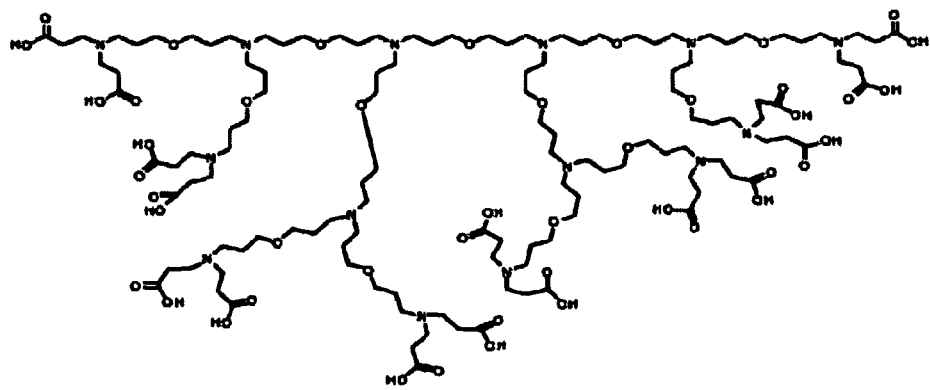
Chemical formula $C_{126}H_{236}N_{14}O_{45}$
Exact Mass 2665.6609
Molecular weight 2667.2888

Purity:-
Preparative HPLC of polypropyletherimine-(COOH)₁₆.14HCl core at 97% purity.

Figure 49a
Polypropyletherimine-(COOH)₁₄-(glucosamine)₂
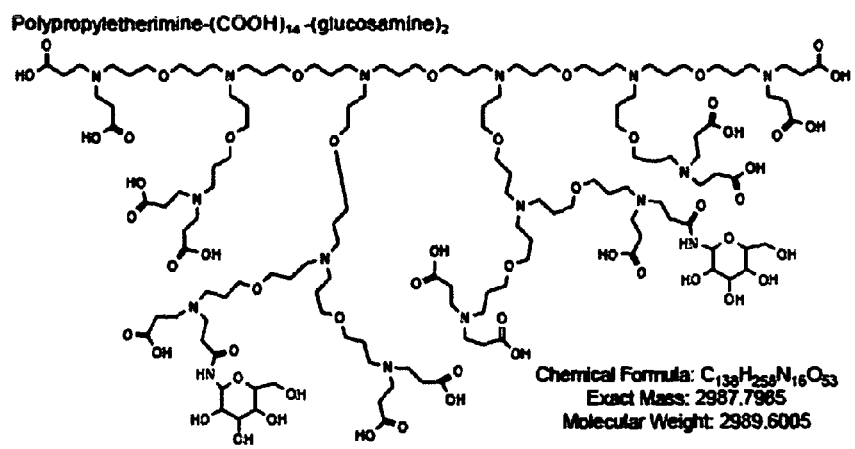
Chemical Formula: C₁₃₉H₂₅₈N₁₆O₅₃
Exact Mass: 2987.7985
Molecular Weight: 2989.6005
Identity:-
H-NMR of dendrimer-glucosamine
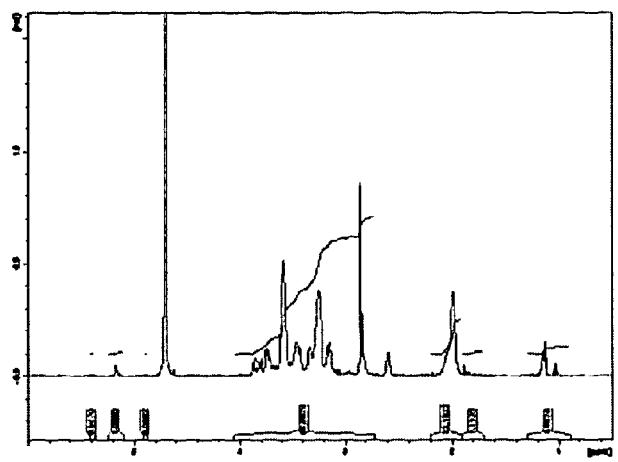
Figure 49b
Identity:-
¹³C NMR spectrum of polypropyletherimine dendrimer-glucosamine.
D₂O at 303K

Purity:-
Reverse phase HPLC/UV detection of polypropyletherimine dendrimer-glucosamine.

Cytotoxicity in Primary Human Monocytes

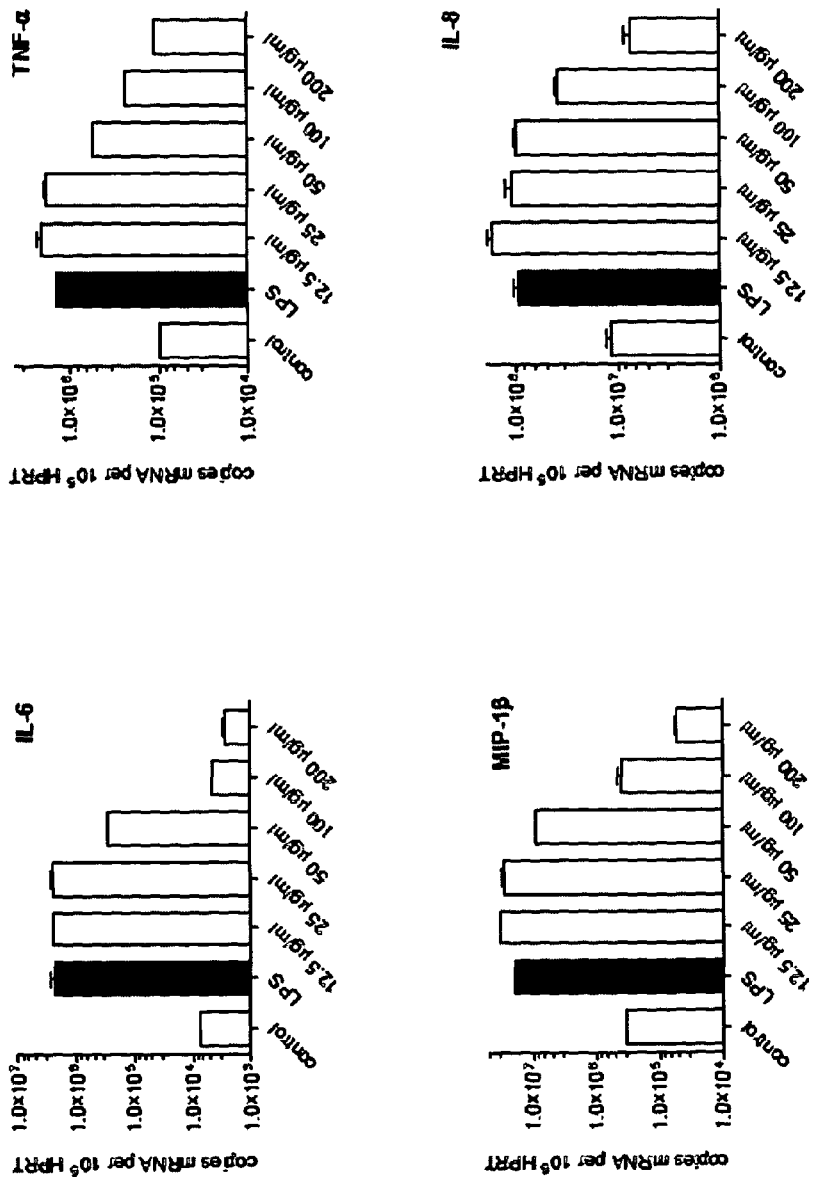
Figure 52  Polypropyletherimine-Glucoseamine Tested Using Human Monocytes and Shigella LPS

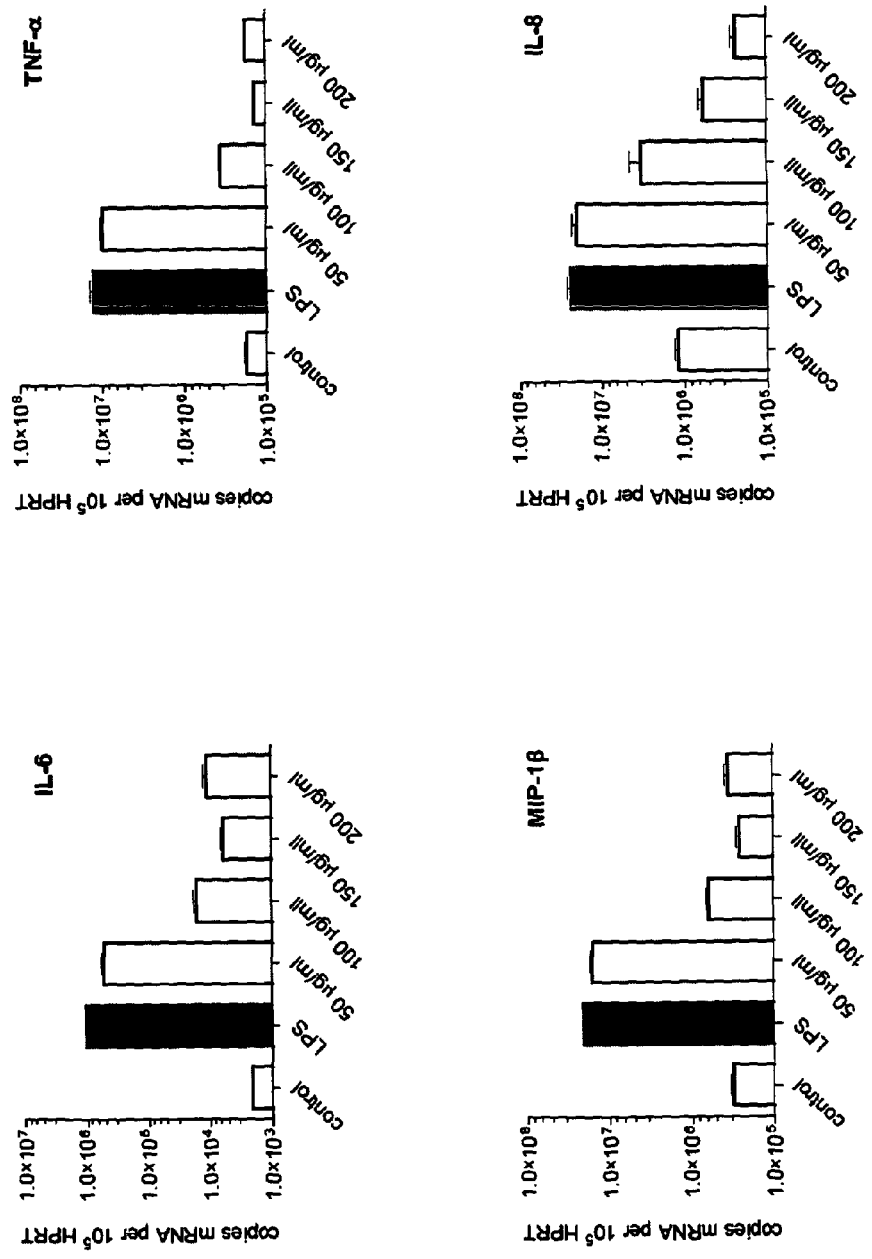
Figure 53  Polypropyletherimine-Glucoseamine Tested Using Human Monocytes and infectious E. coli bacteria

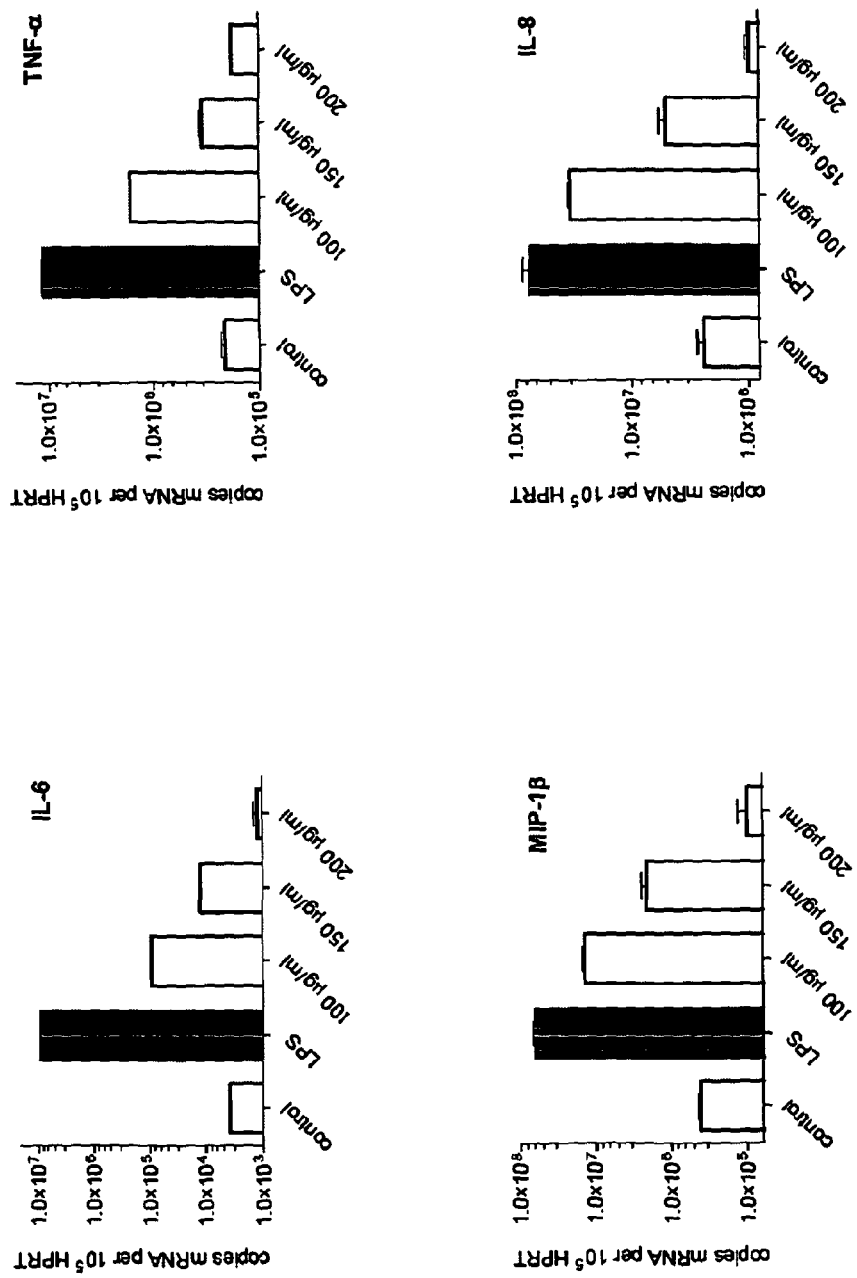
Figure 54 Polypropyletherimine-Glucoseamine Stored at 37°C and 100% Humidity in a Sealed Vial (under moisture free argon) Followed by Testing using Human Monocytes and Salmonella LPS Figure 55    Polypropyletherimine-Glucoseamine does not have Antibacterial Properties
(a) Growth of E.coli in the presence of polypropyletherimine-glucosamine
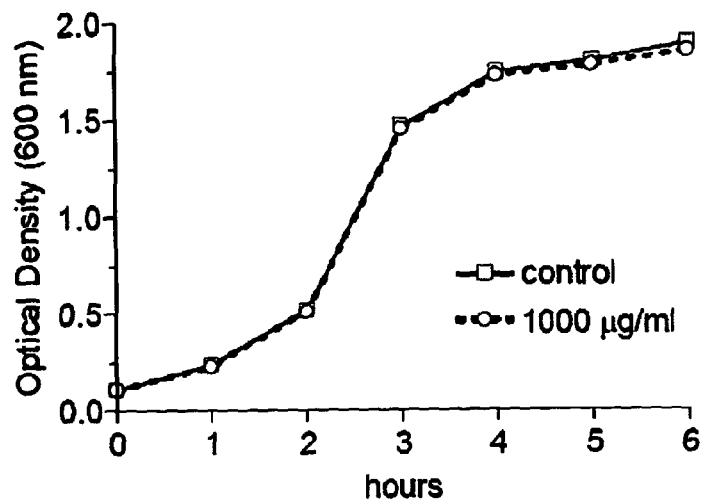
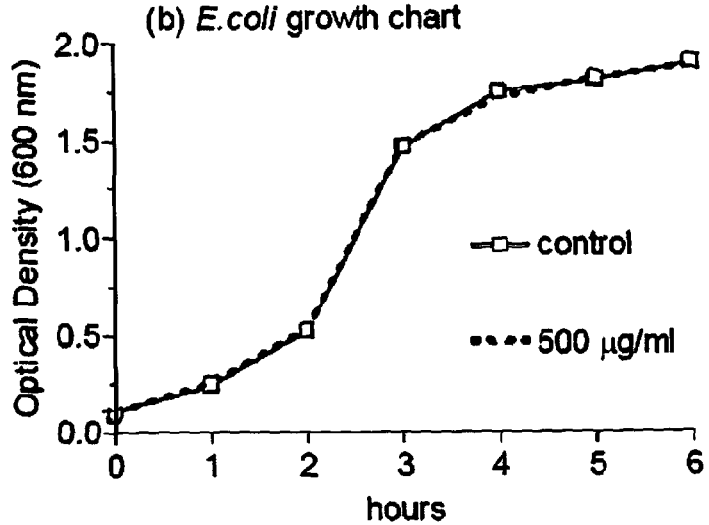

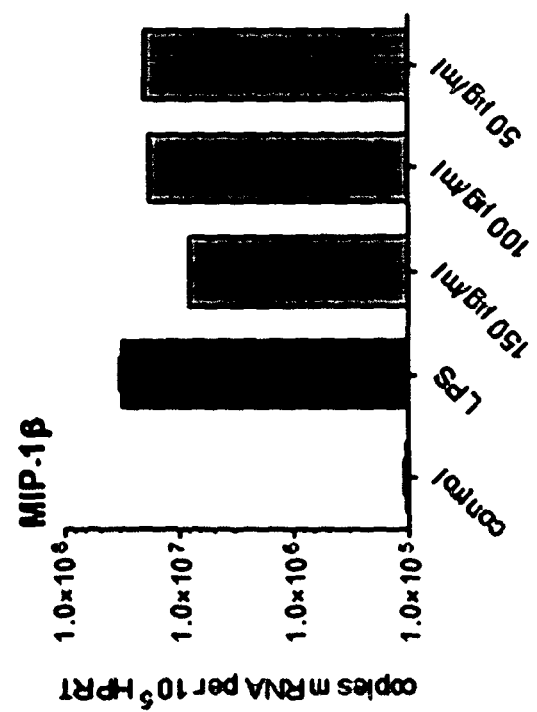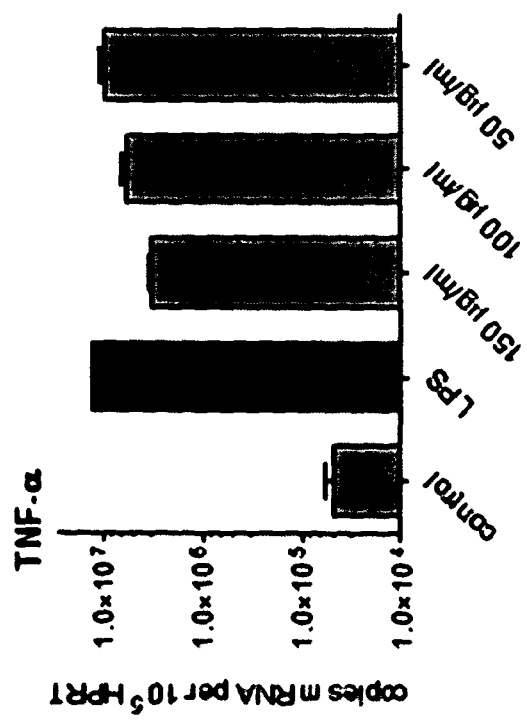
FIGURE 56

GLYCODENDRIMERS OF POLYPROPYLETHERIMINE

The present application is a national stage application of PCT/GB2011/051577 filed 22 Aug. 2011, which claims priority from U.S. provisional application 61/344,571 filed 24 Aug. 2010, GB application number 1016892.0 filed on 7 Oct. 2010, and GB application number 1109292.1 filed 2 Jun. 2011, each of which is incorporated herein by reference in its entirety.

The present disclosure relates to glycodendrimers containing a polypropyletherimine core, pharmaceutical formulations comprising same, use of each thereof in treatment, particularly in the treatment of conditions mediated by pro-inflammatory cytokines, such as Interleukin-6 and Interleukin-8. The disclosure further relates to processes for the production of the glycodendrimers, and use of polypropyletherimine cores for preparation of said glycodendrimers.

STATEMENT AS TO US GOVERNMENT SPONSORED RESEARCH

This invention was made, in part, with US Government funds from the National Institutes of Health. The US Government has certain rights in the invention.

BACKGROUND

In 2009, Park et al defined the structural basis of the recognition of LPS by TLR4-MD2 (Park B S, Song D H, Kim H M, Choi B S, Lee H, Lee J O. The structural basis of lipopolysaccharide recognition by the TLR4-MD-2 complex. Nature 2009; 458: 1191-1195; Viriyakosol S, Tobias P S, Kitchens R L, Kirkland T N. MD2 binds to bacterial lipopolysaccharide. J. Biological Chemistry 2001; 276(41): 38,044-38,051).

In brief, MD2 has a hydrophobic pocket that is lined by a charged, hydrophilic entrance. Lipid A (which consists of two phosphorylated glucosamine molecules linked together via an ester bond) binds to the entrance of this pocket. Its lipid chains then enter MD2's hydrophobic pocket. The TLR4-MD2-LPS complex undergoes a conformational change and TLR4 dimerizes. Intracellular signalling follows.

The importance of the saccharide portions of LPS and of electrostatic interactions between LPS and MD2 have recently been reinforced (Meng J et al, MD2 residues TYR 42, ARG 69, ASP 122 and LEU 125 provide species specificity for Lipid IVA. J Biol Chem. DOI: M110.134668; Meng J, Lien E, Golenbock D T. MD2 mediated ionic interactions between Lipid A and TLR4 are essential for receptor activation. J Biol Chem. 2009; 285: 8695-8702).

The most relevant residue is thought to be Tyr102, followed by Lys91, Arg96, Arg106, Asn114 and Ser118. These residues and/or residues in their very close proximity had already been identified as having an important role in the recognition of LPS by MD2 (Park B S, Song D H, Kim H M, Choi B S, Lee H, Lee J O. The structural basis of lipopolysaccharide recognition by the TLR4-MD2 complex. Nature 2009; 458: 1191-1195; Meng J et al, MD2 residues TYR 42, ARG 69, ASP 122 and LEU 125 provide species specificity for Lipid IVA. J Biol Chem. DOI: M110.134668; Meng J, Lien E, Golenbock D T. MD2 mediated ionic interactions between Lipid A & TLR4 are essential for receptor activation. J Biol Chem. 2009; 285: 8695-2).

Bacterial infections and surgical tissue injury trigger the same cell surface receptor-ligand interactions that are based upon TLR4 immuno-modulation. This does not involve a single receptor-ligand interaction. Rather, these pro-inflammatory cytokine responses are mediated by polyvalent receptor-ligand interactions between bacterially derived lipopolysaccharide (LPS) and/or surgically derived hyaluronan fragments and the cell surface TLR4 receptor (Atala A, Irvine D J, Moses M, Shaunak S. Wound healing versus regeneration: Role of the tissue environment in regenerative medicine. MRS Bulletin August 2010; 35: 597-606). The binding affinity of these ligands for this receptor increases exponentially as the number of receptor-ligand interactions increases. Therefore, it is desirable to adapt the concept of polyvalency to novel biomaterial design by making new biomaterials that can modulate tissue injury pathways.

As polyvalency requires multiple and co-operative receptor-ligand interactions, pharmacological intervention will also require new medicines that are based upon molecules that are also capable of multiple and co-operative interactions. This has already been achieved with protein-based medicines, which interact with multiple cell surface receptors with high affinity. For many years, the aim has been to achieve analogous co-operative interactions with synthetic macromolecules. However, it has been found that in biological systems, the use of linear polymers has been much less successful than anticipated. Attempts to use linear polymers have been impeded by:—(1) the structural heterogeneity of the macromolecules used; (2) an inability to control their size and molecular weight characteristics; and (3) the toxic side effects of activating complement and coagulation triggered pathways.

In addition, in the case of linear polymers displaying saccharides, they have a tendency to self-associate and to form micelles because of the amphiphilic characteristics of many polymer-saccharide combinations. In the case of polysaccharides, their structural heterogeneity and the complex nature of the chemistry involved in their preparation has impeded the manufacturing scalability and reproducible synthesis of defined oligosaccharide-like molecules with the appropriate biological properties. In general, many synthetic steps are required, and the polar nature of the chemical intermediates and products make them difficult to purify. These compounds are also difficult to handle because they tend to be hygroscopic syrups, chemically labile, susceptible to rapid microbial degradation, and difficult to process into medicines. These fundamental problems have impaired the scale up manufacture of saccharide based macromolecules for pharmaceutical use.

WO 03/089010 disclosed certain glycodendrimers based on the PAMAM core. Generation three of PAMAM dendrimers conjugated to glucosamine or glucosamine sulfate to form a 3.5 generation dendrimer have been extensively studied.

These molecules have been shown to have very interesting biological activity and low toxicity, and in particular have significant anti-cytokine and anti-chemokine properties.

However, these compounds have not been progressed as pharmaceutical products and have never been dosed to a human because, to date, no way has been identified to commercially and viably manufacture them to a level of "purity" that is suitable for administration to a human. What is more many of the so called "impurities" are very closely related chemical species to the desired species and thus separation of the different entities is very difficult and may not be possible using currently available chromatography and/or filtration based techniques.

Whilst not wishing to be bound by theory it now believed by the present inventors that the chemistry on which PAMAM glycodendrimers is based is inherently incompatible with providing a molecule suitable for pharmaceutical use.

Nevertheless PAMAM glycodendrimers are special molecules because of their biological activity. Whilst many cores exist from which dendrimers can be made, it seems that glycodendrimers made from several alternative cores do not possess the requisite biological properties.

The present inventors believe that, surprisingly, the glycodendrimers described herein are likely to provide suitable biological properties to render them suitable for pharmacological intervention and additionally that the chemistry on which the molecules according to the invention are based is suitable for providing a molecule which can ultimately be used as a pharmaceutical product.

SUMMARY OF THE INVENTION

Thus there is provided a glycodendrimer comprising:
 a) a non-toxic dendrimer polypropyletherimine core supporting, on average, in the range of 9 to 64 terminal carboxylic acid groups, and
 b) conjugated to said core in the range of 2 to 8 amino sugars or a sulphate amino sugars selected from the group consisting of glucosamine, N-acetyl glucosamine, mannosamine, N-acetylmannosamine, galactosamine, a sulphate of any one of the same and a combination thereof,
wherein each sugar is linked directly through a zero length amide bond with a residue of terminal carboxylic acid groups.

DETAILED DESCRIPTION OF THE INVENTION

Dendrimers are a class of polymeric compounds that can be distinguished from conventional linear polymers by their highly branched, circular and symmetrical architecture.

The first dendrimers were made by divergent synthesis approaches by Vogtle in 1978, Denkewalter at Allied Corporation in 1981, Donald Tomalia at Dow Chemical in 1983 and in 1985 and by Newkome in 1985. In 1990, a convergent synthetic approach was introduced by Jean Frechet. Dendrimer popularity then greatly increased, resulting in more than 5,000 scientific papers and patents by 2005 (Hourani R et al. Advances in elegance of chemistry in designing dendrimers. Macromol. Rapid Commun 2010; 31: 947-74).

Divergent synthesis is essentially where the molecules are built up in layers from the centre outwards. The reference to generations is in essence a reference to the number of layering steps in the synthesis to produce the dendrimer. Thus in the divergent approach, the dendrimer is grown outwards from the core, typically there is a doubling of the number of reactive functionalities with each new "generation". However, care needs to be taken with the terminology, generation, because different starting materials require different techniques of synthesis, which can mean that a dendrimer of a certain "generation" made from one starting material may, in some ways, not necessarily be directly comparable to a dendrimer prepared from a different starting material, even though nominally they are given the same numerical generation. The term generation does not equate to absolute physical dimensions of the dendrimer.

In contrast, convergent synthesis is where the molecules are built in fragments and assembled as the last step or at a late stage of synthesis. Thus, the convergent growth method involves the synthesis of dendritic wedges possessing carbohydrates as one of the structural components, followed by the linking of these wedges to further components that provide branching, and then, finally, the attachment of these dendrons to the core component to obtain the desired dendrimer. The adoption of this convergent synthesis protocol typically results in larger quantities of the saccharide being displayed on the surface of the dendrimer in particular it may result in a complete saccharide capping on the dendrimer when the final dendrimer is assembled. Dendrimers prepared convergently are not assigned a generation.

Advantageously, dendrimers have a molecular structure that can be much more precisely defined than is possible for linear polymers (Tomalia D A, Naylor A M, Goddard III W A. (1990) Starburst dendrimers: molecular level control of size, shape, surface chemistry, topology and flexibility from atoms to macroscopic matter. Angewandte Chemie-International Edition, 29, 138-175.; Hourani R & Kakkar A. Advances in elegance of chemistry in designing dendrimers. Macromol. Rapid Commun. 2010; 31: 947-74).

As mentioned above, different starting materials can be used to generate the core. Dendrimers based on polyamidoamine (PAMAM) have been extensively studied. PAMAM dendrimers are prepared by divergent synthesis. Detailed reviews of divergently synthesised anionic carboxylic acid terminated PAMAM dendrimers can be found in WO 03/089010 and Shaunak S, Thomas S, Gianasi E, Godwin A, Jones E, Teo I, Mireskandari K, Luthert P, Duncan R, Patterson S, Khaw P & Brocchini S Polyvalent dendrimer glucosamine conjugates prevent scar tissue formation. Nature Biotechnology 2004; 22: 977-985.

PAMAM dendrimers are, by far, the best studied of the commercialised and divergently synthesised dendrimers. They are formed by the incremental addition of branched layers called generations onto a core. Typically, they are available in whole generations which are amine terminated, and half-generations which are carboxylic acid terminated. The generation of a dendrimer is therefore representative of both its size (measured as its diameter in angstroms) and its molecular weight (Vogte F, Richardt G, Werner N. Dendrimer chemistry—concepts, synthesis, properties and applications. 2009. Publisher Wiley. Chapter 1, pages 1-22) in relative terms.

Divergent dendrimers can also be synthesised from polypropyleneimine (PPI), polylysine, triazine and polypropyletherimine A detailed review in 2010 of the current field of divergently synthesised dendrimers and their applications can be found in:—Menjoge A R, Kannan R M, Tomalia D A, Dendrimer based drug and imaging conjugates: design considerations for nanomedical applications. Drug Discovery Today 2010; 15(5-6): 171-185).

There has been some evidence to suggest that dendrimers which terminate in free carboxylic acids, as opposed to those terminating in amine groups, have improved toxicological profiles ((Malik N, Wiwattanapatapee R, Klopsch R, Lorenz K, Frey H, Weener J W, Meijer E W, Paulus W & Duncan R. (2000) Dendrimers: Relationship between structure and biocompatibility in vitro, and preliminary studies on the biodistribution of 125I-labelled polyamidoamine dendrimers in vivo. J Controlled Release 65, 133-148).

However, when PPI dendrimers are synthesised the natural resulting terminal group is an amine. This motivated some in the field to try and convert amine terminated dendrimers to the corresponding carboxylic acid terminated dendrimer see Ashton P R, Boyd S E, Brown C L, Nepogodiev S A, Meijer E W, Peerlings H W I, Stoddart J F.

Synthesis of glycodendrimers by modification of poly(propylene imine) dendrimers. Chem. Eur. J. 1997; 3(6): 974-984. This led to complex reaction mixtures. Further studies with carboxylic acid terminated PPI dendrimers were therefore abandoned. Nevertheless, the authors converted amine terminated dendrimers into 100% surface glycosylated dendrimers using a spacer arm derivative of D-galactose and lactose.

Dendrimers have been applied to a number of fields. In the pharmaceutical field they have been investigated as drug carriers and in diagnostic applications. Very rarely have the dendrimers been considered therapeutic entities in their own right, partly because of their size and complex nature.

In the application of dendrimers as a drug carrier or as a diagnostic tool the field seems to have been obsessed with producing larger and larger dendrimers. There are many synthetic chemistry papers on the matter. However, it should be noted that it has been repeatedly demonstrated in the literature that high valency (in these large molecules) does not correspond with high biological affinity. In fact, the precise nature of the underlying scaffold is as important as the number of copies of saccharide ligand per molecule for molecules that are biologically active (Turnbull W B & Stoddard J F. Design and synthesis of glycodendrimers. Reviews in Molecular Biotechnology. 2002; 90: 231-255). That is to say the core is not simply an inert support for the amino sugar molecule.

Furthermore, the authors go on to conclude that although commercial dendrimers can be modified in such a way as to vary the surface density of their ligands, the de novo design of dendritic scaffolds is the best way forward in the quest for glycodendrimers with useful biological activities with carefully defined sizes, shape, flexibility and surface ligand density.

WO 03/089010 discloses a generation 3.5 PAMAM dendrimer with a partially glycosylated surface which has immuno-modulatory properties. About 15% or less of the surface terminal carboxylic acids are linked to glucosamine by a zero length amide bond.

In 2004, Shaunak showed that the generation G3.5 carboxylic acid terminated PAMAM dendrimer (MWt 12,931 with approximately 64 peripheral carboxylic acid groups) and with a 12.5% surface loading of glucosamine via a zero length amide bond blocked pro-inflammatory cytokine responses (Shaunak S, Thomas S, Gianasi E, Godwin A, Jones E, Teo I, Mireskandari K, Luthert P, Duncan R, Patterson S, Khaw P & Brocchini S Polyvalent dendrimer glucosamine conjugates prevent scar tissue formation. Nature Biotechnology 2004; 22: 977-985; Vogte F, Richardt G, Werner N. Dendrimer chemistry—concepts, synthesis, properties and applications. 2009 Publisher Wiley. Chapter 8: Special properties and potential applications. Pages 289-324 and also FIG. 2). This dendrimer glucosamine inhibited the release of the pro-inflammatory cytokines TNF-alpha, IL-1 beta and IL-6 from primary human monocytes, macrophages and dendritic cells by highly purified LPS. Importantly, this inhibitory effect was still seen when the dendrimer glucosamine was added 6 h after the LPS. The effect was dose-dependent and reversible with an $IC_{50}$ of 70 nM (FIGS. 3 & 4 & 5).

Whilst this PAMAM glycodendrimer molecule has some interesting in vitro and in vivo biological activity, in particular it can reduce pro-inflammatory cytokines and pro-inflammatory chemokines, and it has also been shown to be helpful in the prevention of excessive scarring in animal models, this molecule has not been progressed as a therapeutic agent (FIG. 1) because of the inability to make the molecule in a suitable form for use as a pharmaceutical.

The present inventors now have a better understanding of the mechanism of action of dendrimer glucosamine, for example in anti-cytokine and anti-chemokine mechanisms.

Lipopolysaccharide (LPS—variable MWt>10 kDa) is the outer membrane glycolipid of Gram-negative bacteria that induces this innate immune response. It is composed of:—
 (a) the hydrophilic polysaccharide core;
 (b) the solvent exposed hydrophobic lipid A component; and
 (c) the O-antigen.

Only the lipid A is required to induce pro-inflammatory cytokine responses. It is composed of a diphosphorylated β-1,6-linked D-glucosamine disaccharide linked via amide or ester bonds to 3-hydroxy fatty acids further substituted by nonhydroxylated 12-14 carbon fatty acid chains. The cell surface interaction between LPS, TLR4 and MD2 protein is central to the initiation of pro-inflammatory cytokine mediated responses. The transport protein CD14 first collects and delivers soluble LPS to soluble, circulating and monomeric MD2.

The two phosphorylated glucosamine residues of lipid A (MWt~2 kDa) bind via electrostatic interactions to the charged entrance (Ser118 {for the 4' phosphate} and Lys122 {for the 1' phosphate}, and to Arg90 and Lys91) of human MD2's hydrophobic pocket. The diglucosamine and phosphate groups remain in solution and outside the hydrophobic pocket; these residues serve to anchor LPS to the entrance of MD2's hydrophobic pocket.

This is followed by the lipid chains of LPS becoming buried in MD2's hydrophobic pocket. Subsequent formation of the human TLR4-MD-2-LPS complex requires:—(a) hydrophobic interactions between Met85, Leu87, Ile124 and Phe126 on human MD2 with Phe436, Phe436, Phe440 and Phe444 respectively on human TLR4; (b) hydrogen bond interactions between Arg90 and Gly123 on human MD-2 with Glu439 and Ser416 respectively on TLR4.

The complex formed undergoes conformational changes that lead to receptor complex dimerization, triggering of intracellular signalling events, and the initiation of pro-inflammatory cytokine production. Low level stimulation of pro-inflammatory cytokine production is physiologically beneficial for dealing with infections because it enables the activation of co-stimulatory molecules and the generation of adaptive immune responses. However, excess pro-inflammatory cytokine production can become pathological with serious adverse effects on the host which include septic shock and death.

Our analysis of the difference between the biologically active glycodendrimers and the biological inactive glycodendrimers leads us to believe that their interaction with specific amino acids residues at the entrance to the cavity of MD2 is important for their biological activity.

The hydrophilic entrance of the pocket on MD2 (to which Lipid A binds) is blocked by the glycodendrimer according to the present disclosure and in particular the dendrimer glucosamine. This prevents TLR4 dimerization and signalling events (Barata T S, Teo I, Brocchini S, Zloh M, Shaunak S. Partially glycosylated dendrimers block MD2 and prevent TLR4-MD2-LPS complex mediated cytokine responses. PLoS Comput Biol 2011; 7(6): e1002095. doi:10.1371/journal.pcbi.1002095).

Our studies have shown that the biologically active partially glycosylated dendrimer shows the largest number and the strongest interactions with several of the residues lining the entrance to MD2's pocket. Several of these residues are also important for the binding of LPS to MD2. The residues with the highest normalized interaction values were Lys91, Tyr102, Arg106, Asn114 and Ser118. Several other residues, with lower interaction values, also contributed significantly to the co-operative binding of the partially glycosylated dendrimer to human MD2; they were Arg96, Ser98, Lys109, Thr112 and Thr116.

Thus in one embodiment the dendrimers of the present disclosure interact with one or more (for example 1, 2, 3, 4 or 5) residues selected from Lys91, Tyr102, Arg106, Asn114 and Ser118.

It is believed that the glycodendrimers of the present disclosure interact with one or more of these important amino acids. Interact as employed herein refers to non-covalent bonding, for example hydrogen bonds, ionic bonds, van der Waals forces and hydrophobic interactions.

In one embodiment the dendrimer of the present disclosure interacts with Lys91.

In one embodiment the dendrimer of the present disclosure interacts with Tyr 102.

In one embodiment the dendrimer of the present disclosure interacts with Arg 106.

In one embodiment the dendrimer of the present disclosure interacts with Asn114.

In one embodiment the dendrimer of the present disclosure interacts with Ser118.

In one embodiment the dendrimer of the present disclosure interacts with:

Lys91 and Tyr102; Lys91 and Arg106; Lys91 and Asn114; Lys91 and Ser118; Tyr102 and Arg106; Tyr102 and Asn114; Tyr102 and Ser118; Arg106 and Asn114; Arg106 and Ser118, or Asn114 & Ser118.

In one or more embodiments the dendrimer of the disclosure also has at least one interaction (for example 2, 3, 4 or 5) with a residue selected from Arg96, Ser98, Lys109, Thr112 and Thr116.

In addition, the affinity of a partially glycosylated dendrimer for human MD2 was demonstrated by the increased number of close contacts (i.e., 1.3 Å) between these two molecules that involved both the glucosamine molecules and several of the dendrimer's peripheral carboxylic acid branches. These electrostatic interactions occluded the entrance to human MD2's hydrophobic pocket and are thought to blocked access of the lipid chains of LPS.

Thus it is hypothesised that the biological activity of the dendrimer surface results from the presence of both the amino sugars (or sulfate thereof) & free peripheral carboxylics that are from the core dendrimer.

Advantageously partially glycosylated dendrimers, for example according to the present disclosure are both flexible and dynamic, and have a hydrophilic periphery, this means that conformational changes could induce shape complementarity. Thus the interaction of the glycodendrimer according to the present disclosure with the biological target, may induce "conformational changes" in the molecule. This is thought to enable the dendrimer's surface saccharides such as glucosamines to block the entrance of MD2's pocket.

Additional co-operative electrostatic interactions with some of the dendrimer's free carboxylic acid branches follow. Collectively, these interactions are thought to block the entry of the lipid chains of LPS into human MD2's pocket, and also prevent TLR4-MD2-LPS cell surface complex formation. The biologically important outcome is that the pro-inflammatory cytokine cascade is not initiated.

Thus in one embodiment the dendrimer according to the present disclosure has an interaction with one or more of said amino acid residues in the target, for example as listed above. Close as employed herein is intended to refer to interactions of 2 Å or less such as 1.5 Å or less, in particular 1.3 Å.

We have also shown, for the first time, that the presence of lipidic chains is not an absolute requirement for an MD2 antagonist or partial antagonist.

Our molecular docking studies show that these partially glycosylated dendrimers bound to human MD2 and interfered with the electrostatic binding of:—

(i) the 4'phosphate on the di-glucosamine of LPS to Ser118 on MD2;

(ii) LPS to Lys91 on MD2; and (iii) the subsequent binding of TLR4 to Tyr102 on the MD2-LPS complex.

These three residues line the hydrophilic entrance of MD2's hydrophobic pocket. Additional polyvalent interactions between several other human MD2 surface residues [i.e., Arg96, Ser98, Arg106, Lys109, Thr112, Asn114 and Thr116] and several of the partially glycosylated dendrimer's peripheral carboxylic acid branches seems to enable it to position itself so that it always occludes the entrance to MD2's pocket. This blocks the entry of the lipid chains of LPS into human MD2's pocket and may explain the molecule's antagonist activity.

Taken together, the results from all of our modelling studies and our biological studies also suggest that the interaction of at least the G3.5 partially glycosylated PAMAM dendrimer (and more than likely the dendrimers of the present invention) with human MD2 is specific, and that a dendritic architecture is important for this molecule's biological activity (Barata T S, Shaunak S, Teo I, Zloh M, Brocchini S. Structural studies of biologically active glycosylated polyamidoamine (PAMAM) dendrimers. J Mol Model. Epub ahead of print: doi 10.1007/00894-010-0907-1; Barata T S, Brocchini S, Teo I, Shaunak S, Zloh M. From sequence to 3D structure of hyperbranched molecules: application to surface modified PAMAM dendrimers. J Mol Model. Epub ahead of print: doi 10.1007/x00894-011-0966-y; Barata T S, Teo I, Brocchini S, Zloh M, Shaunak S. Partially glycosylated dendrimers block MD-2 and prevent TLR4-MD-2-LPS complex mediated cytokine responses. PLoS Comput Biol 2011; 7(6): e1002095. doi:10.1371/journal.pcbi.1002095; Shaunak S, Thomas S, Gianasi E, Godwin A, Jones E, Teo I, Mireskandari K, Luthert P, Duncan R, Patterson S, Khaw P & Brocchini S Polyvalent dendrimer glucosamine conjugates prevent scar tissue formation. Nature Biotechnology 2004; 22: 977-985).

Therefore, our results suggest that at least two saccharides, such as glucosamine molecules, linked via the arms of a dendrimer are required to bind to several of the exposed and charged amino acids that line the entrance of the cavity on MD2. Thus the glycodendrimers of the present disclosure will generally comprise at least 2 amino sugars or sulfates thereof (including combinations of the same).

Having said this, the molecules of the disclosure will generally be provided as a population of molecules. The population may comprise a number of discrete molecules some of which may contain less than two amino sugar or amino sugar sulfates. Generally, the number of molecules with less than 2 amino sugars or amino sugar sulfates is low, for example less than 3%, such as 2%, 1% or less, in particular 0.5% or 0.1% w/w.

It is thought that electrostatic interactions over a 20 Angstrom range are responsible for this interaction between dendrimer for example dendrimer glucosamine and MD2 rather than hydrogen bond interactions (which can only occur over a distance of 4 Angstroms).

It is hypothesised that the optimum separation of the two sugar moieties such as the two glucosamine residues for this high affinity binding is probably 10 Å. The binding of dendrimer for example dendrimer glucosamine to the hydrophilic entrance of the pocket on MD2 almost completely occludes the entrance to the pocket in MD2; it also induces conformational changes in MD2 itself that make it very difficult for LPS to bind to the protein as an effective agonist. Advantageously this reduces pro-inflammatory cytokine production. This important new mechanistic observation shows that dendrimer aminosaccharides—without any lipid chains or phosphate groups attached to the dendrimer—can act as partial antagonists of the binding of LPS to the charged, hydrophilic entrance of the hydrophobic pocket on MD2 (FIGS. 6 & 7).

Whilst not wishing to be bound by theory it is thought that the surface properties (outer arm flexibility & charge distribution) & molecule size are vital to the biological activity, in particular that a combination of the amino sugar and free carboxylic acids and for example the cluster density such as the zero length amide bond formed are required on a suitably sized scaffold to block the target receptor and generate the therapeutic results. The hydrophilic surface of the glycodendrimer also has an important role to play.

Compounds able to produce co-operative effects are very important in modulating biological control mechanisms in the immune system, what is more they are seldom realised in purely synthetic molecules. The dendrimers of the present disclosure are suitable for producing co-operative effects in vitro and in vivo Whilst the data generated from the generation 3.5 anionic carboxylic acid terminated PAMAM dendrimer molecule has been very promising and exciting, one reason for its lack of progression is that despite repeated attempts by many workers in the field, to date, it has not been possible to prepare the molecule as a "monodispersion", in essence a characterisable population of molecules that can be reproducibly prepared to the satisfaction of the drug regulators. This is because, like all polymers, the final PAMAM dendrimer inevitably includes a mixture of minor components, resulting from side reactions that occur during the synthesis of the dendrimer. As with all polymers it is difficult to separate out these components to generate a single species. To date, no method is available for generating a single species of a PAMAM dendrimer. One may say that the chemistry is inherently flawed in that it is not possible to prevent side reactions occurring during the synthesis of this molecule.

Incomplete reactions and cyclization reactions with PAMAM chemistry mean that there is some structural heterogeneity to the PAMAM product. This means that it is very difficult to prepare this molecule with the purity and the reproducibility of scale-up manufacture and the degree of analytical chemical characterisation that is required of a new pharmaceutical for regulatory approval, for example from the FDA.

Thus it was necessary to consider realistic alternatives to PAMAM chemistry for achieving the desired biological outcomes with a molecule that had the purity and the reproducibility of scale up manufacture and the degree of analytical chemical characterisation required of a pharmaceutical drug. Thus the inventors have searched for a replacement molecule which shares the characteristics of the generation 3.5 PAMAM dendrimer molecule. However, it turns out that the surface characteristics, size, flexibility and hydrophilicity that provides the desirable biological profiles are not so easy to replicate.

Surprisingly, after almost 8 years of work in the field, the inventors have now identified a very limited number of glycodendrimers with the desirable biological properties, and with a core based on different chemistry which, with care, can be used to make a molecule that has the purity and the reproducibility of scale up manufacture and will meet the degree of analytical chemical characterisation required of a pharmaceutical drug, for example to generate a monodispersion that is, for example a substantially a single chemical entity.

The core is based on polypropyletherimine and surprisingly the glycodendrimers made employing this core seem to share some or all of the advantageous biological properties of the PAMAM glycodendrimer and may in one or more areas show improvements over the PAMAM glycodendrimer.

The polypropyletherimine has been produced at high purity (at least 95%) and polypropyletherimine-glucosamine has a white crystalline appearance.

The term "monodispersion" is used as per the meaning generally understood in the field of dendrimer chemistry. This means that the dendrimer has a narrow molecular weight distribution in which one particular species of a defined molecular weight is predominantly present. More specifically, the one particular species is present at 90% or more, for example 91, 92, 93, 94, 95, 96, 97, 98% or more.

Advantageously, the glycodendrimers of the present disclosure are believed to have useful biological properties and, generally, are capable of being prepared as a molecule that has the purity and the reproducibility of scale up manufacture and the degree of analytical chemical characterisation required of a pharmaceutical drug, for example susbstantially as a single chemical entity.

In one embodiment the glycodendrimer of the present invention is a mixture of a small number of well-defined chemical entities which are innocuous or substantially similar to the main dendrimer species and for example have similar biological activity.

Innocuous in the context of the present specification is intended to refer to an impurity that causes no deleterious effects and is essentially harmless in the biological context. Deleterious effects may, for example, relate to tissue toxicity or catalysis or degradation or any other property that could be considered a disadvantage for a medicine.

Substantially similar as employed herein is intended to refer to where the molecule comprises the same components as the desired species but they are present in a different ratio, for example substantially similar will generally refer to a glycodendrimer comprising the same core and sugars but the number of core carboxylics and/or the number or of sugars conjugated to the core is different to that which is desired.

In one embodiment the dendrimer core is prepared divergently and thus the resulting dendrimer can be assigned a generation.

In one embodiment the generation of the core dendrimer is 4 or less, such as 3, 2, 1 or 0.5.

Dendrimer core as employed herein is intended to refer to the branched dendrimer polymer before the surface is modified by the conjugation of the "amino sugar" thereto. Generally, if the final core is being considered then it will terminate in free carboxylic acids. However, if the core is at an intermediate stage it may terminate with a functional group other than a carboxylic acid.

Terminal carboxylic acid group as employed herein is intended to refer to a free carboxylic acid group —C(O)OH, located at the end of one surface branch of the dendrimer and any carboxylic acid residues.

Residue of a terminal carboxylic acid as employed herein is intended to refer to a portion of the terminal carboxylic acid left after a chemical reaction with another entity, such as the amino sugar for example —C(O)—.

Free carboxylic acid group is intended to refer to the unreacted (unconjugated carboxylic acid) —C(O)OH.

Glycodendrimer as employed herein is intended to refer to the entity resulting from conjugating the sugars, such as amino sugars to some of the terminal carboxylic acids on the dendrimer core.

The sugar, such as the amino sugar is linked to the dendrimer core by an amide bond formed by a nitrogen in the sugar with a carbonyl from a terminal carboxylic acid group. This is a direct amide bond, also referred to as a zero length amide bond.

In one embodiment on average the number of terminal carboxylic acids on the dendrimer core is in the range 10 or 12 to 48, for example 8, 12, 16, 24, 32, 40 or 48 such as 16, 24, 32 or 48.

In one embodiment the dendrimer core has 8, 9, 10, 11, 12, 13, 14, 15, 16, 17 or 18 carboxylic acids or a combination thereof.

In one embodiment the number of carboxylic acids on the dendrimer core is in the range 16, 17, 18, 19, 20, 23, 24, 25, 26, 27, 28 and a combination thereof. In one embodiment the average number of carboxylic acids on the dendrimer core is in the range 10 to 20, for example on average 14 to 18, such as on average 16 carboxylic acids, in particular 16 carboxylics.

It will be clear to a skilled person that generally for a given population of molecules the numbers of carboxylic acids present will, when calculated, be an average over the whole population.

In one embodiment the population is defined in that it will not include molecules with carboxylic acids below a defined lower threshold as well as above a defined upper threshold, for example where 16 carboxylic acid contained molecules are required the lower limit may be 12 and the upper limit may be 20 or even 18.

In one embodiment a glycodendrimer comprises a combined number of terminal carboxylic acids and carboxylic acid residues which corresponds to the number of free carboxylic acids in the starting core.

In the glycodendrimer molecules of the present disclosure there is at least one and generally more than one free carboxylic acid, for example where the number of carboxylic acids=X-Y, wherein X is a number in the range 9 to 64 (and corresponds to the number of carboxylic acids of the dendrimer core) and Y is a number in the range 2 to 8 (and corresponds the number of surface conjugated sugar molecules).

In one embodiment the number of free carboxylic acids is 8, 10, 14, 21, 28, 35 or 38 (or a combination thereof). In one embodiment the number of free carboxylic acids is 9, 10, 11, 12, 13, 14, 15, 16, 17, 18 or a combination thereof. In one embodiment the number of free carboxylic acids after conjugation is as average across the population is 12 to 14, for example 14. These free carboxylic acids are likely to have a role to play in facilitating the enhanced polyvalent binding of the glycodendrimer to the target receptor and hence are relevant to the biological activity of the molecules.

The glycodendrimers according to the disclosure may be provided as a discrete population of the molecules that this characterisable.

Advantageously, carboxylic acid terminated anionic polypropyletherimine dendrimers have a remarkable lack of toxicity in vitro compared to cationic polypropyletherimine dendrimers (Krishna T R & Jayaraman N. Synthesis of poly(propyl ether imine) dendrimers and evaluation of their cytotoxic properties. J. Organic Chemistry 2003; 68(25): 9,694-9,704; Jain S, Kaur A, Puri R et al. Polypropyletherimine dendrimer: A novel non-toxic dendrimer for sustained drug delivery. Eur J Med Chem 201; 45: 4997-5005). This inherent toxicity of higher generation cationic dendrimers means that they are unlikely to be suitable or safe for repeated intravenous administration as a pharmaceutical drug in man (Malik N, Wiwattanapatapee R, Klopsch R, Lorenz K, Frey H, Weener J W, Meijer E W, Paulus W & Duncan R. (2000) Dendrimers: Relationship between structure and biocompatibility in vitro, and preliminary studies on the biodistribution of 125I-labelled polyamidoamine dendrimers in vivo. Journal of Controlled Release 65, 133-148).

Thus the glycodendrimers of the present disclosure are believed to have low toxicity, which renders them suitable for use as a pharmaceutical.

In one embodiment there are on average in the range of 2 to 8, such as 3, 4, 5, 6 or 7 amino sugars conjugated to the dendrimer core, for example a core containing on average 16 carboxylic acids.

In one embodiment 2 amino sugars are conjugated to the dendrimer core.

In one embodiment the main species of glycodendrimer comprise 2 amino sugars but the population may, for example also comprise entities with 1 or 3 sugars.

In one embodiment there is provided a dendrimer core (for example with 16 carboxylic acids or a population with an average of 16 carboxylic acids) conjugated to 2, 3, 4 or 5, such as 2, 3 or 4, in particular 2 or 3 sugars. Also provided is a population comprising said molecules.

Even in a glycodendrimer population with the same number of sugar molecules conjugated thereto the molecules may be present as regio-isomers. That is to say the relative positions of the sugar entities in particular glycodendrimers may vary. That is to say the spatial arrangement of the sugars may differ in one molecule compared to another molecule in the population.

In one embodiment the number of region-isomers of the main glycodendrimer species is minimised, in particular, for a given population of glycodendrimers with the same number of sugars conjugated thereto at least 50% of said population will be the desired regio-isomer, in particular 75% will be the desired regio-isomer.

The region-isomer distribution may be influenced to provide the desired outcome by optimising the synthetic chemistry conditions during conjugation.

In one embodiment 30% or less of the dendrimers carboxylic acids are conjugated to a sugar, for example 29%, 28,%, 27%, 26%, 25%, 24%, 23%, 22%, 21%, 20% of the dendrimers carboxylic acids are conjugated, such as 28.75%.

In one embodiment 20% or less of the dendrimers carboxylic acids are conjugated to a sugar, for example 19%, 18,%, 17%, 16%, 15%, 14%, 13%, 12%, 11%, 10%, 9%, 8%, 7%, 6%, 5%, 4%, 3%, 2%, 1% or less of the dendrimers carboxylic acids are conjugated, such as 16.75 or 12.5%.

In one embodiment the number of conjugated carboxylic acids is in the range 3% to 14%, such as 6% to 13%, in particular 12.5%.

However the current inventors believe that at least two amino sugars are required in each molecule to effectively block the target receptor.

Furthermore in one aspect there is provided a highly optimized glycodendrimer comprising 2 amino sugars and 14 remaining terminal carboxylic acids. In one embodiment the dendrimer is a population of dendrimers where the latter entity is the major component, for example is a monodispersion.

This molecule (i.e., generation 3 anionic carboxylic acid terminated polypropyletherimine dendrimer glucosamine) is physically smaller than the generation 3.5 PAMAM dendrimer glucosamine previously described in the art. The generation 3.5 PAMAM dendrimer had 64 terminal carboxylic acids in the core.

In one embodiment the glycodendrimer according to the disclosure is a generation 4 molecule.

Surprisingly, this small polypropyletherimine dendrimer has only 16 terminal carboxylic acids in the core. At the same concentration (on a mg/ml basis), it is believed that the use of polypropyletherimine cores for preparation of said glycodendrimers can reduce some pro-inflammatory cytokines to an equal or a greater extent than the generation G3.5 PAMAM dendrimer glucosamine as summarised in Table 1 below.

TABLE 1

Summary table of results from several of the figures shown. It quantifies the fold reduction in pro-inflammatory cytokines with G3 polypropyletherimine dendrimer glucosamine when compared to G3.5 PAMAM dendrimer glucosamine. The 100% control = stimulation of cytokine release from cells that were stimulated with 25 ng/ml LPS.

| Cytokine | Drug concentration - tested in human cells (µg/ml) | | | | |
|---|---|---|---|---|---|
| | 200 | 100 | 50 | 25 | 12.5 |
| TNF-α | | | | | |
| G3 polypropyletherimine dendrimer glucosamine | nd | 390 | 570 | 807 | 477 |
| G3.5 PAMAM dendrimer glucosamine | 112 | 84 | 7 | 2 | nd |
| IL-8 | | | | | |
| G3 polypropyletherimine dendrimer glucosamine | nd | 165 | 192 | 288 | 17 |
| G3.5 PAMAM dendrimer glucosamine | 9 | 10 | 2 | 1 | nd |
| MIP-1β | | | | | |
| G3 polypropyletherimine dendrimer glucosamine | nd | 165 | 193 | 288 | 17 |
| G3.5 PAMAM dendrimer glucosamine | 54 | 53 | 6 | 2 | nd |
| IL-6 | | | | | |
| G3 polypropyletheriminedendrimer glucosamine | nd | 75 | 40 | 40 | 2 |
| G3.5 PAMAM dendrimer glucosamine | 835 | 910 | 178 | 5 | nd |

(nd = not done)

This small and optimized generation 3 (G3) polypropyletherimine dendrimer glucosamine may be particularly useful from a pharmaceutical perspective because it will be more cost effective to manufacture in respect of the starting materials employed to manufacture the same, and the ease of execution of the chemical steps required to manufacture the final medicinal product.

In one embodiment the surface coating of amino sugars on the dendrimer core is 18.75% or less, for example 15% or less, such as 12.5%.

The dendrimer core is a polypropyletherimine core. Usually this is based on units of 3-amino-propa-1-ol. Depending on how the dendrimer is synthesised, there can be an oxygen atom at the centre of the core or a nitrogen atom at the centre of the core. For details of polypropyletherimine dendrimers with nitrogen at the core see Krishna T R, Jain S, Tatu U S, Jayaraman N. Synthesis and biological evaluation of 3-amino-propanol-1-ol based poly(ether imine) dendrimers. Tetrahedron 2005; 61: 4281-4288. For details of polypropyletherimine dendrimers with oxygen at the core see the following papers:—Krishna T R & Jayaraman N. Synthesis of poly(propyl ether imine) dendrimers and evaluation of their cytotoxic properties. J. Organic Chemistry 2003; 68(25): 9,694-9,704; Jana C, Jayamurugan G, Ganapathy R, Maiti P K, Jayaraman N, Sood A K. Structure of poly(propyl ether imine) dendrimer from fully atomic molecular dynamics simulation and by small angle x-ray scattering. J. Chemical Physics 2006; 124: 204719; Jayamurugan G, Jayaraman N. Synthesis of large generation poly(propyl ether imine) dendrimers. Tetrahedron 2006; 62: 9582-9588.

In one embodiment the core is a polypropyletherimine based on 3-amino-propan-1-ol. These dendrimers can have an oxygen atom or a nitrogen atom at the very core of the molecule.

In one embodiment the dendrimer has an oxygen atom at the very core of the molecule.

In one embodiment the dendrimer has a nitrogen atom at the very core of the molecule.

The glycodendrimers herein are referred to as polypropyletherimine glycodendrimers.

These new anionic polypropyletherimine glycodendrimers are thought to bind to the cell surface TLR4 receptor on monocytes and macrophages and dendritic cells to reduce the production of the pro-inflamatory cytokines IL-6, TNF-alpha, IL-8 and/or IL-1 beta in response to LPS or hyaluronan fragments.

Surprisingly, these dendrimers cores when used provide the correct combination of features to support a required loading of an amino sugar or sugars and to provide the biological activity. It is especially surprising that the small generation polypropyletherimine glycodendrimers have advantageous biological activity.

In one aspect there is provided a generation 3 to generation 3.5 anionic carboxylic acid terminated (i.e., 16 to 64 peripheral carboxylic acid groups) dendrimer glucosamine with, for example a 12.5% surface loading of glucosamine (i.e., 2 to 8 glucosamine molecules) with a zero length amide bond between the dendrimer core and the glucosamine.

In particular there is provided a polypropyletherimine core (and a glycodendrimer comprising same) with 16 or 32 terminal carboxylic groups such as 16 carboxylic acid groups.

Clearly this desirable molecule may be provided as a population of molecules, in particular a defined population with average characteristics as defined herein.

Figure 31A:
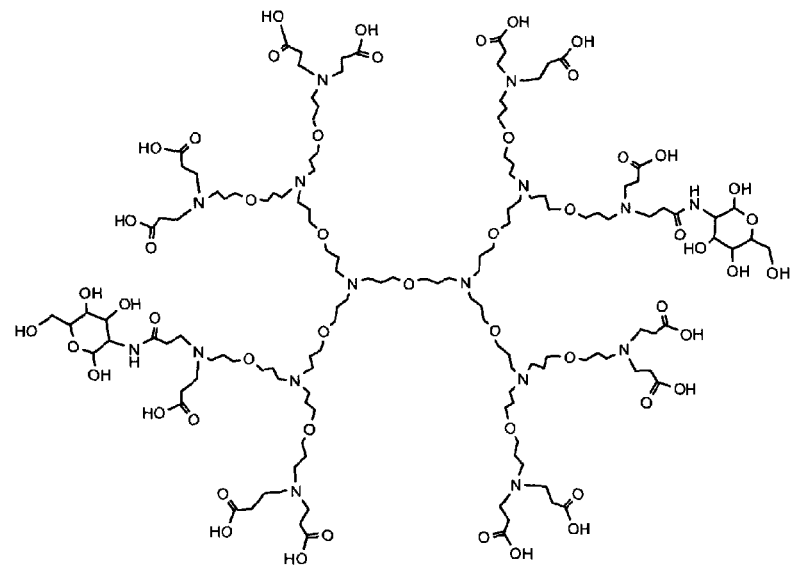
Figure 31B:
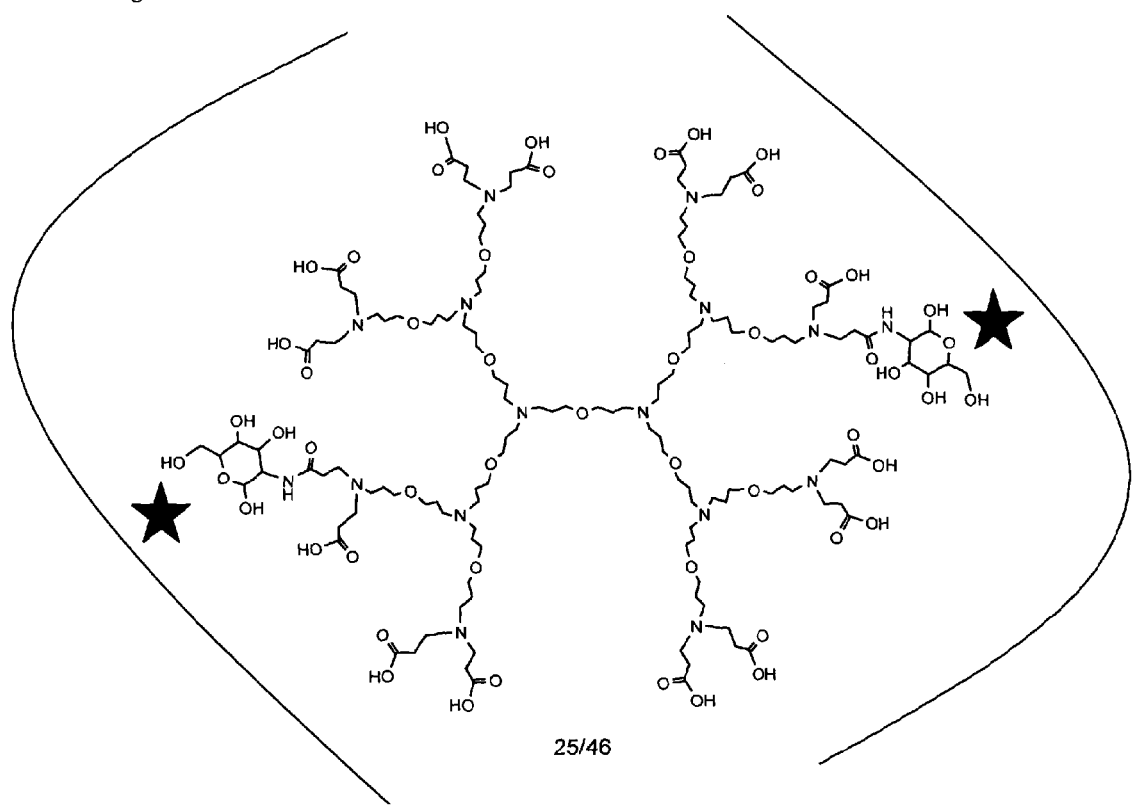

Thus in one embodiment there is provided a generation 3 anionic carboxylic acid terminated (i.e., 16 peripheral carboxylic acid groups) polypropyletherimine glycodendrimer (such as glucosamine glycodendrimer) with a 12.5% surface loading of sugar such as glucosamine (i.e. 2 sugar molecules such as glucosamine molecules) with a zero length amide bond between the dendrimer core and the sugar such as glucosamine. In one embodiment the two sugar molecules such as glucosamine molecules are present on opposite sides of the surface of the dendrimer as shown in FIG. 31 (that is to say spatially separated to be the maximum distance apart).

Thus in one embodiment there is provided a G3 anionic carboxylic acid terminated (i.e., 16 peripheral carboxylics) polypropyletherimine glycodendrimer (such as glucosamine glycodendrimer) with a 18.75% surface loading of sugar such as glucosamine (i.e. 3 sugar molecules such as glucosamine molecules) with a zero length amide bond between the dendrimer core and the sugar such as glucosamine.

In one embodiment there is provided a composition comprising a mixture of generation 3 anionic carboxylic acid termination polypropyletherimine glycodendrimer molecules bearing 2 or 3 sugars, such as 2 or 3 glucosamines.

Thus in one embodiment there is provided a generation 3 anionic carboxylic acid terminated (i.e., 16 peripheral carboxylic acid groups) polypropyletherimine glycodendrimer (such as glucosamine glycodendrimer) with a 25% surface loading of sugar such as glucosamine (i.e. 4 sugar molecules such as glucosamine molecules) with a zero length amide bond between the dendrimer core and the sugar such as glucosamine.

In one embodiment there is provided a composition comprising a mixture of generation 3 anionic carboxylic acid termination polypropyletherimine glycodendrimer molecules bearing 3 or 4 sugars, such as 3 or 4 glucosamines.

Thus in one embodiment there is provided a generation 3 anionic carboxylic acid terminated (i.e., 16 peripheral carboxylic acid groups) polypropyletherimine glycodendrimer (such as glucosamine glycodendrimer) with a 31.25% surface loading of sugar such as glucosamine (i.e. 5 sugar molecules such as glucosamine molecules) with a zero length amide bond between the dendrimer core and the sugar such as glucosamine.

In one embodiment there is provided a composition comprising a mixture of generation 3 anionic carboxylic acid termination polypropyletherimine glycodendrimer molecules bearing 4 or 5 sugars, such as 4 or 5 glucosamines.

The ratio of molecules bearing 2 sugars to molecules bearing other numbers of sugars in the mixture is in the range 1 to 99%:99 to 1% respectively and may for example be 50:50, 75:25 or 25:72 etc.

In one embodiment the glycodendrimer according to the disclosure has 13 or 14 free carboxylic acids, such as 14.

In one embodiment the glycodendrimer according to the disclosure has 13 free carboxylic acids, In one embodiment the glycodendrimer according to the disclosure has 12 free carboxylic acids.

In one embodiment the glycodendrimer according to the disclosure has 11 free carboxylic acids.

Opposite sides of the molecule as employed herein is intended to refer to diametrically opposed sugars, such as glucosamines, or a similarly thermodynamically and sterically favourable conformation.

It is hypothesised that this observation is consistent with higher occupied molecular orbital and lowest occupied molecular orbital calculations that were performed using the frontier molecular orbital theory. In the case of a generation 3 anionic carboxylic acid terminated (i.e., 16 peripheral carboxylic acid groups) polypropyletherimine dendrimer, the incremental addition of each glucosamine was found to proceed in a energy favourable manner until 2 glucosamine molecules have been attached to 2 of the 16 peripheral carboxylic acid groups available. Thereafter, the higher occupied molecular orbital energy values rapidly become unfavourable to the addition of additional glucosamine molecules although it is theoretically possible to attach up to 4 or 5 glucosamine molecules. This suggests that the divergent approach to the synthesis of dendrimer glucosamine is generally favourable to the addition of 2 glucosamine molecules to two of the 16 carboxylic acid groups of a generation 3 anionic carboxylic acid terminated polypropyletherimine dendrimer. Typically, the two glucosamine molecules are situated at diametrically opposite ends of the surface of the dendrimer (Barata T S, Shaunak S, Teo I, Zloh M, Brocchini S. Structural studies of biologically active glycosylated polyamidoamine (PAMAM) dendrimers. J Mol Model. Epub ahead of print: doi 10.1007/s00894-010-0907-1; Barata T S, Brocchini S, Teo I, Shaunak S, Zloh M. From sequence to 3D structure of hyperbranched molecules: application to surface modified PAMAM dendrimers. J Mol Model. Epub ahead of print: doi 10.1007/s00894-011-0966-y: Barata T S, Teo I, Brocchini S, Zloh M, Shaunak S. Partially glycosylated dendrimers block MD-2 and prevent TLR4-MD2-LPS complex mediated cytokine responses. {In press in PLOS Computational Biology}).

In one embodiment, there is provided a dendrimer with a ratio of combined terminal carboxylics/acid resides to the number of amino sugars conjugated thereto is in the range 8:1 to 6:1, in particular 8:1.

The term sugars and amino sugars are employed herein generically to refer to amino sugars and sulfates thereof unless the context implies otherwise.

In one embodiment the amino sugar is glucosamine, N-acetylglucosamine, glucosamine 2-sulphate, glucosamine 3-sulphate, glucosamine 6-sulphate, glucosamine 2,6-disulphate, glucosamine 3,6-disulphate, glucosamine 3,4,6-trisulphate, N-acetyl glucosamine 2-sulphate, N-acetyl glucosamine 3-sulphate, N-acetyl glucosamine 6-sulphate, N-acetyl glucosamine 2,6-disulphate, N-acetyl glucosamine 3,6-disulphate or N-acetyl glucosamine 3,4,6-trisulphate or a combination thereof.

In one embodiment the sugar is selected from glucosamine, glucosamine 2-sulphate, glucosamine 3-sulphate, glucosamine 6-sulphate and a combination thereof, for example in a generation 3 glycodendrimer according to the present disclosure.

In one embodiment the sugar is glucosamine, for example in a generation 3 glycodendrimer according to the present disclosure.

In one embodiment the sugar is selected from glucosamine 2-sulphate, glucosamine 3-sulphate and glucosamine 6-sulphate, for example in a generation 3 glycodendrimer according to the disclosure.

In one embodiment the amino sugar is mannosamine or galactosamine or a derivative thereof or a combination thereof, for example, sulphated and/or acylated derivatives corresponding to the above glucosamine derivatives.

In one embodiment the amino sugar is mannosamine, for example in a mannoamine generation 3 polypropyletherimine glycodendrimer according to the present disclosure. In one embodiment there is provided a dendrimer generation 3 mannosamine sulphate glycodendrimer, or dendrimer generation 3 N-acetylmannosamine glycodendrimer, or dendrimer generation 3 N-acetylmannosamine sulphate glycodendrimer, or any combination thereof.

In one embodiment a combination of one or more of the above identified sugars are used to conjugate to the dendrimer core.

In one embodiment the amino sugars such as glucosamines are evenly spaced on the surface of the dendrimer.

Evenly spaced as employed herein is intended to refer to the fact that the sugars are spread across the surface of the dendrimer in a balanced manner and are not clumped together in one or more isolated locations on the surface.

Advantageously, dendrimers are hyperbranched, wherein the ends of each branch define the molecular surface of the dendrimer. Notably, (1) their physico-chemical properties are similar to those of conventional small molecule drugs; (2) they can be modified to exist as zwitterions at physiological pH; and (3) they have a considerable buffering capacity that makes them physico-chemically "similar" to blood proteins (e.g., albumin), and therefore biocompatible. However, unlike proteins, they (1) do not undergo proteolytic degradation in plasma; (2) are not immunogenic; (3) are not toxic after repeated intravenous administration; (4) can be optimized for their circulation time; and (5) show preferential accumulation in tissues containing inflammatory cells compared to healthy tissue at a ratio of 50:1. In addition, the National Cancer Institute's Nanotechnology Characterisation Laboratory recently undertook detailed chemical and toxicological characterization of anionic PAMAM dendrimers and found them to be both stable and biocompatible (see the Nanotechnology Characterisation Laboratory NCI (2006) Dendrimer-based MRI contrast agents website—http://ncl.cancer.gov/working_technical_reports.asp).

Advantageously, the glycodendrimers of the present disclosure are stable, in that they are suitable for storage under appropriate conditions before use, for example use as a therapeutic agent.

In a further aspect, the present invention provides a pharmaceutical formulation comprising a polypropyletherimine glycodendrimer of the invention and optionally a pharmaceutically acceptable carrier/excipient.

In one embodiment the formulation comprises 10 μg to 1 g of glycodendrimer of the present disclosure.

The compounds and formulations of the invention are suitable for administration parentherally for example intravenously, subcutaneously, intramuscularly, intraperitoneally and intraocularly; orally; topically including by aerosol, for example intranasally, by pulmonary administration, directly to the eye, transdermally (skin) such as via an impregnated plaster or a skin patch, in particular to the surface of the skin transdermal by a slow release preparation; and intramucosally for example by buccal or rectal administration, for example as a rectal enema wherein the compound is formulated in a suitable carrier such as an aqueous carrier.

Topical administration as employed herein includes administration orally to the GI tract and colon etc, wherein the compound administered is not absorbed systemically.

In another aspect, the invention provides a pharmaceutical composition comprising, as active ingredient, a compound of the disclosure or a pharmaceutically acceptable derivative thereof in association with a pharmaceutically acceptable excipient, diluent and/or carrier for use in therapy, and in particular, in the treatment of human or animal subjects suffering from a condition susceptible to amelioration by an antimicrobial compound.

An active ingredient as employed herein is intended to refer to a pharmacologically effective ingredient, for example which are therapeutically efficacious. Examples of active ingredients include corticosteroids, for example fluticasone propionate, fluticasone furoate, mometasone furoate, dexamethasone, cortisone, hydrocortisone, betamethasone, prednisolone; non-steriodal anti-inflammatories for example aspirin, ibuprofen, naproxen.

There is further provided by the present disclosure a process of preparing a pharmaceutical composition, which process comprises mixing a compound of the disclosure or a pharmaceutically acceptable derivative thereof, together with a pharmaceutically acceptable excipient, diluent and/or carrier.

The compounds of the disclosure may be formulated for administration in any convenient way for use in human or veterinary medicine and the disclosure therefore includes within its scope pharmaceutical compositions comprising a compound of the disclosure adapted for use in human or veterinary medicine. Such compositions may be presented for use in a conventional manner with the aid of one or more suitable excipients, diluents and/or carriers. Acceptable excipients, diluents and carriers for therapeutic use are well known in the pharmaceutical art, and are described, for example, in Remington's Pharmaceutical Sciences, Mack Publ Co. (A. R. Gennaro edit. 1985). The choice of pharmaceutical excipient, diluent &/or carrier can be selected with regard to the intended route of administration and standard pharmaceutical practice. The pharmaceutical compositions may comprise as —or in addition to—the excipient, diluent and/or carrier any suitable binder(s), lubricant (s), suspending agent(s), coating agent(s), solubilising agent (s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may also be used.

For some embodiments, the agents of the present disclosure may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e. g. as a carrier, diluent or solubiliser. Alpha-, beta- and gamma-cyclodextrins are most commonly used and suitable examples are described in WO 91/11172, WO 94/02518 and WO 98/55148.

The compounds of the disclosure may be milled using known milling procedures such as wet milling to obtain a particle size appropriate for tablet formation and for other formulation types. Finely divided (nanoparticulate) preparations of the compounds of the invention may be prepared by processes known in the art, for example see International Patent Application No. WO 02/00196.

The routes for administration (delivery) include, but are not limited to, one or more of: oral (e. g. as a dry powder/free flowing particulate formulation, tablet, capsule, or as an ingestable solution or suspension) rectal, buccal, and sublingual. The compositions of the disclosure include those in a form especially formulated for parenteral, oral, buccal, rectal, topical, implant, ophthalmic, nasal or genito-urinary use. In one aspect of the invention, the agents are delivered orally, hence, the agent is in a form that is suitable for oral delivery.

In some instances it may be possible to deliver the compounds of the disclosure by a topical, parenteral (e. g. by an injectable form) or transdermal route, including mucosal (e. g. as a nasal spray or aerosol for inhalation), nasal, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral).

There may be different composition/formulation requirements depending on the different delivery systems. By way of example, the pharmaceutical composition of the present disclosure may be formulated to be delivered using a minipump or by a mucosal route, for example, as a nasal spray or aerosol for inhalation or ingestable solution, or parenterally in which the composition is formulated in an injectable form, for delivery by, for example, an intravenous, intramuscular or subcutaneous route. Alternatively, the formulation may be designed to be delivered by both routes. Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously.

For buccal or sublingual administration the compositions may be administered in the form of tablets or lozenges which can be formulated in a conventional manner.

For parenteral administration, the compositions may be best used in the form of a sterile aqueous solution which may contain other substances, for example enough salts or monosaccharides to make the solution isotonic with blood.

If a compound of the present disclosure is administered parenterally, then examples of such administration include one or more of: intravenously, intraarterially, intraperitoneally, intrathecally, intraventricularly, intraurethrally, intrasternally, intracranially, intramuscularly for example as a bolus formulation or subcutaneously administering the agent, and/or by using infusion techniques.

Formulations for parenteral administration may be provided in a lyophilised form for reconstitution with a water of injection or infusion or an isotonic solution, such as glucose.

The compounds of the disclosure can be administered (e.g. orally or topically) in the form of tablets, capsules, ovules, elixirs, solutions or suspensions, which may contain flavouring or colouring agents, for immediate-, delayed-, modified-, sustained-, pulsed- or controlled-release applications.

The compounds of the disclosure may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents.

Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, calcium sulphate, dibasic calcium phosphate and glycine, mannitol, pregelatinised starch, corn starch, potato starch, disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and *acacia*.

Additionally, lubricating agents such as magnesium stearate, stearic acid, glyceryl behenate and talc may be included.

Solid compositions of a similar type may also be employed as fillers in gelatin or HPMC (hydroxypropyl methylcellulose) capsules. Preferred excipients in this regard include microcrystalline cellulose, lactose, calcium carbonate, calcium sulphate, dibasic calcium phosphate and, mannitol, pregelatinised starch, corn starch, potato starch or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

Capsules, may be filled with a powder (of medicament alone or as blend with selected filler(s)) or alternatively a liquid, each comprising one or more compounds of the invention and a carrier. Where the capsule is filled with a powder the compounds of the invention and/or the carrier may be milled or micronised to provide material with an appropriate particle size.

Compounds of the disclosure may be coated, for example with an enteric coating when administered orally as a tablet or capsule. The tablet or capsule, as appropriate, may, for example be coated by a thin film such as a EUDRAGIT® film available from Rohm Pharma Polymers, which allows controlled dissolution in the gastrointestinal tract. The films are available as cationic polymers such as EUDRAGIT® E 100 (aminoalkyl methacylate copolymers) or as anionic acrylic polymers such as EUDRAGIT® L (methacrylic acid copolymers) and EUDRAGIT S.

Permeable acrylic polymers such as EUDRAGIT® RL (amino methacrylate copolymer) and EUDRAGIT® RS are also available.

These coating formulations may be prepared as an aqueous dispersion including optional ingredients such as talc, silicone antifoam emulsion, polyethylene glycol. Alternatively the coating formulation may be prepared as an organic polymer solution.

Alternatively, tablets may be coated using OPADRY® (Surelease®) coating systems, available from Colorcon. Aqueous systems generally comprise up to 15% w/w of OPADRY®. Organic solvent systems generally comprise up to 5% w/w of OPADRY®.

The coatings may be prepared by known techniques, for example by;
1. weighing the required quantity of OPADRY® film coating system, 2. weighing the required quantity of water or other solvent(s) into a mixing vessel, 3. with a mixing propeller in the centre of the vessel and as close to the bottom of the vessel as possible, stirring the solvents to form a vortex without drawing air into the liquid, 4. steadily and quickly adding the OPADRY® powder to the vortex, avoiding powder flotation on the liquid surface, 5. increasing the stirrer speed in order to maintain the vortex, if required, and 6. after all the powder ingredients have been added, reducing the mixer speed and continuing mixing for approximately 45 minutes.

Coatings can be applied by known techniques, using tablet coating machines. The thickness of the coating applied is generally in the range 5 to 35 microns such as 10 to 30 microns, more specifically 10 or 20 microns, depending on the required effect.

Alternatively, the tablet or a capsule, as appropriate, may be filled into another capsule (preferably a HPMC capsule such as Capsugel®) to provide either a tablet in capsule or capsule in capsule configuration, which when administered to a patient yields controlled dissolution in the gastrointestinal tract thereby providing a similar effect to an enteric coating.

Thus in one aspect the disclosure provides a solid dose formulation of a compound of invention for example where the formulation has an enteric coating.

In another aspect the disclosure provides a solid dose formulation comprising a protective capsule as outer layer, for example as a tablet in a capsule or a capsule in a capsule. The enteric coating may provide an improved stability profile over uncoated formulations.

The compounds of the disclosure may also be administered orally, in veterinary medicine, in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

In one embodiment the formulation is provided as a formulation for topical administration including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or di-saccharides are preferably used, the use of lactose or glucose, particularly but not exclusively in the form of their hydrates.

Particles for deposition in the lung require a particle size less than 10 microns, such as 1-9 microns suitably from 0.1 to 5 µm, particularly preferably from 1 to 5 µm. The particle size of the active (i.e. the compound according to the disclosure) should be in this range. The size of particle of excipients such as lactose may be larger than this range.

The propellant gases which can be used to prepare the inhalable aerosols are known from the prior art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The above-mentioned propellent gases may be used on their own or in mixtures thereof.

Particularly suitable propellent gases are halogenated alkane derivatives selected from among TG11, TG12, TG 134a and TG227. Of the abovementioned halogenated hydrocarbons, TG134a (1,1,1,2-tetrafluoroethane) and TG227 (1,1,1,2,3,3,3-heptafluoro propane) and mixtures thereof are suitable for use in formulations of the present invention.

The propellant-gas-containing inhalable aerosols may also contain other ingredients such as co-solvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the disclosure may contain, for example, 0.002 to 5% by weight, 0.01 to 3% by weight, 0.015 to 2% by weight, 0.1 to 2% by weight, 0.5 to 2% by weight or 0.5 to 1% by weight of active.

The compounds of the disclosure may also be used in combination with other therapeutic agents. The disclosure thus provides, in a further aspect, a combination comprising a compound of the present disclosure or a pharmaceutically acceptable derivative thereof together with a further therapeutic agent. The combination may be provided as a co-formulation or simply packaged together as separate formulations, for simultaneous or sequential delivery.

A list of possible active ingredients that may complement the therapeutic activity of the glycodendrimer according to the present disclosure is given above.

Therapeutic antibodies may also complement the therapeutic activity of the glycodendrimer according to the present disclosure. Examples of therapeutic antibodies include anti-TNF-alpha antibodies, for example etanercept, infliximab, adalimumab, certolizumab pegol, golimumab; Interleukin-1 antibodies, for example anakinra; rituximab; abatacept; and tocilizumab.

It is to be understood that not all of the compounds (or molecules) of the combination need be administered by the same route. Thus, if the therapy comprises more than one active component, then those components may be administered by different routes.

The individual components of such combinations may be administered either sequentially or simultaneously in separate or combined pharmaceutical formulations by any convenient route.

When administration is sequential, either the compound of the disclosure or the second (further) therapeutic agent may be administered first. When administration is simultaneous, the combination may be administered either in the same or a different pharmaceutical composition.

The combinations referred to above may conveniently be presented for use in the form of a pharmaceutical formulation and thus pharmaceutical formulations comprising a combination as defined above together with a pharmaceutically acceptable carrier or excipient comprise a further aspect of the disclosure.

When combined in the same formulation it will be appreciated that the two compounds must be stable and compatible with each other and the other components of the formulation. When formulated separately they may be provided in any convenient formulation, in such manner as are known for such compounds in the art.

The compositions may contain from 0.01-99% of the active material. For topical administration, for example, the composition will generally contain from 0.01-10%, more preferably 0.01-1% of the active material.

Processes for preparing said pharmaceutical formulations may, for example, be performed under controlled environments, such as controlled humidity conditions.

In one embodiment the pharmaceutical formulation is protected from light, for example is stored in amber bottles or vials, foil wrapped or packaged, such as foil overwrapped or filled into foil blister packs or foil sachets. In one embodiment the pharmaceutical formulation is protection from moisture, for example foil wrapped or packaged, such as foil overwrapped or filled into foil blister packs or foil sachets. In one embodiment the formulation is protected from air/oxygen, for example by storage under nitrogen.

Blister packaging is well known to those skilled in the art, however, in one embodiment the blister is a so-called tropical blister available from amcor or a similar blister available from Alcan. US2006/0283758 incorporated by reference discloses certain blister packs suitable for use with formulations of the invention.

Advantageously appropriately packaged formulations of the present disclosure can be stored at room temperature.

When a compound of the disclosure or a pharmaceutically acceptable derivative thereof is used in combination with a second therapeutic agent active against the same disease state, the dose of each compound may be the same or differ from that employed when the compound is used alone. Appropriate doses will be readily appreciated by those skilled in the art. It will also be appreciated that the amount of a compound of the disclosure required for use in treatment will vary with the nature of the condition being treated and the age and the condition of the patient and will be ultimately at the discretion of the attendant physician or veterinarian.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

For oral and parenteral administration to humans, the daily dosage level of the agent may be in single or divided doses. For systemic administration the daily dose as employed for adult human treatment will range from 2-100 mg/Kg body weight, preferably 5-60 mg/Kg body weight, which may be administered in 1 to 4 daily doses, for example, depending on the route of administration and the condition of the patient. When the composition comprises dosage units, each unit will preferably contain 100 mg to 1 g of active ingredient. The duration of treatment will be dictated by the rate of response rather than by arbitrary numbers of days. In one embodiment the treatment regime is continued for 1, 2, 3, 4, 5, 6, 7, 8, 9, 10, 11, 12, 13, 14, 15, 16, 17, 18, 19, 20, 21 or more days.

As described above, the compounds of the present disclosure and composition comprising the same may be employed in the treatment or prophylaxis of humans and/or animals.

Managing Uncontrolled Immunological Trauma in Elective Surgery

Elective surgery causes the release of tissue enzymes that degrade high molecular weight hyaluronan into low molecular weight hyaluronan. The small fragments trigger TLR4 mediated pro-inflammatory responses in a manner that is almost identical to bacterially derived LPS. An excessive pro-inflammatory cytokine release interferes with the normal phases of wound healing. The excessive angiogenesis that accompanies this host innate immune response increases pro-inflammatory monocyte recruitment to the wound site. Scarring is due to a persistent pro-inflammatory response that promotes fibroblast proliferation. Shaunak postulated that early inhibition of an immuno-modulatory pathway and an anti-angiogenic pathway would enable physiological (rather than pathological) repair and regeneration of surgically induced injury without causing scar tissue formation.

A rabbit model of glaucoma filtration surgery was chosen because the surgical intervention is precisely defined, and because surgical failure results from an excessive pro-inflammatory response combined with a neo-angiogenic response. When used in combination, PAMAM dendrimer glucosamine and PAMAM dendrimer glucosamine 6-sulfate increased the success rate of glaucoma filtration surgery from 30% to 80% (P=0.029) in this clinically validated rabbit model. Therefore, this combination of dendrimer based drugs safely and synergistically prevented scar tissue formation after surgery. Histological studies showed that the degree of tissue based inflammatory cell infiltration and abnormal collagen formation was minimal (Shaunak S, Thomas S, Gianasi E, Godwin A, Jones E, Teo I, Mireskandari K, Luthert P, Duncan R, Patterson S, Khaw P & Brocchini S. Polyvalent dendrimer glucosamine conjugates prevent scar tissue formation. Nature Biotechnology 2004; 22: 977-985; Atala A, Irvine D J, Moses M, Shaunak S. Wound healing versus regeneration: Role of the tissue environment in regenerative medicine. MRS Bulletin August 2010; 35: 597-606).

It is believed that the glycodendrimers of the present invention also have these properties. Thus there is provided a glycodendrimer of the present disclosure or a combination thereof or a pharmaceutical composition comprising the same for use in treatment or prohylaxis, in particular the treatment or prophylaxis of surgery induced tissues damage or tissue injury or damage that if untreated would lead to scaring and impairment of the original tissue function, for example for the treatment or prevention of scar tissue in eye tissue.

In one embodiment the glycodendrimer employed in this embodiment comprises a combination of amino sugars and amino sugar sulfates, for example a combination of glycosamine and glucosamine sulfate (such as glucosamine 6-sulfate). In one embodiment a combination of glycodendrimers is employed, for example a glycodendrimer comprising an amino sugar and a glycodendrimer comprising an amino sugar sulfate, for example a generation 3 glucosamine polypropyletherimine glycodendrimer and a generation 3 glucosamine sulfate (such as glucosamine 6-sulfate) polypropyletherimine dendrimer.

Tissue Damaging Cascades

Both surgical trauma and bacterial infections can lead to severe tissue injury that can be triggered by cell surface TLR4 mediated receptor-ligand interactions. These polyvalent interactions between bacterially derived ligands as well as endogenous hyaluronan fragments can lead to the release of life threatening pro-inflammatory cytokines such as IL-6 and TNF-alpha and IL-8. As a result, this pathway is tightly regulated in all biological organisms. The checkpoints that initiate as well as arrest this tissue damaging cascade are important because they have the potential of being manipulated with pharmaceutical drugs.

Thus in one embodiment there is provided use of a compound according to the disclosure and compositions comprising the same for the treatment or prophylaxis of scarring, including excessive scarring, particularly after surgery, whether internal to the body or relating to a surface organ of the body; e.g. such as the skin or a mucosal surface or a surface related to the eye.

The Inflammatory Response Associated with Bacterial Infections

Fundamental to innate immunity are the pattern recognition receptors (TLRs) that recognize pathogen associated molecular patterns. They allow the immune system to distinguish self structures from pathogen associated non-self-molecules. They are the first line of host defense against invading pathogens (Zuany-Amorim C, Hastewell J, Walker C. Toll-like receptors as potential therapeutic targets for multiple diseases. Nature Reviews Drug Discovery 2002; 1: 797-807).

TLR4 on macrophages and dendritic cells is the key cell surface receptor. Antigen mediated triggering leads to cytokine expression, dendritic cell maturation, and adaptive immune responses.

The outer membrane of all Gram-negative bacteria is made up of a bilayer that consists of phospholipids on the inner leaflet, and the lipid anchor region of lipopolysaccharide (LPS) (i.e., lipid A) on the outer leaflet. Recognition of LPS occurs as part of the TLR4-MD—CD14 receptor complex. Park et al have recently defined the structural basis of the recognition of LPS by TLR4-MD2 (Park B S, Song D H, Kim H M, Choi B S, Lee H, Lee J O. The structural basis of lipopolysaccharide recognition by the TLR4-MD-2 complex. Nature 2009; 458: 1191-1195). In brief, MD2 has a hydrophobic pocket that is lined by a charged, hydrophilic entrance. Lipid A (which consists of two phosphorylated glucosamine molecules linked together via an ester bond) binds to the entrance of this pocket and its lipid chains then enter MD-2's hydrophobic pocket. The TLR4-MD2-LPS complex undergoes a conformational change and TLR4 dimerizes. Intracellular signalling follows.

Only a very short stimulation of TLR4 is required to lead to dendritic cell maturation and T cell stimulation. This contrasts with the prolonged and sustained stimulation of TLR4 that is required for the induction of pro-inflammatory cytokines such as TNF-$\alpha$ and IL-6. Distinct thresholds therefore exist within the TLR4-MD2-LPS complex (at the level of the cell surface) for inducing the expression of CD markers of cellular differentiation compared to the release of cytokines (Park B S, Song D H, Kim H M, Choi B S, Lee H, Lee J O. The structural basis of lipopolysaccharide recognition by the TLR4-MD-2 complex. Nature 2009; 458: 1191-1195). This unique nature of TLR4 compared to all other TLR receptors has only been recently recognized (Kagan J C, Su T, Horng T, Chow A, Akira S, Medzhitov R. TRAM couples endocytosis of Toll-like receptor 4 to the induction of interferon-beta. Nature Immunology 2008; 9: 361-368).

Thus in one aspect there is provided use of compounds of the present disclosure and compositions comprising same for the treatment or prophylaxis of inflammatory responses or inflammatory disease, for example a response mediated by increased levels of one or more cytokines selected from the group comprising IL-6, TNF-alpha, IL-8, IL-1 beta and MIP-1 beta. In one embodiment the inflammatory mechanism is in response, for example in response to LPS and/or hyaluronan fragments that bind to the cell surface receptor TLR4 and/or to bacterial infection, for example in the lining of the gut.

In one embodiment there is provided a glycodendrimer according to the present disclosure or a composition comprising the same for the treatment or prophylaxis of inflammation associated with Gram negative infections, for example Gram negative infection is associated with inflammatory diarrhoeas, such as those caused by *Shigella* sp. and *Salmonella* sp and *Campylobacter* sp. and *Clostridium difficile* and *E. coli*.

In one embodiment there is provided a glycodendrimer according to the present disclosure or a composition comprising the same for use in the treatment or prophylaxis of inflammatory bowel disease, such as Crohn's Disease and/or Ulcerative Colitis.

In one embodiment there is provided a glycodendrimer according to the present disclosure or a composition comprising the same for use in the treatment or prophylaxis of those forms of irritable bowel disease, for example associated with an excessive stimulation of Toll Like receptors by gut bacteria.

In one embodiment there is provided a glycodendrimer according to the present disclosure or a composition comprising the same for use in the treatment or prophylaxis of abnormally excessive host pro-inflammatory cytokine mediated responses in the respiratory system such as those that occur in allergy, asthma or after a bacterial and/or viral infection.

In one embodiment there is provided a glycodendrimer according to the present disclosure or a composition comprising the same for use in the treatment or prophylaxis of excessive scarring during wound healing, keloid formation, eczema and psoriasis.

In one embodiment there is provided a glycodendrimer according to the present disclosure or a composition comprising the same for use in the treatment or prophylaxis of transplants or organs or tissue, such as corneal and/or skin transplantation.

In one embodiment there is provided a glycodendrimer according to the present disclosure, in particular a glycodendrimer comprising an amino sugar sulfate (such as glucosamine 6-sulfate) for use in the treatment or prevent of undesirable angiogenesis or restenosis (for example after insertion of a stent).

In one embodiment there is provided a stent coated with a compound according to the present disclosure, in particular coated with a glycodendrimer comprising an amino sugar sulfate, such as glucosamine 6-sulfate.

In one embodiment there is provided a glycodendrimer according to the present disclosure or a composition comprising the same for use in the treatment or prophylaxis of gingivitis.

In one embodiment there is provided a glycodendrimer according to the present disclosure or a composition comprising the same for use in the treatment or prophylaxis of rheumatoid arthritis or osteoporosis.

In one embodiment glycodendrimers according to the present disclosure or pharmaceutical formulations thereof are suitable for administration directly to the eye as eye drops, by deposition of a pellet in or around the eye, or by injection into any chamber within the eye, or by direct infusion through an organ, for example at a concentration ranging from 2.5 to 2,500 µg/ml.

In one embodiment there is provided a method of treatment comprising administering a therapeutically effective amount of a glycodendrimer according to the present disclosure or a composition comprising same to a patient in need thereof, in particular for treatment or prophylaxis of an indication described herein.

In one embodiment there is provided use of a glycodendrimer or composition comprising the same for the manufacture of a medicament for the treatment of an indication described herein.

Process Chemistry for Zero Length Amide Bond Formation

The detailed divergent chemical synthesis of polypropyletherimine dendrimers cores up to generation 3 (i.e., with 16 peripheral carboxylic acid groups) has been described in detail in Krishna T R & Jayaraman N. Synthesis of poly (propyl ether imine) dendrimers and evaluation of their cytotoxic properties. J. Organic Chemistry 2003; 68(25): 9694-9704.

Starting with an oxygen core, the dendrimer was synthesised by repetitive cycles consisting of 2 red-uctions & 2 Michael addition reactions. These repetitive and consecutive reactions were performed using alpha-beta-unsaturated ester and nitrile as monomers, and supported metal catalysts and metal hydrides as reagents. Esters are converted to alcohols followed by conversion of alcohols to ethers with pendant nitriles, followed by conversion of nitriles to primary amines, followed by conversion of primary amines to tertiary amines with pendant esters. The procedure described is long but simple and the yield is good.

Chromatography after the sequential synthesis of each dendrimer generation by HPLC and/or column chromatograph can be used to ensure that the single entity generation 3 polypropyletherimine is obtained as a final product. A MALDI-MS of this molecule is shown in the supplementary files attached to the following paper:—Krishna T R & Jayaraman N. Synthesis of poly(propyl ether imine) dendrimers and evaluation of their cytotoxic properties. J. Organic Chemistry 2003; 68(25): 9694-9704.

Synthesis of large generation polypropyletherimine dendrimers is described in the following paper:—Jayamurugan G & Jayaraman N. Synthesis of large generation poly(propyl ether imine) dendrimers. Tetrahedron 2006; 62: 9582-9588.

A process to covalently link a biologically inactive glucosamine molecule to a biologically inactive anionic carboxylic acid terminated dendrimer molecule wherein the dendrimer core was reacted with the sugar molecule such as the glucosamine molecule in the presence of a coupling agent such as carbodiimide coupling or 1-ethyl-3-(3-dimethylaminopropyl) carbodiimide hydrochloride {EDC}. The reaction is carried out in an aqueous solvent, for example water and at room temperature and without an exogenous heat source. An analogous process is described for example in WO 03/089010. In one embodiment the core is a 3, 3.5 or 4 generation dendrimer.

This process had the advantage of comprising a single synthetic step to create a covalent zero length amide bond, using water as the solvent, & can be performed at room temp (i.e., 18-26° C.). This process also has the advantage that it avoided the need for the use of organic solvents that are often toxic in vivo.

Furthermore, organic solvents require additional, complicated and expensive purification procedures for isolating the final product from the organic solvent. Conjugation, that is to say, covalent linkage of the components in an aqueous environment facilitates the simple and straightforward purification of the final medicinal product. This has important industrial advantages, and manufacturing advantages, and regulatory advantages for a new pharmaceutical drug. This process was particularly useful for the preparation of anionic carboxylic acid terminated glycodendrimers including glycodendrimers comprising amino sugars other than glucosamine Sugars, for example glucosamine containing various combinations of sulfate moieties at the 3', 4' and 6' positions of the glucan moiety are also suitable for attachment using the same linkage chemistry.

Suitably, the dendrimers cores are covalently linked to compounds containing amino groups, for example, amine groups, for example, primary amine groups, such as amino sugars and sulphated sugars thereof, in particular glucosamine or sulphated glucosamine.

Suitably, the number of molecules of saccharide or sulfated saccharide covalently bound to the surface carboxylic acid groups is in a narrowly fixed proportion to the number of carboxylic acid groups present on the surface of the dendrimer. The number of amino sugars such as glucosamines, linked to the dendrimer, expressed as a percentage of the converted surface carboxylic groups is in the range, for example, from 1.5 to 30% such as 1.5 to 15%. More suitably, it is in the range from 6.25 to 15%, such as 12.5%.

Typically the covalent link formed by the conjugation is stable over a period of more than 18 months, which may be important in the shelf-life of a pharmaceutical product. In one embodiment the glycodendrimer formed is lyophilised. This may further extend the shelf life of the molecule.

Thus in one aspect there is provided a process preparing a glycodendrimer according to the present invention comprising the step of conjugating an amino sugar or amino sugar sulphate or a combination thereof to a dendrimer core, in particular a polypropyletherimine dendrimer core, for example prepared divergently, such as a generation 3 core. In one embodiment, a covalent zero length amide bond is formed between the sugar and a carboxylic acid residue on the core. In one embodiment a coupling agent is employed selected from 1-ethyl-3-(3-dimethylaminopropyl) carbodiimide hydrochloride and EDC.

In one embodiment the process employs water as the solvent. In one embodiment the reaction is carried out at less than 40° C. without the application of an external, additional energy source.

In one embodiment the glycodendrimer is purified after conjugation of the core to the sugar, for example purification may be effected by dialysis and/or by column chromatograghy.

In one embodiment the glycodendrimer obtained from said process is a molecule or population according to the inventions such as a monodispersion, for example with 2 glucosamine molecules attached at opposite ends of the surface of the dendrimer.

In one embodiment the disclosure relates to products obtainable from said process.

It is important to note that these anionic carboxylic acid terminated dendrimers (without glucosamine attached) have no effect on pro-inflammatory cytokines such as IL-6, 11-8, IL-1 beta, TNF-alpha and MIP-1 beta even at very high doses. It is also important to note that glucosamine (on its own) also has no effect on pro-inflammatory cytokines such as IL-6, IL-8, IL-1 beta, TNF-alpha and MIP-1 beta even at high doses.

Nevertheless, the present disclosure further provides use of the dendrimer cores (polypropyletherimine cores, particularly generation 3 cores), described herein in the preparation of a glycodendrimer, in particular a therapeutic glycodendrimer, in particular as described herein.

In one aspect there is provided use an amino sugar or amino sugar sulphate, in particular as described herein for the preparation of a glycodendrimer, in particular a therapeutic glycodendrimer, in particular as described herein.

Average as employed herein is intended to refer to a modal average or a mean average.

All citation and documents referred herein are specifically incorporated by reference.

Comprising in the context of the present invention means including.

Described above are embodiments comprising certain integers. Embodiments of the invention described above can be combined as technically appropriate. The present disclosure also extends to corresponding embodiments consisting of said integers as herein described.

All references to literature and patent documents are incorporated by reference.

EXAMPLES

The text below describes some of the compounds prepared and the molecular modelling studies undertaken over several years in the search for a biologically active dendrimer. A reference compound is a compound that is not a compound covered by the present disclosure.

Table 1 is a summary of the glycodendrimers prepared and analysed

| GLYCODENDRIMER | | | Biological Activity (reduction of pro-inflammatory cytokines) |
|---|---|---|---|
| Core | Generation | Sugar | |
| Triazine | 2 | Glucosamine (6 equivalents used) | none |
| Triazine | 2 | Glucosamine (12 equivalents used) | none |
| Triazine | 2 | Glucosamine (120 equivalents used) | none |
| Triazine | 2 | Glucosamine (120 equivalents used at pH 5) | none |
| Triazine | 3 | Glucosamine 50% loading | none |
| Triazine | 3 | Glucosamine 58% loading | none |
| Triazine | 3 | Glucosamine | none |
| PAMAM hybrid | 0.5 | 12.5% loading | |
| Triazine PAMAM hybrid | 3 1.5 | Glucosamine 18.75% loading | yes (but a mixture of multiple species of molecules that are not all closely related) |

Reference Compound 1 Generation 2 Triazine Dendrimers: Studies of Divergently Synthesised Anionic Generation 2 Carboxylic Acid Terminated (i.e., 12 Peripheral Carboxyl Groups) Triazine Dendrimers:

A generation 2 triazine dendrimer was synthesised as described previously in these papers:—Chouai A & Simanek E E. Kilogram-scale synthesis of a second-generation dendrimer based on 1,3,5-triazine using green and industrially compatible methods with a single chromatographic step. J. Organic Chemistry 2008; 73 (6): 2357-2366. Electrophoretic behaviour of anionic triazine and PAMAM dendrimers: methods for improving resolution and assessing purity using capillary electrophoresis. Lalwani S, Venditto V J, Chouai A, Rivera G E, Shaunak S, Simanek E E. Macromolecules 2009; 42: 3152-3161.; Mimicking PAMAM dendrimers with ampholytic, hybrid triazine dendrimers: a comparison of dispersity and stability. Lalwani S, Chouai A, Perez L M, Santiago V, Shaunak S, Simanek E E. Macromolecules 2009; 42: 6723-6732.; Simanek E E, Abdou H, Lalwani S, Lim J, Mintzer M, Venditto V J, Vittur B. The 8 year thicket of triazine dendrimers: strategies, targets and applications. Proc. R. Soc. A 2010; 466 (2117); 1445-1468. The dendrimer with 12 peripheral carboxylic acid groups was made by treatment of the amine terminated triazine dendrimer with succinic anhydride. Glucosamine was then covalently attached via an amide bond to its surface carboxylic acid groups. The molecule was then tested for:—(a) its cytotoxicity; and (b) its ability to reduce pro-inflammatory cytokine production by human monocytes and macrophages.

Cell cytotoxicity was determined as follows. Peripheral blood mononuclear (PBMN) cells were isolated from fresh human blood by density gradient centrifugation and re-suspended in growth medium (RPMI 1640, 20 mM L-glutamine, penicillin [250 IU/ml], streptomycin [250 µg/ml] and 10% endotoxin free human serum). The cells were then adhered to 14 cm plastic tissue culture plates for 1 h. The plates were washed, the adherent monocytes scraped with a cell scraper, and the cell density adjusted to $10^6$ cells/ml. 200 µL of these monocytes were plated in a 96 well plate at a density of $10^6$ cells/ml. The generation 2 dendrimer glucosamine (0 to 800 µg/ml) was added to monocytes and incubated for 24 h. Cell viability was assessed using the MTT assay.

The ability of this triazine based carboxylic acid terminated dendrimer glucosamine to reduce the production of a panel of pro-inflammatory cytokines was determined in a human monocyte/macrophage based assay. Lipopolysaccharide (LPS) was used to stimulate the release of pro-inflammatory cytokines. 1 ml aliquots of human monocytes ($10^6$ cells/ml) were transferred to a 24-well tissue culture plate and incubated for 30 min at 37° C. To these adherent monocytes, endotoxin free (i.e., <0.01 endotoxin units [EU]/ml) generation 2 carboxylic acid triazine terminated dendrimer glucosamine was added at concentrations from 50 to 200 µg/ml, and incubated for 1 h at 37° C. LPS (*Salmonella Minnesota*, Sigma. Catalogue number L9764) was added at 25 ng/ml. Positive controls were cells treated with LPS only. The negative controls were untreated cells, or cells treated with the dendrimer only. The cells were then maintained at 37° C. with 5% $CO_2$ for 3 h. Media was then removed, the cells lysed in 500 µL of Tri-reagent and (Sigma) and RNA extracted.

Reverse transcription for pro-inflammatory cytokine mRNA was performed in a 20 µL reaction mix with 200 to 400 ng of total RNA using a RNAeasy reverse transcription kit (Qiagen). Following reverse transcription, the reactions were diluted 1 in 4 with water and triplicate 2 µl aliquots were used for real-time PCR amplification of chemokine and cytokine mRNA. PCR amplification of IL-6, TNF-alpha, IL-8, MIP-1 beta and HPRT mRNA was performed using Jumpstart Sybr Green amplification mix (Sigma) in a Corbett 3000 Rotorgene. The cycle conditions were:—activation at 95° C. for 3 min, and 40 cycles of denaturation at 94° C. for 5 sec, annealing at 58° C. for 5 sec, extension at 72° C. for 8 sec, and fluorescence acquisition at 78 C and 81° C. for 5 sec. At the end of each PCR, a melting point acquisition from 72° C. to 95° C. was performed. For each gene, a standard curve was generated by serial 10-fold dilutions of a human cytokine quantification plasmid that incorporated all the cloned gene sequences of interest. The results were expressed as the absolute copy number of cytokine mRNA per 100,000 absolute copies of HPRT.

Reference Compound 1A—Synthesis 1:

A monodispersed generation 2 triazine dendrimer with 12 peripheral carboxylic acid groups was used. It had no cytotoxic effect up to the highest concentration tested and did not reduce the pro-inflammatory cytokines TNF-alpha or MIP-1 beta (FIG. 8).

Amidation reactions were performed using 6 equivalents of glucosamine per triazine dendrimer at pH 8. No cytotoxic effect of the generation 2 triazine dendrimer glucosamine was seen up to the highest concentration tested. No consistent dose related reduction in the pro-inflammatory cytokines TNF-alpha or MIP-1 beta was found. This dendrimer glucosamine did not possess the biological activity (i.e., reduction of pro-inflammatory cytokine production) required (FIG. 9).

Reference Compound 1B—Synthesis 2:

A monodispersed generation 2 triazine dendrimer with 12 peripheral carboxylic acid groups was used. Amidation reactions were performed using the increased amount of 12 equivalents of glucosamine per triazine dendrimer at pH 8. No cytotoxic effect of this generation 2 triazine dendrimer glucosamine was seen up to the highest concentration tested. No consistent dose related reduction in the pro-inflammatory cytokines TNF-alpha or MIP-1 beta was found. This dendrimer glucosamine did not possess the biological activity (i.e., reduction of pro-inflammatory cytokine production) required (FIG. 10).

Reference Compound 1C—Synthesis 3:

A monodispersed generation 2 triazine dendrimer with 12 peripheral carboxylic acid groups was used. Amidation reactions were performed using the greatly increased amount of 120 equivalents of glucosamine per triazine dendrimer at pH 8. No cytotoxic effect of this generation 2 triazine dendrimer glucosamine was seen up to the highest concentration tested. No consistent dose related reduction in the pro-inflammatory cytokines TNF-alpha or MIP-1 beta was found. This dendrimer glucosamine did not possess the biological activity (i.e., reduction of pro-inflammatory cytokine production) required (FIG. 11).

Reference Compound 1D—Synthesis 4:

A monodispersed generation 2 triazine dendrimer with 12 peripheral carboxylic acid groups was used. Amidation reactions were performed using 120 equivalents of glucosamine per triazine dendrimer but at pH 5 to:—(i) maximise the dendrimers surface loading with glucosamine; and (ii) reduce any side reactions. No cytotoxic effect of this generation 2 triazine dendrimer glucosamine was found up to the highest concentration tested. No consistent dose related reduction in the pro-inflammatory cytokines TNF-alpha or MIP-1 beta was found. This dendrimer glucosamine did not possess the biological activity (i.e., reduction of pro-inflammatory cytokine production) required (FIG. 12). We concluded that although we could synthesise a monodispersed generation 2 (i.e., with 12 peripheral carboxylic acid groups) triazine dendrimer glucosamine molecule that was not toxic, these molecules did not reduce pro-inflammatory cytokine production by LPS from monocytes and macrophages. This meant that the biological activity required of a monodispersed dendrimer glucosamine must be a function of:—(a) the functionalised peripheral glucosamines; (b) the dendrimer generation. We therefore proceeded to synthesise a generation 3 (i.e., with 24 peripheral carboxylic acid groups) triazine dendrimer glucosamine Reference Compounds 2 Generation 3 Triazine Dendrimers: Studies of Divergently Synthesised Generation 3 Anionic Carboxylic Acid Terminated (i.e., 24 Peripheral Carboxyl Groups) Triazine Dendrimers:

A monodispersed generation 3 triazine dendrimer was synthesised as described previously [by Crampton et al 2007]. The dendrimer with 24 peripheral carboxylic acid groups was made by treatment of the amine terminated triazine dendrimer with succinic anhydride. Glucosamine was covalently attached to the surface carboxylic acid groups. The molecule was then tested for:—(a) its cytotoxicity; (b) its ability to reduce pro-inflammatory cytokine production.

The molecules cytotoxicity was determined as follows. Peripheral blood mononuclear (PBMN) cells were isolated from fresh human blood by density gradient centrifugation and re-suspended in growth medium (RPMI 1640, 20 mM L-glutamine, penicillin [250 IU/ml], streptomycin [250 μg/ml] and 10% endotoxin free human serum). They were allowed to adhere to 14 cm plastic tissue culture plates for 1 h. The plates were washed, and the adherent monocytes scraped with a cell scraper, and the cell density adjusted to $10^6$ cells/ml. 200 μL of these monocytes were plated in a 96 well plate at a density of $10^6$ cells/ml. The generation 3 dendrimer glucosamine (0 to 400 μg/ml) was then added to monocytes and incubated for 24 h. Cell viability was assessed using the MTT assay.

The ability of this triazine based glycosylated dendrimer to reduce the production of a panel of pro-inflammatory cytokines was determined in a human monocyte/macrophage based assay with LPS being used to stimulate the release of pro-inflammatory cytokines. 1 ml aliquots of human monocytes ($10^6$ cells/ml) were transferred to a 24-well tissue culture plate and incubated for 30 min at 37° C. To these adherent monocytes, endotoxin free (i.e., <0.01 EU/ml) triazine generation 3 carboxylic acid terminated dendrimer glucosamine was added at concentrations from 50 to 200 μg/ml and incubated for 1 h at 37° C. LPS (*Salmonella Minnesota*, Sigma. Catalogue number L9764) was added at 25 ng/ml. Positive controls were cells treated with LPS only, and the negative controls were untreated cells, or untreated cells and the dendrimer only. The cells were then maintained at 37° C. with 5% $CO_2$ for 3 h. Media was then removed, cells lysed in 500 μL of Tri-reagent (Sigma) and RNA extracted. Reverse transcription was performed using a Qiagen RT kit. Aliquots of cDNA were then subjected to quantitative real-time PCR for TNF-alpha and MIP-1 beta.

Reference Compound 2A—Synthesis 5:

A monodispersed generation 3 anionic triazine dendrimer with 24 peripheral carboxylic acid groups was used. It was not cytotoxic and no reduction in IL-6, TNF-alpha, IL-8 or MIP-1 beta was found (FIG. 13).

Amidation reactions were then performed with glucosamine that led to a peripheral loading of the dendrimer surface with 12 glucosamines (i.e., 50% loading of the peripheral carboxylic acid groups available). No cytotoxic effect was noted of this monodispersed generation 3 carboxylic acid terminated triazine dendrimer glucosamine up to the highest concentration tested. No consistent dose related reduction in IL-6, TNF-alpha, IL-8 or MIP-1 beta was found. This dendrimer did not possess the biological activity (i.e., reduction of pro-inflammatory cytokine production) required (FIG. 14).

Reference Compound 2B—Synthesis 6:

A monodispersed generation 3 triazine dendrimer with 24 peripheral carboxylic acid groups was used. Amidation reactions were performed with glucosamine that led to a peripheral loading of the dendrimer surface with 14 glucosamine (i.e., 58% loading of the peripheral carboxylic acid groups available). No cytotoxic effect was noted of this monodispersed generation 3 triazine dendrimer glucosamine up to the highest concentration tested. No reduction in IL-6, TNF-alpha, IL-8 or MIP-1 beta was found. This dendrimer did not possess the biological activity (i.e., reduction of pro-inflammatory cytokine production) required (FIG. 15).

In conclusion, we found that although we could synthesise a monodispersed generation 2 (i.e., with 12 peripheral carboxylic acid groups) and a monodispersed generation 3 (i.e., with 24 peripheral carboxylic acid groups) triazine dendrimer glucosamine with a sufficient percentage of glucosamine, these monodispersed molecules did not have the biological activity required (i.e., they did not reduce pro-inflammatory cytokine production).

We therefore concluded that the biological activity required of the dendrimer glucosamine must be a function of:—(a) the functionalised peripheral glucosamines; (b) the dendrimer generation; (c) an absolute requirement for a peripheral coat of PAMAM based chemistry on the surface of the dendrimer itself—based upon the previous work of Shaunak using PAMAM based dendrimer glucosamine which was found to reduce pro-inflammatory cytokine production (Shaunak S, Thomas S, Gianasi E, Godwin A, Jones E, Teo I, Mireskandari K, Luthert P, Duncan R, Patterson S, Khaw P & Brocchini S Polyvalent dendrimer glucosamine conjugates prevent scar tissue formation. Nature Biotechnology 2004; 22: 977-985). We therefore proceeded to further synthetic studies in which a hybrid triazine PAMAM dendrimer glucosamine with peripheral carboxylic acid groups was made.

As the generation 2 triazine dendrimer is devoid of any structural chemical imperfections, and it can be made as a mondispersed molecule at the kilogram scale with ease (Chouai A & Simanek E E. Kilogram-scale synthesis of a second-generation dendrimer based on 1,3,5-triazine using green and industrially compatible methods with a single chromatographic step. J. Organic Chemistry 2008; 73(6): 2357-2366), we proceeded to make the triazine PAMAM hybrid molecules using the generation 2 triazine dendrimer as the starting molecule. A synthetic strategy for making hybrid dendrimers with a triazine inner core and a PAMAM outer shell was therefore devised.

Reference Compounds 3 Triazine and Pamam Hybrid Dendrimers:

Studies of Divergently Synthesised Generation 2 Anionic Triazine Dendrimers with an Outer Shell of carboxylic acid terminated generation 0.5 PAMAM to which glucosamine is covalently attached:

Reference Compound 3A—Synthesis 7:

A divergent synthetic approach was used to make generation 2 anionic triazine dendrimers incorporating an outer shell of generation 0.5 PAMAM as previously described (Electrophoretic behaviour of anionic triazine and PAMAM dendrimers: methods for improving resolution and assessing purity using capillary electrophoresis. Lalwani S, Venditto V J, Chouai A, Rivera G E, Shaunak S, Simanek E E. Macromolecules 2009; 42: 3152-3161.; Mimicking PAMAM dendrimers with ampholytic, hybrid triazine dendrimers: a comparison of dispersity and stability. Lalwani S, Chouai A, Perez L M, Santiago V, Shaunak S, Simanek E E. Macromolecules 2009; 42: 6723-6732). The hybrid dendrimer (152 mg) was then solubilised in double deionised water (1.5 ml) and the pH reduced with hydrochloric acid (HCl) in order to transform the surface groups from the nonreactive sodium carboxylated ($COO^-Na^+$) to the reactive carboxylic acid ($COO^-H^+$). This hybrid dendrimer contained 24 reactive COOH groups. 200 mg of glucosamine hydrochloride was solubilised in double deionised water (4 ml), the pH adjusted to pH 5, and it was added to the dendrimer solution. The pH was maintained at pH 5 with HCl during the reaction. The condensing agent EDC (279 mg) was solubilised in water (5.6 ml) and added to the reaction solution. The mixture was stirred at room temperature. Notably, the reaction took place at ambient room temperature and did not require the application of an external energy source. After 3 h of stirring, the reaction mixture was purified by transfer to a dialysis cassette followed by 18 h of dialysis in endotoxin free water at 4° C. with 4 changes of water. This led to the removal of the unreacted glucosamine, the excess EDC, and the N-acyl isourea formed during the reaction. The final product was freeze-dried. MALDI-MS and 1H and 13NMR analysis showed that there were 3 glucosamine molecules on each hybrid triazine-PAMAM dendrimer molecule, giving a glucosamine percentage loading of 12.5%.

The molecules cytotoxicity was determined as follows. Peripheral blood mononuclear (PBMN) cells were isolated from fresh human blood by density gradient centrifugation and re-suspended in growth medium (RPMI 1640, 20 mM L-glutamine, penicillin [250 IU/ml], streptomycin [250 µg/ml] and 10% endotoxin free human serum). They monocytes were allowed to adhere to 14 cm plastic tissue culture plates for 1 h. The plates were washed, the adherent monocytes scraped with a cell scraper, and the cell density adjusted to $10^6$ cells/ml. 200 µL of these monocytes were plated in a 96 well plate at a density of $10^6$ cells/ml. The hybrid generation 2 triazine generation 0.5 PAMAM dendrimer glucosamine (0 to 400 ug/ml) was then added to the monocytes and incubated for 24 h. Cell viability was assessed using the MTT assay.

No cytotoxic effect was noted with this divergently synthesised hybrid generation 2 triazine generation 0.5 PAMAM dendrimer glucosamine with peripheral carboxylic acid groups up to the highest concentration tested (FIG. 16).

The ability of this triazine based dendrimer glucosamine with peripheral carboxylic acid groups to reduce the production of a panel of pro-inflammatory cytokines was determined in a human monocyte/macrophage based assay with LPS being used to stimulate the release of pro-inflammatory cytokines. 1 ml aliquots of human monocytes ($10^6$ cells/ml) were transferred to a 24-well tissue culture plate and incubated for 30 min at 37° C. To these adherent monocytes, endotoxin free (i.e., <0.01 EU/ml) generation 2 triazine generation 0.5 PAMAM dendrimer glucosamine was added at concentrations from 50 to 200 µg/ml and incubated for 1 h at 37° C. LPS (*Salmonella Minnesota*, Sigma. Catalogue number L9764) was added at 25 ng/ml. Positive controls were cells treated with LPS only, and the negative controls were untreated cells, or untreated cells and the dendrimer only. The cells were then maintained at 37° C. with 5% $CO_2$ for 3 h. Media was then removed, cells lysed in 500 µL of Tri-reagent (Sigma) and RNA extracted. Reverse transcription was performed using a Qiagen RT kit. Aliquots of cDNA were then subjected to quantitative real-time PCR for IL-6, TNF-alpha, IL-8 and MIP-1 beta.

No consistent dose related reduction in the pro-inflammatory cytokines IL-6, TNF-alpha, IL-8 or MIP-1 beta was found. This hybrid generation 2 triazine generation 0.5 PAMAM dendrimer glucosamine with peripheral carboxylic acid groups did not possess the biological activity (i.e., reduction of pro-inflammatory cytokine production) required even though its percentage surface loading of glucosamine of 12.5% was the same as that of the generation 3.5 PAMAM dendrimer glucosamine molecule which could reduce pro-inflammatory cytokine production (FIG. 16).

We therefore concluded that the biological activity required of the dendrimer glucosamine must be a function of:—(a) the functionalised peripheral glucosamines; (b) an absolute requirement for a larger peripheral coat of PAMAM based chemistry on the surface of the dendrimer itself; and (c) a larger generation size of the dendrimer. We therefore proceeded to further synthetic studies in which another hybrid triazine PAMAM dendrimer glucosamine molecule with a second layer of PAMAM was made and tested.

Reference Compound 3B—Synthesis 8:

A generation 2 triazine anionic dendrimer incorporating an outer shell of generation 1.5 PAMAM was synthesised by the divergent approach as previously described (Chouai A & Simanek E E. Kilogram-scale synthesis of a second-generation dendrimer based on 1,3,5-triazine using green and industrially compatible methods with a single chromatographic step. J. Organic Chemistry 2008; 73(6): 2357-2366). A known amount of the dendrimer (100 mg) was then solubilised in double deionised water (1 ml) and the pH reduced with hydrochloric acid (HCl) in order to transform the surface groups from the nonreactive sodium carboxylated ($COO^-Na^+$) to the reactive carboxylic acid ($COO^-H^+$). This dendrimer contained 48 carboxylic acid groups. A known amount of glucosamine hydrochloride (100 mg) was solubilised in double deionised water (2 ml), the pH adjusted to pH 5, and it was then added to the dendrimer solution. The pH was maintained at pH 5 with HCl. 260 mg of the condensing agent EDC was solubilised in water (5.2 ml) and added to the reaction solution. The reaction mixture was stirred at room temperature. Notably, the reaction can take place at ambient room temperature and does not require the application of an external energy source. After 3 h of stirring, the reaction mixture was purified by transfer to a dialysis cassette followed by 18 h of dialysis in endotoxin free water at 4° C. with 4 changes of water. This led to the removal of the unreacted glucosamine, the excess EDC, and the N-acyl isourea formed during the reaction. The final product was freeze-dried. Capillary electrophoresis, MALDI-MS and 1H and 13NMR analysis of the final product showed that there were 9 glucosamine molecules on each hybrid generation 2 triazine generation 1.5 PAMAM dendrimer glucosamine with peripheral carboxylic groups, giving a percentage glucosamine loading of 18.75%. The freeze-dried product was stored in the dark and under airtight conditions.

Endotoxin was removed from the compound using a column packed with polymixin B beads. Endotoxin levels were then determined using a limulus amebocyte lysate assay. All of the biological data described below was obtained with compounds whose endotoxin level was <0.1 EU/ml.

No cytotoxic effect was noted with this hybrid generation 2 triazine generation 1.5 PAMAM carboxylic acid terminated dendrimer glucosamine up to the highest concentration tested (FIG. 17).

A large reduction in the pro-inflammatory cytokines IL-6, TNF-alpha, IL-8 or MIP-1 beta was found in the presence of this hybrid generation 2 triazine generation 1.5 PAMAM carboxylic acid terminated dendrimer glucosamine at a concentration of 100 µg/ml (FIG. 17).

Although we had now established that a divergently synthesised hybrid generation 2 triazine generation 1.5 PAMAM carboxylic acid terminated dendrimer glucosamine with 9 surface glucosamines had the biological activity required, and that it was not toxic, its analytical chemistry analysis (capillary electrophoresis, MALDI-MS & NMR) showed that it was a mixture of several closely related molecules. This meant that it would not be suitable for pharmaceutical applications.

As a result of our multiple failures to divergently synthesise a monodispersed carboxylic acid terminated dendrimer glucosamine with the desired biological activities, we undertook detailed molecular modelling studies of the biologically active molecules and compared them with the biologically inactive molecules. Our aim was to define the key chemical characteristics (e.g., size, shape, density, flexibility of the core of the dendrimer, flexibility of the periphery of the dendrimer, surface charge distribution, hydophobicity, hydrophilicity, surface glucosamine loading) that would be necessary to synthesise a monodispersed dendrimer glucosamine with peripheral carboxylic acid groups that would:—(a) not be toxic; (b) reduce pro-inflammatory cytokine production by LPS from monocytes and macrophages and dendritic cells; (c) be the smallest size overall size of dendrimer glucosamine molecule that would not be cytotoxic but would reduce pro-inflammatory cytokines; (d) be suitable as a pharmaceutical drug.

Modelling Studies

C. W von der Leith (2002) undertook a detailed geometric and conformational analysis of 15 glycodendrimers with regard to their core moieties, spacer characteristics, and the type of terminal carbohydrate unit (Von der Lieth-W, Frank M, Lindhorst T K. Molecular dynamics simulations of glycoclusters and glycodendrimers. Reviews in Molecular Biotechnology 2002; 90: 311-337). They showed that the accessible conformational space depended strongly upon:— (1) the structural features of the core dendrimer; (2) its spacer moieties; (3) the type of terminating sugars. They also concluded that the shape of smaller glycodendrimers is controlled by the chemical constitution of the spacer groups and the geometry of the core structure. In contrast, with increasing numbers of terminating sugar units, the interaction of the latter is increasingly determined by the shape of the accessed conformational space. Furthermore, the conformational behaviour of the clusters containing aromatic substructures in the spacer part of the molecule is different to that of those that do not exhibit aromatic substructures.

The inclusion of explicit solvent molecules in the molecular dynamics simulations is absolutely necessary to produce realistic 3-dimensional structures of glycodendrimers. A comparison of PAMAM based glycodendrimers with other sugar based glycodendrimers also makes it clear that the geometry of the core is an important determinant of the overall shape of the accessible conformational space (Barata T S, Shaunak S, Teo I, Zloh M, Brocchini S. Structural studies of biologically active glycosylated polyamidoamine (PAMAM) dendrimers. J Mol Model. Epub ahead of print: doi 10.1007/x00894-010-0907-1; Barata T S, Brocchini S, Teo I, Shaunak S, Zloh M. From sequence to 3D structure of hyperbranched molecules: application to surface modified PAMAM dendrimers. J Mol Model. Epub ahead of print: doi 10.1007/s00894-011-0966-y Barata T S, Teo I, Brocchini S, Zloh M, Shaunak S. Partially glycosylated dendrimers block MD-2 and prevent TLR4-MD-2-LPS complex mediated cytokine responses. PLoS Comput Biol 2011; 7(6): e1002095. doi:10.1371/journal.pcbi.1002095).

Although glycodendrimers are almost always designed with long spacers arms, it is desirable to reduce the flexibility of these spacers considerably (by reducing their length) because only those ligands that fulfil exactly the geometric requirements of a multivalent receptor will increase the binding affinity of the receptor-ligand interaction (Von der Lieth-W, Frank M, Lindhorst T K. Molecular dynamics simulations of glycoclusters and glycodendrimers. Reviews in Molecular Biotechnology 2002; 90: 311-337).

Differences in flexibility and conformation were investigated by determining each molecule's Root Mean Square Deviations (RMSD) along the trajectory of a 2 ns molecular dynamic simulation with implicit solvent. A profile with high RMSD values means that the molecule is flexible and that it is constantly changing its conformation during the course of the simulation. The modelled dendrimer glucosamine structures exhibited varying degrees of flexibility. The dendrimer surface properties analysis along the trajectory of a 2 ns molecular dynamic simulation with implicit solvent showed that the RMSD of the biologically active generation 3.5 PAMAM anionic dendrimer glucosamine (17 Angstroms (A)) and the biologically active hybrid generation 2 triazine generation 1.5 PAMAM dendrimer glucosamine (12 A) were similar. These RMSD values were considerably greater than those of the biologically inactive generation 3 anionic triazine dendrimer glucosamine (7 A) and the hybrid generation 2 anionic triazine generation 0.5 PAMAM dendrimer glucosamine (7 A). Similar observations applied to studies of their surface area; PAMAM generation 3.5 dendrimer glucosamine (11,500 square Angstroms ($A^2$)); hybrid generation 2 triazine generation 1.5

PAMAM dendrimer glucosamine (9,000 A$^2$); triazine generation 3 glucosamine (4,000 A$^2$); hybrid generation 2 triazine generation 0.5 PAMAM dendrimer glucosamine (4,000 A$^2$). Similar observations applied to studies of their polar surface area; PAMAM generation 3.5 dendrimer glucosamine (8,000 A$^2$); hybrid generation 2 triazine generation 1.5 PAMAM dendrimer glucosamine (6,000 A$^2$); triazine generation 3 glucosamine (2,500 A$^2$); hybrid generation 2 triazine generation 0.5 PAMAM dendrimer glucosamine (2,500 A$^2$). Modelling of the hydrophilic and hydrophobic surfaces of the PAMAM dendrimer glucosamine, triazine dendrimer glucosamine and the hybrid triazine PAMAM dendrimer glucosamine molecules was also undertaken (FIGS. 18 to 29). The surface of PAMAM generation 3.5 dendrimer glucosamine was mainly hydrophilic (FIG. 21). The biologically inactive hybrid triazine PAMAM dendrimer glucosamine molecules were found to have multiple exposed hydrophobic surfaces. These observations led us to the conclusion that surface hydrophilicity of dendrimer glucosamine was an important property for the dendrimer glucosamine's partial antagonist activity for the LPS-MD2-TLR4 cell surface receptor complex. These modeling studies enabled us to define the relative contribution of surface hydrophilicity towards making the smallest and simplest dendrimer glucosamine molecule that would be biologically active; i.e., it would reduce proinflammatory cytokine responses.

The Frontier Molecular Orbital Theory was also used because it postulates that observation of the interaction between the HOMO (highest occupied molecular orbital) and LUMO (lowest unoccupied molecular orbital) of the reactants provides a good approximation to reactivity. Thus, the direction of the reaction should be towards the larger overlap between the HOMO and LUMO orbitals. It was found that when one glucosamine molecule was present, the HOMO was always located in the diametrically opposite branch of the dendrimer. This means that the first and most energetically favourable dendrimer glucosamine molecule that will form will have 4 glucosamine molecules equally distributed on the surface of the dendrimer. This will be rapidly followed by the formation of a dendrimer glucosamine molecule that will have 8 glucosamine molecules equally distributed on the surface of the dendrimer. Taking both electronic and steric effects into account, the addition of eight glucosamine molecules onto the Generation 3.5 PAMAM dendrimer was found to be the most energetically and sterically favourable molecule that would be formed. This molecular modelling observation was consistent with the analytical chemistry (i.e., experimental observation) that 8 glucosamine molecules were present on the surface of the dendrimer.

Figure 30:
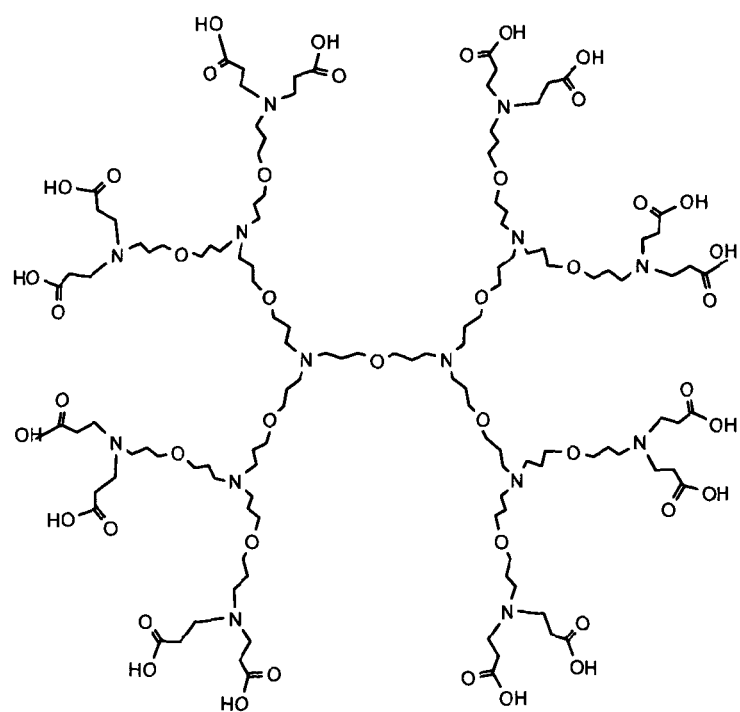

Modelling Studies of a Low Generation Polypropyletherimine Dendrimer Glucosamine Molecule Based on the theory proposed above the oxygen core generation 3 polypropyletherimine dendrimer was the smallest polypropyletherimine dendrimer that could possibly be glycosylated with 2 glucosamine residues using the EDC based conjugation method described (FIGS. 30 and 31). Molecular modelling studies were therefore carried out to determine whether it would have the key chemical characteristics (e.g., size, shape, density, flexibility of the core of the dendrimer, flexibility of the periphery of the dendrimer, surface charge distribution, hydrophilicity, surface glucosamine loading) that would be necessary for it to reduce pro-inflammatory cytokine production by LPS from monocytes and macrophages and dendritic cells.

Firstly, these modelling studies showed that the polypropyletherimine dendrimer glucosamine was structurally very different to either the PAMAM dendrimer glucosamine or the triazine dendrimer glucosamine, or the hybrid triazine PAMAM dendrimer glucosamine. Secondly, they showed that the polypropyletherimine dendrimer glucosamine was a simple molecular structure. Thirdly, they showed that the surface of the polypropyletherimine dendrimer glucosamine was completely hydrophilic. The important conclusion from these molecular modelling studies was that there was no steric hindrance in the vicinity of the core of the polypropyletherimine dendrimer. This observation was in contrast to the observations made with the triazine dendrimer glucosamine and the hybrid generation 2 triazine generation 0.5 PAMAM dendrimer glucosamine.

Figure 32:
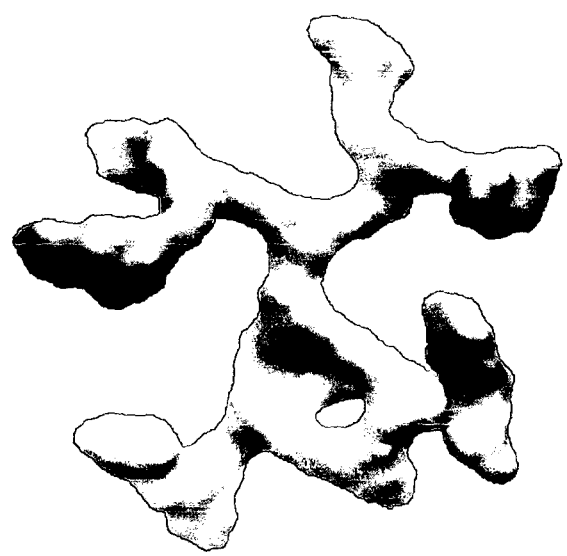
Figure 33:
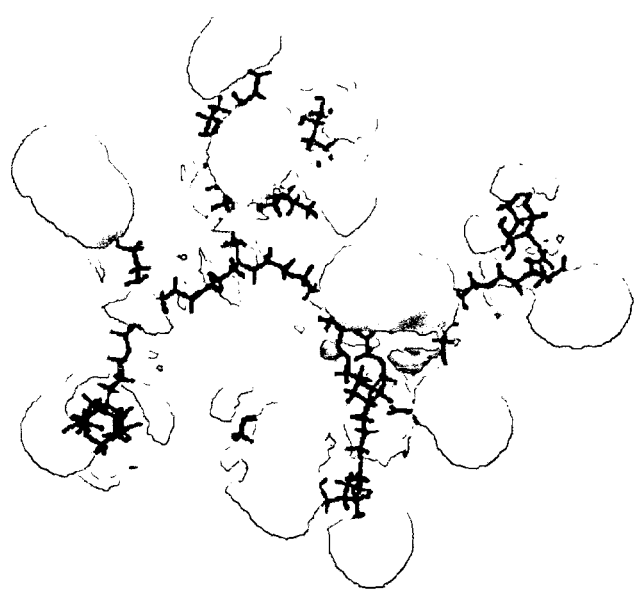

The polypropyletherimine dendrimer glucosamine surface property analysis along the trajectory of a 2 ns molecular dynamic simulation with implicit solvent showed that its Route Mean Square Deviation (RMSD) was 12 A. This made it very similar to the biologically active hybrid generation 2 triazine generation 1.5 PAMAM dendrimer glucosamine (12 A). This reflected the much less compact nature of the core of the polypropyletherimine dendrimer compared to the PAMAM dendrimer or the triazine dendrimer. This enabled the polypropyletherimine dendrimer to be a much more flexible molecule. In addition, all its peripheral groups face outwards because the absence of a hydrophobic core means that there is no steric hinderence of the peripheral carboxylic acid groups (FIGS. 32 and 33).

The surface area of the polypropyletherimine dendrimer glucosamine was much smaller than expected at only 3000 square Angstroms. This compared unfavourably with the two biologically active dendrimer glucosamine molecules that had already been studied; PAMAM generation 3.5 dendrimer glucosamine (11,500 A$^2$, and the hybrid generation 2 triazine generation 1.5 PAMAM dendrimer glucosamine (9,000 A$^2$). This result suggested that in terms of flexibility and conformation, the generation 3 anionic carboxylic acid terminated (with 16 carboxylic acid groups) dendrimer glucosamine (12.5% loading) would not demonstrate the biological properties required for reducing proinflammatory cytokine production.

Example 1

Studies of Generation 3 Polypropyletherimine Carboxylic Acid Terminated Dendrimer Glucosamine Example 1A Synthesis 9

Despite the molecular modelling studies showing that the generation 3 polypropyletherimine carboxylic acid terminated dendrimer glucosamine (12.5% loading) would not be biologically active, we nevertheless proceeded with its chemical synthesis and its biological testing. Divergent synthesis of a generation 3 carboxylic acid terminated polypropyletherimine dendrimer has been previously described by Krishna T R & Jayaraman N. Synthesis of poly(propyl ether imine) dendrimers and evaluation of their cytotoxic properties. J. Organic Chemistry 2003; 68(25): 9694-9704.

50 mg of a monodispersed generation 3 polypropyletherimine dendrimer (MWt 2,667) was dissolved in 0.5 ml water. 50 mg of glucosamine was dissolved in 1 mg/ml water, added to the dendrimer, and the pH adjusted to pH 5. EDC (208 mg) was dissolved in 4.1 ml of water and added to the mixture, and the pH adjusted to 5.0. The reaction was stirred for 3 h at room temperature with constant monitoring of the pH which was adjusted to pH 5.0. After 3 h, the reaction was transferred to a 2,000 MWt cut-off dialysis cassette and then dialysed for 24 h with 3 changes of water. All of the water used in the synthesis reactions and in the dialysis was endotoxin free. The dialysed reactions were lyophilised and resuspended in water at 50 mg/ml, and confirmed to be endotoxin free at <0.1 EU/ml using the limulus assay.

MALDI-MS and NMR studies showed that the monodispersed generation 3 polypropyletherimine dendrimer (with 16 peripheral carboxylic acid groups) had a loading of 2 glucosamine molecules per dendrimer (actual MWt 3,061; theoretical calculated weight 3,061). This gave a percentage glucosamine loading of 12.5%; i.e. 2 glucosamine molecules on the 16 peripheral carboxylic acid groups of this dendrimer.

Example 1B

Alternative Process

To prepare endotoxin-free solutions and glassware, all glassware and magnetic fleas were autoclaved twice at 123° C. for 15 minutes. The synthesis was performed using sterile and endotoxin free disposable plastic tissue culture grade 50 ml universal tubes. All other disposable plastic pipettes, universals and syringes are certified endotoxin-free (i.e., endotoxin <0.01 endotoxin units (EU)/ml). Endotoxin free water for injection was used. This means that endotoxin contamination was reduced to a minimum from the very start of the partial glycosylation synthesis reaction. In order to eliminate any bacterial contamination of the pH probe used, it was first immersed in 1 N HCl solution for 15 minutes before being used, and then washed 4 times with endotoxin free water to remove any residual acid.

150 mg of the Generation 3 polypropyletherimine dendrimer was dissolved in 1.5 ml sterile endotoxin free water to give a concentration of 100 mg/ml. A magnetic flea was put into the 50 ml Falcon tube and stirred at a slow speed on a magnetic stirring plate. 150 mg of D-glucosamine hydrochloride from Sigma UK (catalogue number G4875) was dissolved in 3 ml of sterile water to give a concentration of 50 mg/ml. It was then added to the dissolved dendrimer. This was equivalent to 0.78 glucosamine molecules per peripheral carboxylic acid group on the dendrimer. The pH of the resulting solution (which is quite acidic) was readjusted to 5.0 using 1 N NaOH. Then, 334 mg of 1-ethyl-3-3-dimethylaminopropyl carboiimide hydrochloride (EDCI, Sigma UK) was dissolved in 6.7 ml sterile water to give a concentration of 50 mg/ml. This was equivalent to 1.94 EDCI molecules per peripheral carboxylic acid group on the dendrimer. The EDCI solution was then added immediately to the solution containing the dendrimer and the glucosamine. The pH was readjusted to 5.0 with 1 N HCl. The pH of the reaction solution was readjusted to 5.0 by adding 1 N HCl every 15-30 minutes during the 3 hour reaction. The final volume of the reaction was about 12-12.5 ml.

For the dialysis steps that followed, all glass beakers and magnetic stir bars were autoclaved twice at 123° C. for 15 minutes. Endotoxin free water (Baxter Healthcare) was used. One of two procedures was followed. The first procedure used a Float-a-Lyzer dialysis cassette (Spectrapor) with a MWt cut-off of 1 kDa and a volume of 10 ml. In this case, the dialysis tube was rehydrated using endotoxin-free water, filled with the solution, and then dialysed (with stirring) for 1 hour in 1 L of endotoxin free water at 4° C. All subsequent dialysis was at 4° C. The water was then replaced and the dialysis continued overnight. The following day, the water was replaced and the dialysis continued for another 24 hours; i.e., a further 4 changes of water at 3.5 h intervals, and including another overnight dialysis. In total, this meant 42 hours of dialysis at 4° C. with 7 changes of water. In the second dialysis procedure, a Slide-a-lyser dialysis cassette (Pierce) with a MWt cut-off of 2 kDa and a volume of 3-12 ml was used. The dialysis cassette was rehydrated using endotoxin-free water, filled with the solution, and then dialysed (with stirring) for 1 hour in 1 L of endotoxin free water at 4° C. All subsequent dialysis was at 4° C. The water was then replaced and the dialysis continued overnight. The following day, the water was replaced and the dialysis continued for another 24 hours, with a further 4 changes of water at 3.5 hour intervals, and including another overnight dialysis. In total, this meant 42 hours of dialysis at 4° C. with 7 changes of water. The dialysate was then removed from the cassettes with a needle and syringe and filtered through 0.2 μm sterile filters and placed in pre-weighed sterile 50 ml Falcon tubes. It was then frozen for at least 1 hour at −80° C. Parafilm was placed over the mouth of the 50 ml tube that contained the frozen dendrimer glucosamine and pierced with a needle. The tube was then placed in a freeze drier (which has been pre-run for 30 min) and its contents left to lyophilize for 48 hours.

The lyophilised product was confirmed to be endotoxin free at <0.1 EU/ml using the limulus amoebocyte assay. As the dendrimer glucosamine is hygroscopic, it was stored in small airtight containers, and under argon, and at 4° C., and wrapped in aluminium foil. H-NMR and C-NMR and MALDI-MS studies showed that the Generation 3 polypropyletherimine dendrimer (with 16 peripheral carboxylic acid groups) had a loading of 2 glucosamine molecules per dendrimer. This gave a percentage glucosamine loading of 12.5%; i.e., 2 glucosamine molecules on the 16 peripheral carboxylic acid groups of this dendrimer. In addition, there was no residual small molecule contamination of the product with acrylonitrile, acrylic acid, free glucosamine or urea.

Example 2

Biological Studies with the Generation 3 Polypropyletherimine Carboxylic Acid Terminated Dendrimer Glucosamine Example 2A Cellular cytotoxicity was determined as follows. Peripheral blood mononuclear cells were isolated from fresh human blood by density gradient centrifugation and re-suspended in growth medium (RPMI 1640, 20 mM L-glutamine, penicillin [250 IU/ml], streptomycin [250 μg/ml] and 10% endotoxin free human serum). They were allowed to adhere to plastic tissue culture plates for 1 h. The plates were washed, the adherent monocytes scraped with a cell scraper, and the cell density adjusted to $10^6$ cells/ml. 200 μL of these monocytes were plated in a 96 well plate at a density of $10^6$ cells/ml. The generation 3 polypropyletherimine dendrimer (0 to 400 μg/ml) was added to monocytes and incubated for 24 h. Cell viability was assessed using the MTT assay. No cytotoxic effect of the generation 3 polypropyletherimine carboxylic acid terminated dendrimer was found up to the highest concentration tested. The generation 3 polypropyletherimine dendrimer glucosamine (0 to 400 µL/ml) was then added to monocytes and incubated for 24 h. Cell viability was assessed using the MTT assay. No cytotoxic effect of the generation 3 polypropyletherimine carboxylic acid terminated dendrimer glucosamine was found up to the highest concentration tested (FIG. 34).

Example 2B

The Ability of the Generation 3 Polypropyletherimine Dendrimer Glucosamine to Reduce Pro-Inflammatory Cytokine Production was Determined in a Human Monocyte/Macrophage Based Assay with LPS being Used to Stimulate the Release of Pro-Inflammatory Cytokines 1 ml aliquots of human monocytes ($10^6$ cells/ml) were transferred to a 24-well tissue culture plate and incubated for 30 min at 37° C. To these adherent monocytes, endotoxin free (i.e., <0.01 EU/ml) generation 3 polypropyletherimine carboxylic acid terminated dendrimer glucosamine was added at concentrations from 50 to 200 µg/ml and incubated for 1 h at 37° C. LPS (*Salmonella Minnesota*, Sigma. Catalogue number L9764) was added at 25 ng/ml. Positive controls were cells treated with LPS only, and the negative controls were untreated cells, or cells incubated with the dendrimer only. The cells were then maintained at 37° C. with 5% $CO_2$ for 3 h. Media was then removed, cells lysed in 500 µL of Tri-reagent (Sigma) and RNA extracted. Reverse transcription was performed using a Qiagen RT kit. Aliquots of cDNA were then subjected to quantitative real-time PCR for a panel of cytokines. A large reduction in the synthesis of the pro-inflammatory cytokines IL-6, TNF-alpha, IL-8, and MIP-1 beta was seen in the presence of the generation 3 anionic polypropyletherimine carboxylic acid terminated dendrimer glucosamine at a concentration of 100 µg/ml. In addition, no change was seen in the anti-inflammatory cytokines IL-10 and interferon-beta (FIGS. 34 and 35). This was a very surprising and unexpected biological result.

Example 2C

Detailed Biological Studies with the Generation 3 Polypropyletherimine Carboxylic Acid Terminated Dendrimer Glucosamine The reduction in the production of the pro-inflammatory cytokines IL-6, TNF-alpha, IL-8 and MIP-1 beta seen with generation 3 polypropyletherimine carboxylic acid terminated dendrimer glucosamine at a dose of 100 µg/ml with *Salmonella* sp. LPS was a surprising result because all of our molecular modelling studies had suggested that the generation 3 polypropyletherimine dendrimer glucosamine (with only 16 carboxylic acids available for the conjugation to glucosamine) would:—(1) be too small a molecule; (2) it would not have the correct physic-chemcial characteristics to act as an effective antagonist of the MD2-TLR4-LPS mediated pro-inflammatory cytokine response. To further verify the validity of the biological results obtained above with the generation 3 polypropyletherimine carboxylic acid terminated dendrimer glucosamine, additional biological experiments were performed.

Example 2D

Assay for Inhibition of Pro-Inflammatory Cytokine Production by Generation 3 Polypropyletherimine Carboxylic Acid Terminated Dendrimer Glucosamine after Challenge with *Shigella* Sp. Wild Type LPS and Molecularly Modified waaL Mutant *Shigella* Sp. LPS Wild type M90 and the *Shigella* mutant (waaL—which has no O-antigen glucosylation pattern—see FIG. 36 and also West N P, Sansonetti P, Mounier J, Exley R M, Parsot C, Guadagnini S, Prevost M C, Prochnicka-Chalufour A, Delepierre M, Tanguy M, Tang C M. Optimization of virulence functions through glucosylation of *Shigella* LPS. Science 2005; 307: 1313-1317) were propagated and their LPS extracted by phenol extraction. The LPS derived from:—(1) wild-type *Shigella* M90; (2) waaL, were added at 25 ng/ml.

Figure 37:
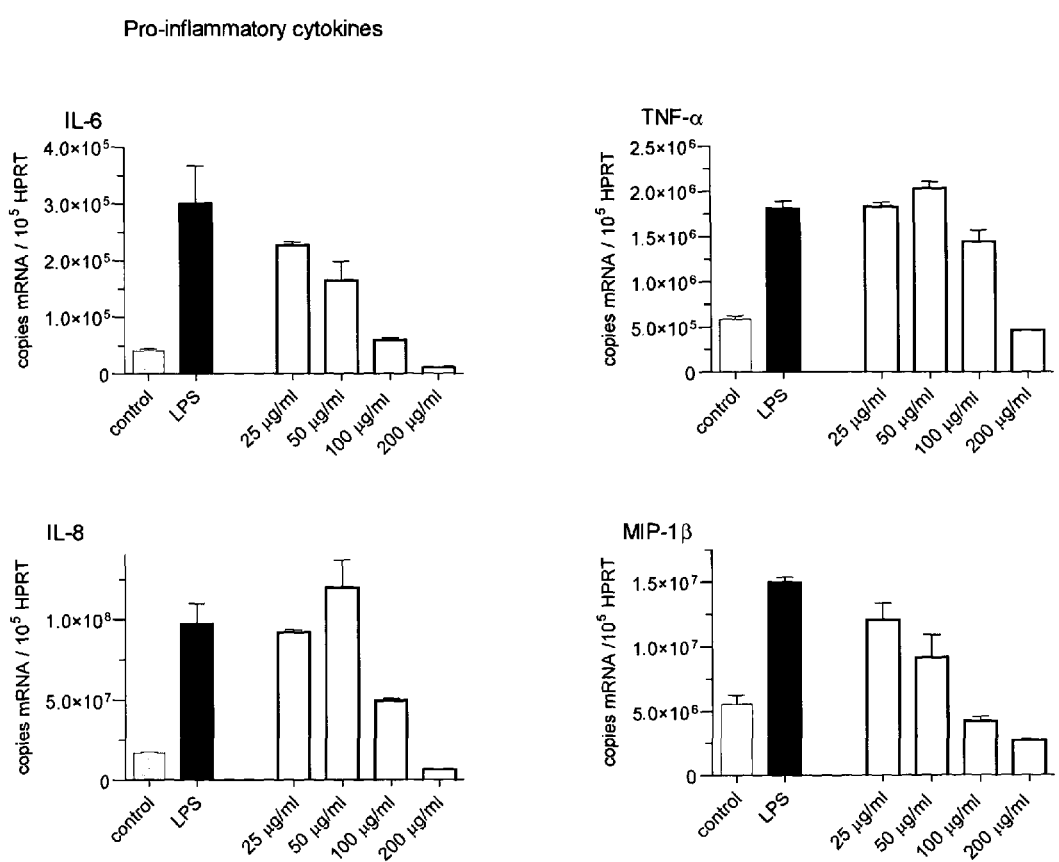

Treatment of human monocytes with LPS isolated from wild type and waaL *Shigella* mutants induced the expression of the pro-inflammatory cytokines IL-6, TNF-alpha, IL-8 and MIP-1 beta at similar levels. Pre-treatment of monocytes with 25 to 100 µg/ml of generation 3 anionic polypropyletherimine carboxylic acid terminated dendrimer glucosamine resulted in a dose dependant reduction of all of these pro-inflammatory cytokines when *Shigella* wild type LPS was used (FIG. 37), and also when *Shigella* waaL mutant LPS was also used (FIG. 37). A modest reduction of the pro-inflammatory cytokines was seen with 25 µg/ml of generation 3 polypropyletherimine carboxylic acid terminated dendrimer glucosamine with a maximal effect seen at a dose of 100 µg/ml of generation 3 anionic polypropyletherimine carboxylic acid terminated dendrimer glucosamine.

Example 2E

Assay for Inhibition of Pro-Inflammatory Cytokine Production by G3.5 Polyamidoamine Dendrimer Glucosamine and G3 Polypropyletherimine Dendrimer Glucosamine after Challenge of Rabbits Infected with Wild Type *Shigella* Sp. Infection Surgery to create ileal loop sacs in rabbits was performed as described previously (Perdomo et al 1994). This rabbit model has proven invaluable for studies of mucosal inflammation and bacterial invasion in infectious diarrheas. Shigellosis (and the typhoid fever of *salmonella*) lead to inflammatory changes in the epithelium associated lymphoid follicles; i.e., Peyer's patches (Perdomo O J, Cavaillon J M, Huerre M, Ohayon H, Gounon P, Sansonetti P J. Acute inflammation causes epithelial invasion and mucosal destruction in experimental shigellosis. J Exp Med. 1994; 180: 1307-1319.; Sansonetti P J, Arondel J, Cavaillon J M, Huerre S M. Role of interleukin-1 in the pathogenesis of experimental shigellosis. J Clinical Investigation 1995; 96: 884-892). The localised but excessive IL-6 and TNF-alpha mediated pro-inflammatory cytokine response that follows leads to the destruction of the intestinal epithelium because:—(1) the organism multiples in the lumen of the isolated ileal loops; (2) a severe host mediated pro-inflammatory response occurs; (3) the mucosal barrier is damaged; and (4) bacterial invasion occurs through the gut associated lymphoid tissues (i.e., Peyer's patches). This is associated with an infiltration of:—(a) blood derived monocytes that differentiate into macrophages; and (b) neutrophils. The inflammatory changes in this rabbit based ileal loop model depend directly upon the presence of *shigella* LPS and the production of IL-6 and TNF-alpha by the large numbers of incoming blood monocytes.

For these experiments, wild-type M90 *Shigella flexneri* bacteria were grown in broth, harvested whilst still in the exponential phase of growth, and diluted to give a concentration of $2\times10^7$ bacteria per ml. The rabbit ileal loops containing Peyer's patches were treated with 2.5 mg of generation 3.5 polyamidoamine (PAMAM) dendrimer glucosamine and the control loop was treated with 2.5 mg of generation 3.5 polyamidoamine (PAMAM) dendrimer. These molecules were administered in a volume of 1 ml of water. $10^7$ M90 *Shigella flexneri* bacteria were then injected into each ileal loop. The abdomen was closed and the rabbits left for 16 h. The rabbits were then killed and the ileal loops and Peyer's patches sampled. Tissue was immediately immersed in 2 ml of TriReagent, homogenised for 1 min using a Polytron homogenizer and the RNA extracted for quantitative real-time RT-PCR based studies of pro-inflammatory cytokines.

No adverse reaction were seen when dendrimer glucosamine was administered into the ileal loops. In these experiments, and using wild type *Shigella flexneri* (M90T strain; $10^7$ organisms/loop), it was shown that:—(1) Neither the dendrimer nor the PAMAM dendrimer glucosamine had an anti-microbial effect on the *Shigella flexneri* when administered into the ileal loops; (2) A significant and therapeutically beneficial effect could be achieved after the oral administration of dendrimer glucosamine into the gut lumen; (3) No clinical toxicity was seen; (4) Functional tissue injury was reduced by PAMAM dendrimer glucosamine as determined by a 90% reduction in the volume of bloody diarrhea that occurs during a *shigella* infection; (5) Histo-pathological studies showed that infected animals receiving dendrimer only have a marked tissue pro-inflammatory cell infiltrate in the gut wall and gut lumen, edema of the lymphoid follicles (i.e., Peyer's patches), extensive destruction of the epithelium associated with the lymphoid follicle, and inflammation, hemorrhagic infiltration, dilatation, shortening and destruction of the villi between the lymphoid follicles (i.e., Peyer's patches). In contrast, the histo-pathological findings were quite different in the infected animals treated by the oral administration of dendrimer glucosamine into the gut lumen in that there were minimal morphological changes in the mucosal villi and Peyer's patch follicles, and the tissue based inflammatory cell infiltrate present did not cause epithelium rupture; (6) There was a large reduction in pro-inflammatory cytokine production as demonstrated by a 1,000-fold reduction in IL-6 production, a 100-fold reduction in IL-8 production, and a 100-fold reduction in TNF-alpha production. Importantly, for the anti-inflammatory cytokine IL-10, there was no difference. For the dendritic cell maturation mediator—Interferon-beta—there was also no difference. For the epithelial cell anti-microbial peptide β-defensin, there was no difference. These animal model based results showed that dendrimer glucosamine can substantially alter the course of a gut infection even when an antibiotic is not co-administered during the course of these experiments.

The above experiment was repeated with a G3 polypropyletherimine dendrimer glucosamine according to the present invention. Surgery to create ileal loop sacs in rabbits was performed as described above. For these experiments, wild-type M90 *Shigella flexneri* bacteria were grown in broth, harvested whilst still in the exponential phase of growth, and diluted to give a concentration of $2\times10^7$ bacteria per ml. The rabbit ileal loops containing Peyer's patches were treated with 0.5 mg of G3 polypropyletherimine dendrimer glucosamine/loop and the control loop was treated with water for injection. These molecules were administered in a volume of 0.5 ml of water. $10^7$ M90 *Shigella flexneri* bacteria were then injected into each ileal loop. The abdomen was closed and the rabbits left for 16 h. The rabbits were then killed and the ileal loops and Peyer's patches sampled. Tissue was immediately immersed in 2 ml of TriReagent, homogenised for 1 min using a Polytron homogenizer and the RNA extracted for quantitative real-time RT-PCR based studies of pro-inflammatory cytokines.

No adverse reaction were seen when dendrimer glucosamine was administered into the ileal loops. In these experiments, and using wild type *Shigella flexneri* (M90T strain; $10^7$ organisms/loop), it was shown that:—(1) The polypropyletherimine dendrimer glucosamine had no anti-microbial effect on the *Shigella flexneri* when administered into the ileal loops; (2) A significant and therapeutically beneficial effect could be achieved after the local administration of polypropyletherimine dendrimer glucosamine into the gut lumen; (3) No clinical toxicity was seen; (4) Functional tissue injury was reduced by polypropyletherimine dendrimer glucosamine as determined by a 90% reduction in the volume of bloody diarrhea that occurs during a *shigella* infection; (5) Histo-pathological studies showed that infected but untreated animals had a marked tissue pro-inflammatory cell infiltrate in the gut wall and gut lumen, edema of the lymphoid follicles (i.e., Peyer's patches), extensive destruction of the epithelium associated with the lymphoid follicle, and inflammation, hemorrhagic infiltration, dilatation, shortening and destruction of the villi between the lymphoid follicles (i.e., Peyer's patches). In contrast, the macroscopic findings in the animals that were infected and treated with intra-luminal gut administration of G3 polypropyletherimine dendrimer glucosamine were, on visual inspection, quite different in that the gut mucosa and the lymphoid follicles were normal with no evidence of infection related damage; (6) There was a large reduction in pro-inflammatory cytokine production as demonstrated by a 260-fold reduction in IL-6 production, and a 55-fold reduction in IL-8 production. Importantly, for the anti-inflammatory cytokine IL-10, there was no difference. These animal model based results showed that dendrimer glucosamine can substantially alter the course of a gut infection even when an antibiotic is not co-administered during the course of the experiments.

Example 2F

Assay for Inhibition of Pro-Inflammatory Cytokine Production by Generation 3 Polypropyletherimine Carboxylic Acid Terminated Dendrimer Glucosamine after Challenge with LPS, Live *E. coli* Bacteria, Live *Klebsiella aeruginosa* Bacteria, Live *S. aureus* Bacteria, Live *E. faecalis* Bacteria, and Live *Pseudomonas Aerugenosa* Bacteria 1 ml aliquots of human monocytes ($10^6$ cells/ml) were transferred to a 24-well tissue culture plate and incubated for 30 min at 37° C. To these adherent monocytes, endotoxin free dendrimer glucosamine was added at concentrations from 50 to 200 μg/ml and incubated for 1 h at 37° C. Live *E. coli, Klebsiella aeruginosa, S. aureus, E. faecalis*, and *Pseudomonas aerugenosa* from overnight bacterial cultures were added to separate plates of monocytes at a multiplicity of infection of 10 infectious bacteria per monocyte (total volume 50 μL) and centrifuged at 780 g for 7 min to maximise the contact between the bacteria and the monocytes. The cells were then maintained at 37° C. with 5% $CO_2$ for 1 h. Gentamicin (100 μg/ml) was then added and the tissue culture plate incubated for an additional 2 h. Media was then removed, cells lysed in 500 μL Tri-reagent (Sigma), and the RNA extracted. Reverse transcription was performed using a Qiagen RT kit. Aliquots of cDNA were then subjected to quantitative real-time mRNA PCR for pro-inflammatory cytokines.

A large reduction in the synthesis of the pro-inflammatory cytokines IL-6 (FIG. 39), TNF-alpha (FIG. 40) and MIP-1 beta (FIG. 41) was seen in the presence of the generation 3 polypropyletherimine carboxylic acid terminated dendrimer glucosamine (12.5% loading) molecule at a concentration of 100 μg/ml.

Example 3

Studies of G3 Polypropyletherimine Carboxylic Acid Terminated Dendrimer Glucosamine 6-Sulfate To prepare endotoxin-free solutions and glassware, all glassware and magnetic fleas were autoclaved twice at 123° C. for 15 minutes. The synthesis was performed using sterile and endotoxin free disposable plastic tissue culture grade 50 ml universal tubes. All other disposable plastic pipettes, universals and syringes are certified endotoxin-free (i.e., endotoxin <0.01 endotoxin units (EU)/ml). Endotoxin free water for injection was used. This means that endotoxin contamination was reduced to a minimum from the very start of the partial glycosylation synthesis reaction. In order to eliminate any bacterial contamination of the pH probe used, it was first immersed in 1 N HCl solution for 15 minutes before being used, and then washed 4 times with endotoxin free water to remove any residual acid.

150 mg of the Generation 3 polypropyletherimine dendrimer (i.e., with 16 peripheral carboxylic acid groups) was dissolved in 1.5 ml sterile endotoxin free water to give a concentration of 100 mg/ml. A magnetic flea was put into the 50 ml Falcon tube and stirred at a slow speed on a magnetic stirring plate. 150 mg of D-glucosamine 6-sulfate from Sigma UK (catalogue number G8641) was dissolved in 3 ml of sterile water to give a concentration of 50 mg/ml. It was then added to the dissolved dendrimer. This was equivalent to 0.78 glucosamine 6-sulfate molecules per peripheral carboxylic acid group on the dendrimer. The pH of the resulting solution (which is quite acidic) was readjusted to 5.0 using 1 N NaOH. Then, 334 mg of 1-ethyl-3-3-dimethylaminopropyl carboiimide hydrochloride (EDCI, Sigma UK) was dissolved in 6.7 ml sterile water to give a concentration of 50 mg/ml. This was equivalent to 1.94 EDCI molecules per peripheral carboxylic acid group on the dendrimer. The EDCI solution was then added immediately to the solution containing the dendrimer and the glucosamine 6-sulfate. The pH was readjusted to 5.0 with 1 N HCl. The pH of the reaction solution was readjusted to 5.0 by adding 1 N HCl every 15-30 minutes during the 3 hour reaction. The final volume of the reaction was about 12-12.5 ml.

For the dialysis steps that followed, all glass beakers and magnetic stir bars were autoclaved twice at 123° C. for 15 minutes. Endotoxin free water (Baxter Healthcare) was used. A Slide-a-lyser dialysis cassette (Pierce) with a MWt cut-off of 2 kDa and a volume of 3-12 ml was used. The dialysis cassette was rehydrated using endotoxin-free water, filled with the solution, and then dialysed (with stirring) for 1 hour in 1 L of endotoxin free water at 4° C. All subsequent dialysis was at 4° C. The water was then replaced and the dialysis continued overnight. The following day, the water was replaced and the dialysis continued for another 24 hours, with a further 4 changes of water at 3.5 hour intervals, and including another overnight dialysis. In total, this meant 42 hours of dialysis at 4° C. with 7 changes of water. The dialysate was then removed from the cassettes with a needle and syringe and filtered through 0.2 μm sterile filters and placed in pre-weighed sterile 50 ml Falcon tubes. It was then frozen for at least 1 hour at −80° C. Parafilm was placed over the mouth of the 50 ml tube that contained the frozen dendrimer glucosamine 6-sulfate and pierced with a needle. The tube was then placed in a freeze drier (which has been pre-run for 30 min) and its contents left to lyophilize for 48 hours.

The lyophilised product was confirmed to be endotoxin free at <0.06 EU/ml using the limulus amoebocyte assay. As the dendrimer glucosamine 6-sulfate is hygroscopic, it was stored in small airtight containers, and under argon, and at 4° C., and wrapped in aluminium foil. H-NMR and C-NMR and MALDI-MS studies showed that the Generation 3 polypropyletherimine dendrimer (with 16 peripheral carboxylic acid groups) had a loading of 2 or 3 glucosamine molecules per dendrimer. In addition, there was no residual small molecule contamination of the product with acrylonitrile, acrylic acid, free glucosamine or urea.

This molecule was first tested for:—(a) its cytotoxicity; (b) its ability to reduce pro-inflammatory cytokine production. This molecule's cytotoxicity was determined as follows. Peripheral blood mononuclear (PBMN) cells were isolated from fresh human blood by density gradient centrifugation and re-suspended in growth medium (RPMI 1640, 20 mM L-glutamine, penicillin [250 IU/ml], streptomycin [250 μg/ml] and 10% endotoxin free human serum). They were allowed to adhere to 14 cm plastic tissue culture plates for 1 h. The plates were washed, the adherent monocytes scraped with a cell scraper, and the cell density adjusted to $10^6$ cells/ml. 200 μL of these monocytes were plated in a 96 well plate at a density of $10^6$ cells/ml. The generation 3 dendrimer glucosamine 6-sulfate (0 to 400 μg/ml) was then added to monocytes and incubated for 24 h. Cell viability was assessed using the MTT assay.

The ability of this generation 3 dendrimer glucosamine 6-sulfate to reduce the production of a panel of pro-inflammatory cytokines was determined in a human monocyte/macrophage based assay with LPS being used to stimulate the release of pro-inflammatory cytokines. 1 ml aliquots of human monocytes ($10^6$ cells/ml) were transferred to a 24-well tissue culture plate and incubated for 30 min at 37° C. To these adherent monocytes, endotoxin free (i.e., <0.06 EU/ml) generation 3 dendrimer glucosamine 6-sulfate was added at concentrations from 50 to 200 μg/ml and incubated for 1 h at 37° C. LPS (Salmonella Minnesota, Sigma. Catalogue number L9764) was added at 25 ng/ml. Positive controls were cells treated with LPS only and the negative controls were untreated cells. The cells were then maintained at 37° C. with 5% $CO_2$ for 3 h. Media was then removed, cells lysed in 500 μL of Tri-reagent (Sigma) and RNA extracted. Reverse transcription was performed using a Qiagen RT kit. Aliquots of cDNA were then subjected to quantitative real-time PCR for TNF-alpha and MIP-1 beta.

This generation 3 dendrimer glucosamine 6-sulfate was not cytotoxic to monocytes in an MTT assay at the concentrations tested. It did not reduce TNF-alpha cytokine production and it did not reduce MIP-1 beta chemokine production (FIG. 56).

The biological effect of G3 polypropyletherimine dendrimer glucosamine 6-sulfate was determined in 24 well plates using $10^6$ human monocytes pretreated with 50 to 150 μg/ml endotoxin free dendrimer glucosamine 6-sulfate for 1 h followed by challenge with 25 ng/ml *Salmonella* LPS. After 3 h, RNA was extracted and real-time RT PCR performed. When compared with the LPS control, generation 3 polypropyletherimine dendrimer glucosamine 6-sulfate did not lead to a reduction in the pro-inflammatory cytokine TNF-alpha or the pro-inflammatory chemokine MIP-1 beta.

FIG. 1: Illustration showing competition for cell surface Toll-like receptor 4 (TLR4) between the agonist (lipopolysaccharide [LPS]) and the antagonist (dendrimer glucosamine). MD2 is a protein and R1, R2, R3, and R4 are acyl chains.

Figure 2:
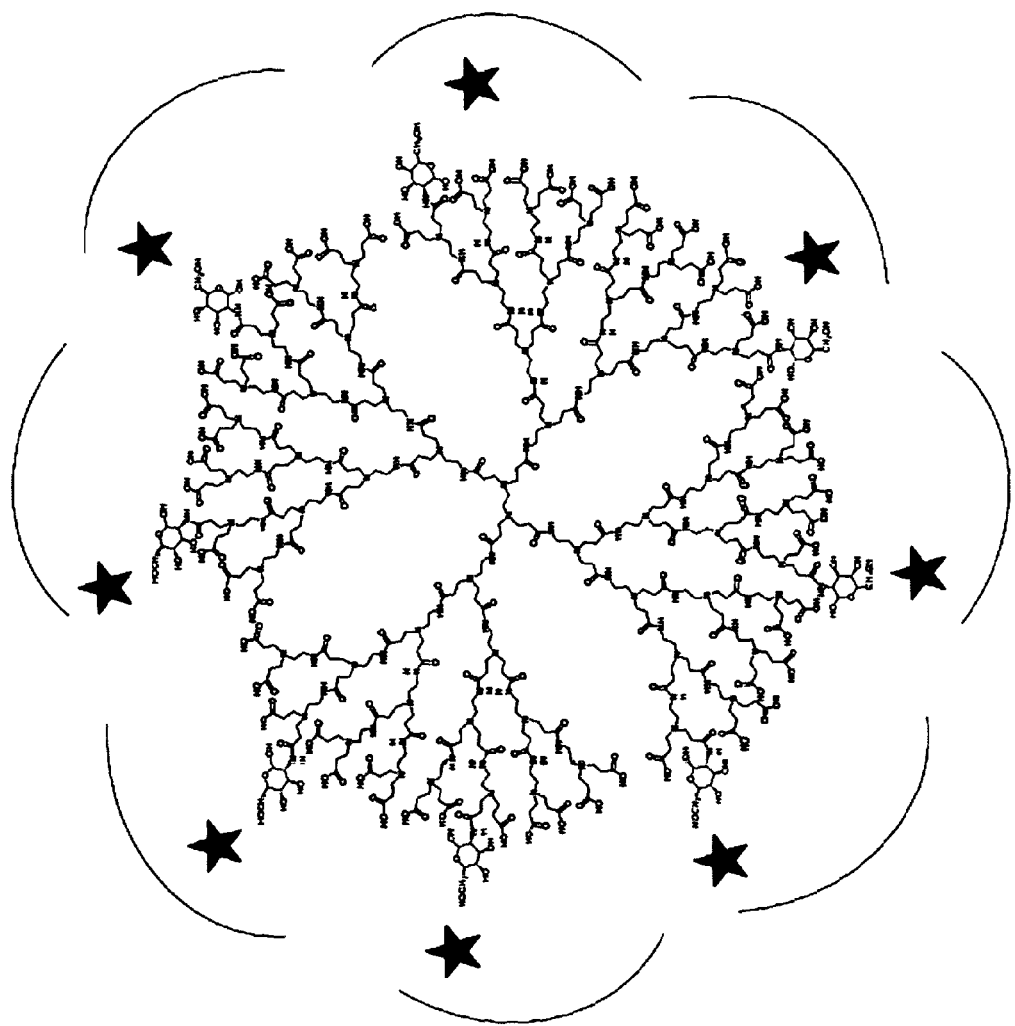

FIG. 2: Generation 3.5 anionic carboxylic acid terminated (i.e., 64 peripheral carboxylic acid groups) PAMAM dendrimer glucosamine with a 12.5% surface loading of glucosamine (i.e., 8 glucosamine molecules) with a zero length amide bond between the dendrimer and the glucosamine. The glucosamine molecules are evenly spaced on the surface of the dendrimer as illustrated by each of the black stars. Each of the arcs (n=8) represents the eight carboxylic acid groups to one of which is covalently attached a glucosamine molecule. This analytical chemistry observation is consistent with higher occupied molecular orbital and lowest occupied molecular orbital calculations that were performed using the frontier molecular orbital theory. In the case of a generation 3.5 anionic carboxylic acid terminated (i.e., 64 peripheral carboxylic acid groups) PAMAM dendrimer, the incremental addition of each glucosamine proceeds in a energy favourable manner until 8 glucosamine molecules have been evenly attached to 8 of the 64 peripheral carboxylic acid groups available. Thereafter, the higher occupied molecular orbital energy values rapidly become unfavourable to the addition of any further glucosamine molecules. This suggests that the divergent approach to the synthesis of dendrimer glucosamine leads to the sterically and energetically optimum addition of 8 glucosamine molecules on the 64 carboxylic acid groups of a generation 3.5 anionic carboxylic acid terminated PAMAM dendrimer. This equates to one glucosamine molecule per eight peripheral carboxylic acid groups; it equates to a 12.5% surface loading of glucosamine on the surface of the dendrimer.

FIG. 3: The biological effect of generation 3.5 PAMAM dendrimer glucosamine was determined in 24 well plates using $10^6$ human monocytes pretreated with 25 to 200 μg/ml endotoxin free dendrimer glucosamine for 1 h followed by challenge with 25 ng/ml *Salmonella* LPS. After 3 h, RNA was extracted and real-time RT PCR performed. When compared with the LPS control, generation 3.5 PAMAM dendrimer glucosamine lead to the following reductions in pro-inflammatory cytokines:—an 830-fold reduction in IL-6, a 110-fold reduction in TNF-alpha, a 10-fold reduction in IL-8, and a 55-fold reduction in MIP-1 beta at 200 μg/ml. In contrast, there was no change in the anti-inflammatory cytokines IL-10 and interferon-beta.

FIG. 4: The biological effect of generation 3.5 PAMAM dendrimer glucosamine was determined in 24 well plates using $10^6$ human dendritic cells pretreated with 25 to 200 μg/ml endotoxin free dendrimer glucosamine for 1 h followed by challenge with 25 ng/ml *Salmonella* LPS. After 3 h, RNA was extracted and real-time RT PCR performed. When compared with the LPS control, generation 3.5 PAMAM dendrimer glucosamine lead to the following reductions in pro-inflammatory cytokines:—an 850-fold reduction in IL-6, a 90-fold reduction in TNF-alpha, a 600-fold reduction in IL-8, and a 70-fold reduction in MIP-1 beta at 200 μg/ml. In contrast, there was no change in the anti-inflammatory cytokines IL-10 and interferon-beta.

FIG. 5: The biological effect of generation 3.5 PAMAM dendrimer glucosamine was determined in 24 well plates using $10^6$ human dendritic cells pretreated with 25 to 200 μg/ml endotoxin free dendrimer glucosamine for 1 h followed by challenge with 25 ng/ml *Shigella* LPS. After 3 h, RNA was extracted and real-time RT PCR performed. When compared with the LPS control, generation 3.5 PAMAM dendrimer glucosamine lead to the following reductions in pro-inflammatory cytokines:—an 125-fold reduction in IL-6, a 13-fold reduction in TNF-alpha, a 175-fold reduction in IL-8, and a 30-fold reduction in MIP-1 beta at 200 μg/ml. In contrast, there was no change in the anti-inflammatory cytokines IL-10 and interferon-beta.

FIG. 6: Crystal structure of human MD-2 with PDB entry 2E56 displayed as its electrostatic potential surface. (A) The residues Lys91, Arg96, Tyr102 and Ser118 form electrostatic interactions with the partially glycosylated dendrimer. The square black box represents the "top right" orientation of MD-2; (B) Human MD2 is shown in its "top right" orientation. The residues Ser98, Tyr102, Arg106, Lys109, Thr112, Asn114 and Thr116 form electrostatic interactions with the partially glycosylated dendrimer. These residues, which border the entrance of human MD2's hydrophobic pocket, are labelled in the figures.; (C) Interaction of the partially glycosylated dendrimer's surface with human MD-2's surface. Residues shown in red are <1.3 Å away from the surface of human MD-2. Glucosamine residues are shown in ball and stick configuration. Shown is a side view of human MD-2's pocket.; (D) Interaction of the partially glycosylated dendrimer's surface with human MD2's surface. Residues shown in red are <1.3 Å away from the surface of human MD2. Glucosamine residues are shown in ball and stick configuration. Shown is a frontal view of human MD2's pocket.

FIG. 7: The overall structure of dendrimer glucosamine when it is bound to MD2 is shown in two orientations. When bound in this manner to MD2 (dark), dendrimer glucosamine (light) can act as a partial antagonist of the TLR4-MD2-LPS complex.

FIG. 8: Cellular cytotoxicity was determined by an MTT assay performed on $10^5$ human monocytes in 96 well plates using 0 to 800 μg/ml of an endotoxin free generation 2 triazine carboxylic acid terminated dendrimer. No cytotoxic effect was observed. The biological effect of the generation 2 triazine carboxylic acid terminated dendrimer was determined in 24 well plates using $10^6$ monocytes pretreated with 400 to 1,000 μg/ml endotoxin free dendrimer glucosamine for 1 h followed by challenge with 25 ng/ml *Salmonella* LPS. After 3 h, RNA was extracted and real-time RT PCR performed. When compared with the LPS control, generation 2 triazine carboxylic acid terminated dendrimer had no significant effect on pro-inflammatory cytokines such as TNF-alpha and MIP-1 beta.

FIG. 9: Cellular cytotoxicity was determined by an MTT assay performed on $10^5$ human monocytes in 96 well plates using 0 to 800 μg/ml of an endotoxin free generation 2 triazine carboxylic acid terminated dendrimer glucosamine (synthesis with 6 eq. of glucosamine at pH 8). No cytotoxic effect was observed. The biological effect of the generation 2 triazine carboxylic acid terminated dendrimer glucosamine (synthesis with 6 eq. of glucosamine at pH 8) was determined in 24 well plates using $10^6$ monocytes pretreated with 400 to 1,000 μg/ml endotoxin free dendrimer glucosamine for 1 h followed by challenge with 25 ng/ml *Salmonella* LPS. After 3 h, RNA was extracted and real-time RT PCR performed. When compared with the LPS control, generation 2 triazine carboxylic acid terminated dendrimer glucosamine (synthesis with 6 eq. of glucosamine at pH 8) had no significant effect on pro-inflammatory cytokines such as TNF-alpha and MIP-1 beta.

FIG. 10: Cellular cytotoxicity was determined by an MTT assay performed on $10^5$ human monocytes in 96 well plates using 0 to 800 µg/ml of an endotoxin free generation 2 triazine carboxylic acid terminated dendrimer glucosamine (synthesis with 12 eq. of glucosamine at pH 8). No cytotoxic effect was observed. The biological effect of the generation 2 triazine carboxylic acid terminated dendrimer glucosamine (synthesis with 12 eq. of glucosamine at pH 8) was determined in 24 well plates using $10^6$ monocytes pretreated with 400 to 1,000 µg/ml endotoxin free dendrimer glucosamine for 1 h followed by challenge with 25 ng/ml *Salmonella* LPS. After 3 h, RNA was extracted and real-time RT PCR performed. When compared with the LPS control, generation 2 triazine carboxylic acid terminated dendrimer glucosamine (synthesis with 12 eq. of glucosamine at pH 8) had no significant effect on pro-inflammatory cytokines such as TNF-alpha and MIP-1 beta.

FIG. 11: Cellular cytotoxicity was determined by an MTT assay performed on $10^5$ human monocytes in 96 well plates using 0 to 800 µg/ml of an endotoxin free generation 2 triazine carboxylic acid terminated dendrimer glucosamine (synthesis with 120 eq. of glucosamine at pH 7). No cytotoxic effect was observed. The biological effect of the generation 2 triazine carboxylic acid terminated dendrimer glucosamine (synthesis with 120 eq. of glucosamine at pH 7) was determined in 24 well plates using $10^6$ monocytes pretreated with 400 to 1,000 µg/ml endotoxin free dendrimer glucosamine for 1 h followed by challenge with 25 ng/ml *Salmonella* LPS. After 3 h, RNA was extracted and real-time RT PCR performed. When compared with the LPS control, generation 2 triazine carboxylic acid terminated dendrimer glucosamine (synthesis with 120 eq. of glucosamine at pH 7) had no significant effect on pro-inflammatory cytokines such as TNF-alpha and MIP-1 beta.

FIG. 12: Cellular cytotoxicity was determined by an MTT assay performed on $10^5$ human monocytes in 96 well plates using 0 to 800 µg/ml of an endotoxin free generation 2 triazine carboxylic acid terminated dendrimer glucosamine (synthesis with 120 eq. of glucosamine at pH 5). No cytotoxic effect was observed. The biological effect of the generation 2 triazine carboxylic acid terminated dendrimer glucosamine (synthesis with 120 eq. of glucosamine at pH 5) was determined in 24 well plates using $10^6$ monocytes pretreated with 400 to 1,000 µg/ml endotoxin free dendrimer glucosamine for 1 h followed by challenge with 25 ng/ml *Salmonella* LPS. After 3 h, RNA was extracted and real-time RT PCR performed. When compared with the LPS control, generation 2 triazine carboxylic acid terminated dendrimer glucosamine (synthesis with 120 eq. of glucosamine at pH 5) had no significant effect on pro-inflammatory cytokines such as TNF-alpha and MIP-1 beta.

FIG. 13: Cellular cytotoxicity was determined by an MTT assay performed on $10^5$ human monocytes in 96 well plates using 0 to 400 µg/ml of an endotoxin free generation 3 triazine carboxylic acid terminated dendrimer. No cytotoxic effect was observed. The biological effect of the generation 3 triazine carboxylic acid terminated dendrimer was determined in 24 well plates using $10^6$ monocytes pretreated with 25 to 200 µg/ml endotoxin free dendrimer glucosamine for 1 h followed by challenge with 25 ng/ml *Salmonella* LPS. After 3 h, RNA was extracted and real-time RT PCR performed. When compared with the LPS control, generation 3 triazine carboxylic acid terminated dendrimer had no significant effect on pro-inflammatory cytokines such as 11-6, TNF-alpha, 11-8 and MIP-1 beta.

FIG. 14: Cellular cytotoxicity was determined by an MTT assay performed on $10^5$ human monocytes in 96 well plates using 0 to 400 µg/ml of an endotoxin free generation 3 triazine carboxylic acid terminated dendrimer glucosamine (synthesis with 12 eq. of glucosamine) No cytotoxic effect was observed. The biological effect of the generation 3 triazine carboxylic acid terminated dendrimer glucosamine (synthesis with 12 eq. of glucosamine) was determined in 24 well plates using $10^6$ monocytes pretreated with 25 to 200 µg/ml endotoxin free dendrimer glucosamine for 1 h followed by challenge with 25 ng/ml *Salmonella* LPS. After 3 h, RNA was extracted and real-time RT PCR performed. When compared with the LPS control, generation 3 triazine carboxylic acid terminated dendrimer glucosamine (synthesis with 12 eq. of glucosamine) had no significant effect on pro-inflammatory cytokines such as IL-6, TNF-alpha, IL-8 and MIP-1 beta.

FIG. 15: Cellular cytotoxicity was determined by an MTT assay performed on $10^5$ human monocytes in 96 well plates using 0 to 400 µg/ml of an endotoxin free generation 3 triazine carboxylic acid terminated dendrimer glucosamine (synthesis with 14 eq. of glucosamine) No cytotoxic effect was observed. The biological effect of the generation 3 triazine carboxylic acid terminated dendrimer glucosamine (synthesis with 14 eq. of glucosamine) was determined in 24 well plates using $10^6$ monocytes pretreated with 50 to 400 µg/ml endotoxin free dendrimer glucosamine for 1 h followed by challenge with 25 ng/ml *Salmonella* LPS. After 3 h, RNA was extracted and real-time RT PCR performed. When compared with the LPS control, generation 3 triazine carboxylic acid terminated dendrimer glucosamine (synthesis with 14 eq. of glucosamine) had no significant effect on pro-inflammatory cytokines such as IL-6, TNF-alpha, IL-8 and MIP-1 beta.

FIG. 16: Cellular cytotoxicity was determined by an MTT assay performed on $10^5$ human monocytes in 96 well plates using 0 to 400 µg/ml of an endotoxin free hybrid generation 2 triazine generation 0.5 PAMAM carboxylic acid terminated dendrimer glucosamine No cytotoxic effect was observed. The biological effect of the hybrid generation 2 triazine generation 0.5 PAMAM carboxylic acid terminated dendrimer glucosamine was determined in 24 well plates using $10^6$ monocytes pretreated with 25 to 800 µg/ml endotoxin free dendrimer glucosamine for 1 h followed by challenge with 25 ng/ml *Salmonella* LPS. After 3 h, RNA was extracted and real-time RT PCR performed. When compared with the LPS control, hybrid generation 2 triazine generation 0.5 PAMAM carboxylic acid terminated dendrimer glucosamine had no significant effect on pro-inflammatory cytokines such as IL-6, TNF-alpha, IL-8 and MIP-1 beta.

FIG. 17: Cellular cytotoxicity was determined by an MTT assay performed on $10^5$ human monocytes in 96 well plates using 0 to 600 µg/ml of an endotoxin free hybrid generation 2 triazine generation 1.5 PAMAM carboxylic acid terminated dendrimer glucosamine No cytotoxic effect was observed. The biological effect of the hybrid generation 2 triazine generation 1.5 PAMAM carboxylic acid terminated dendrimer glucosamine was determined in 24 well plates using $10^6$ monocytes pretreated with 25 to 200 µg/ml endotoxin free dendrimer glucosamine for 1 h followed by challenge with 25 ng/ml *Salmonella* LPS. After 3 h, RNA was extracted and real-time RT PCR performed. When compared with the LPS control, hybrid generation 3 triazine generation 1.5 PAMAM carboxylic acid terminated dendrimer glucosamine significantly reduced pro-inflammatory cytokines:—a 105-fold reduction in IL-6, a 190-fold reduction in TNF-alpha, a 30-fold reduction in IL-8, and a 70-fold reduction in MIP-1 beta at 200 µg/ml. In contrast, there was no change in the anti-inflammatory cytokines IL-10 and interferon-beta.

Figure 18:
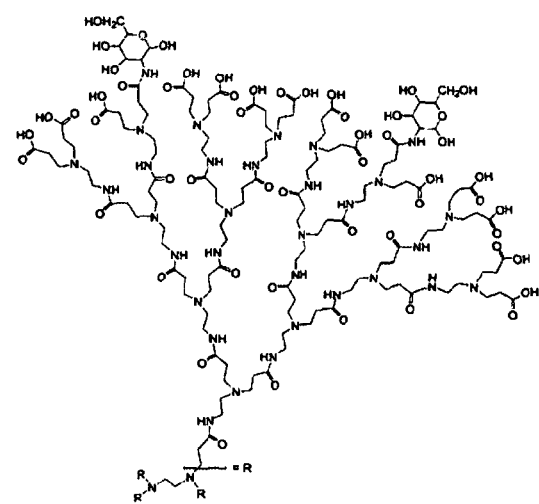

FIG. 18: Generation 3.5 anionic carboxylic acid terminated (i.e., 64 peripheral carboxylic acid groups) PAMAM dendrimer glucosamine with a 12.5% surface loading of glucosamine (i.e., 8 glucosamine molecules) with a zero length amide bond between the dendrimer and the glucosamine. This figure shows two sub-segments of the dendrimer. Each sub-segment has eight peripheral carboxylic acid groups. On each of these two sub-segments, there is one peripheral glucosamine molecule attached.

Figure 19:
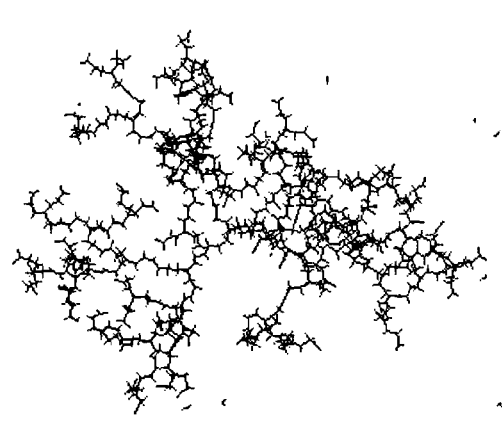

FIG. 19: Generation 3.5 anionic carboxylic acid terminated PAMAM dendrimer glucosamine with a 12.5% surface loading of glucosamine (i.e., 8 glucosamine molecules) with a zero length amide bond between the dendrimer and the glucosamine. This figure shows a solvated structure obtained using the simulating annealing protocol with Xplor-NIH.

Figure 20:
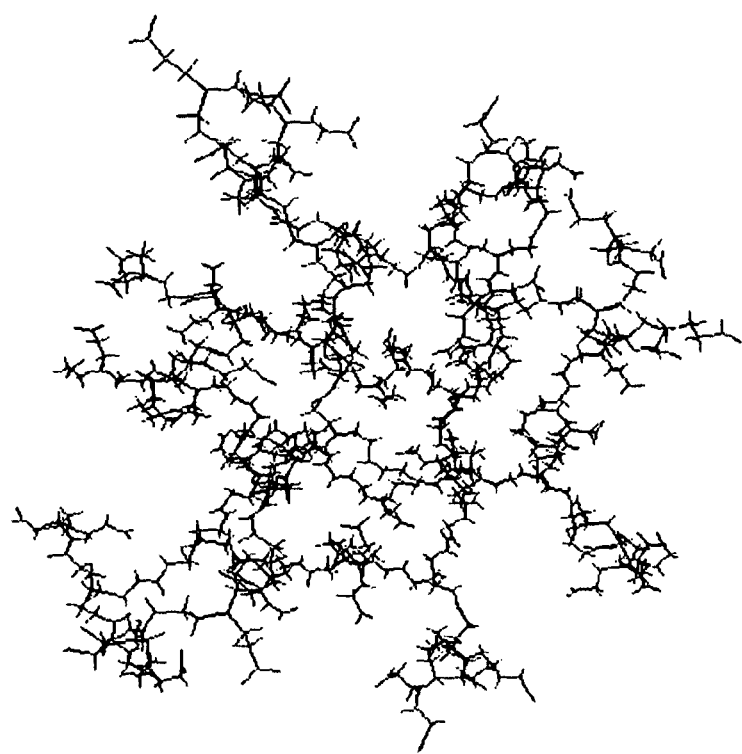
Figure 21:
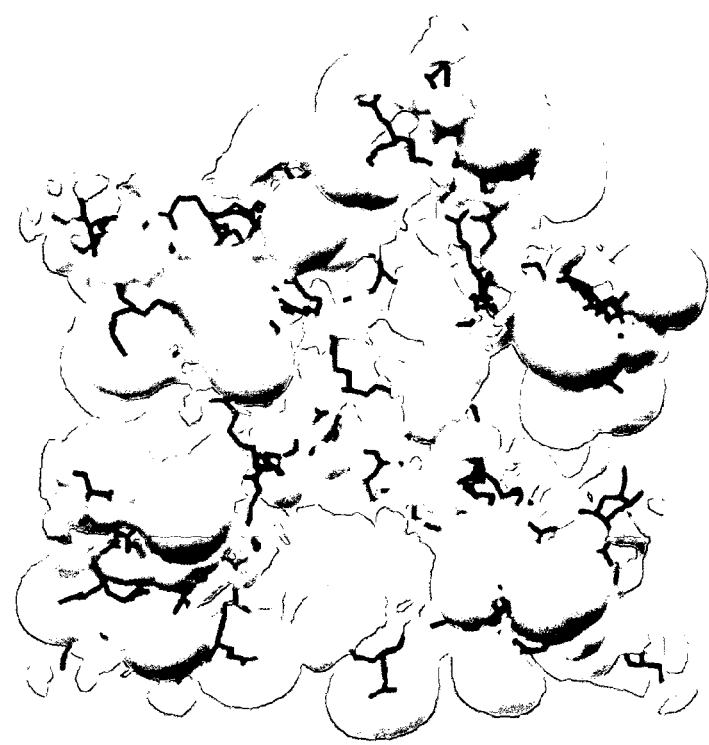

FIG. 20: Generation 3.5 anionic carboxylic acid terminated PAMAM dendrimer glucosamine with a 12.5% surface loading of glucosamine (i.e., 8 glucosamine molecules) with a zero length amide bond between the dendrimer and the glucosamine. This figure shows a non-solvated structure obtained using the simulating annealing protocol with Xplor-NIH.

FIG. 21: Generation 3.5 anionic carboxylic acid terminated PAMAM dendrimer glucosamine with a 12.5% surface loading of glucosamine (i.e., 8 glucosamine molecules) with a zero length amide bond between the dendrimer and the glucosamine. This modeling figure shows that the surface of this dendrimer glucosamine molecule has evenly distributed hydrophilic surfaces.

Figure 22:
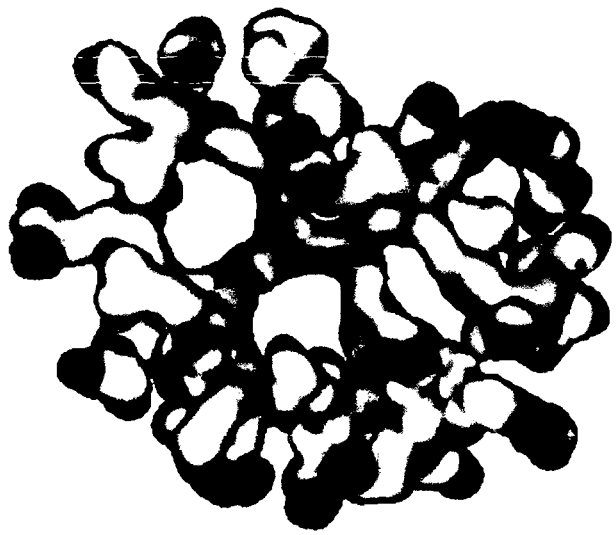

FIG. 22: Generation 3.5 anionic carboxylic acid terminated PAMAM dendrimer. This figure shows the interpolated charge surface. The dark areas correspond to negatively charged residues and the grey areas correspond to positively charged residues.

Figure 23:
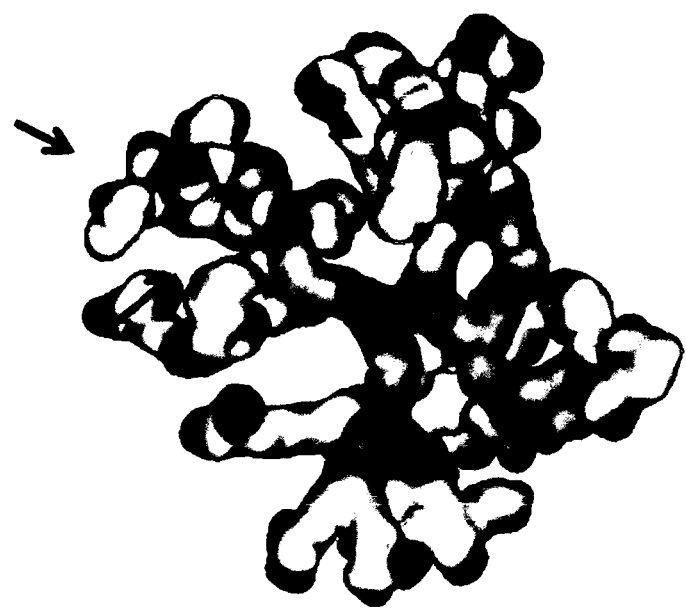

FIG. 23: Generation 3.5 anionic carboxylic acid terminated PAMAM dendrimer glucosamine with a 12.5% surface loading of glucosamine (i.e., 8 glucosamine molecules) with a zero length amide bond between the dendrimer and the glucosamine. This figure shows the interpolated charge surface. The dark areas correspond to negatively charged residues and the grey areas correspond to positively charged residues. The arrows mark the position of the 3 glucosamine molecules that are visible in this 2-D image.

Figure 24:
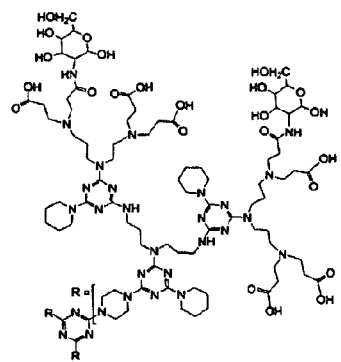

FIG. 24: Partially glycosylated Generation 2 triazine generation 0.5 PAMAM dendrimer glucosamine with a zero length amide bond between the dendrimer and the glucosamine. This figure shows two sub-segments of the dendrimer. On each of these sub-segments, there is one peripheral glucosamine molecule attached.

Figure 25:
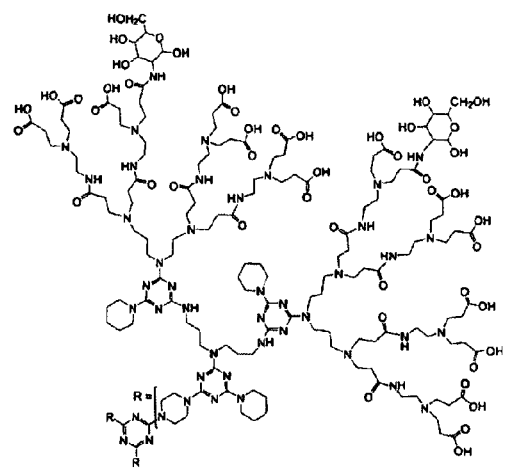

FIG. 25: Partially glycosylated Generation 2 triazine generation 1.5 PAMAM dendrimer glucosamine with a zero length amide bond between the dendrimer and the glucosamine. This figure shows two sub-segments of the dendrimer. On each of these sub-segments, there is one peripheral glucosamine molecule attached.

Figure 26:
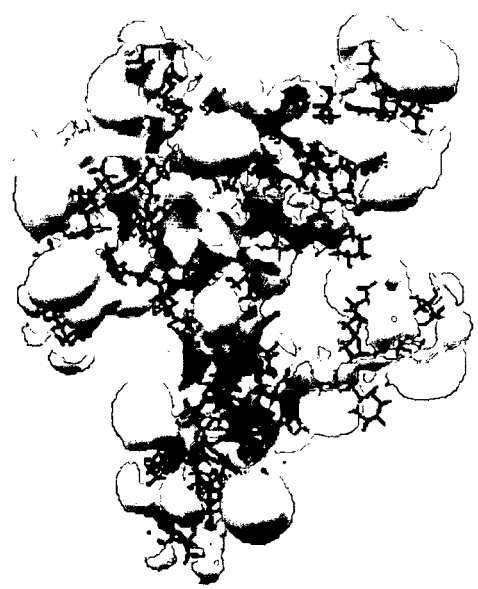

FIG. 26: Partially glycosylated Generation 2 triazine generation 0.5 PAMAM dendrimer glucosamine with a zero length amide bond between the dendrimer and the glucosamine. This figure shows modelling of its hydrophilic surfaces.

Figure 27:
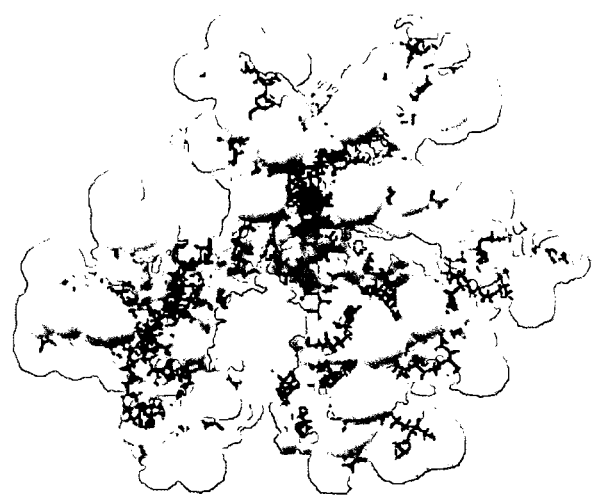

FIG. 27: Partially glycosylated Generation 2 triazine generation 1.5 PAMAM dendrimer glucosamine with a zero length amide bond between the dendrimer and the glucosamine. This figure shows modelling of its hydrophilic surfaces.

Figure 28:
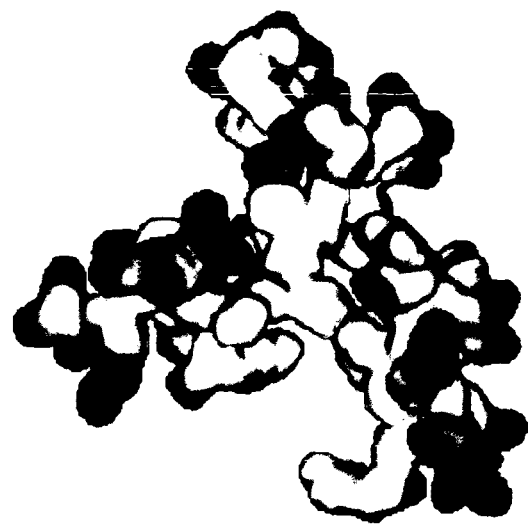

FIG. 28: Partially glycosylated Generation 2 triazine generation 0.5 PAMAM dendrimer glucosamine with a zero length amide bond between the dendrimer and the glucosamine. This figure shows the interpolated charge surface. The dark areas correspond to negatively charged residues and the grey areas correspond to positively charged residues.

Figure 29:
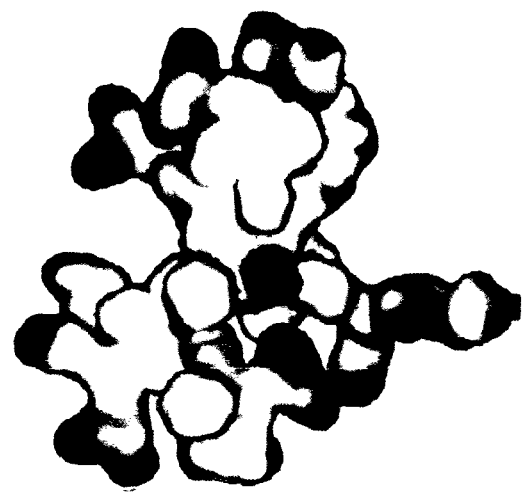

FIG. 29: Partially glycosylated Generation 2 triazine generation 1.5 PAMAM dendrimer glucosamine with a zero length amide bond between the dendrimer and the glucosamine. This figure shows the interpolated charge surface. The dark areas correspond to negatively charged residues and the grey areas correspond to positively charged residues.

FIG. 30: Generation 3 anionic carboxylic acid terminated (i.e., 16 peripheral carboxylic acid groups) polypropyletherimine dendrimer core. The entire and symmetrical dendrimer is shown in 2-dimensions. This dendrimer does not have internal cavities. It is therefore not suitable for acting as a drug delivery dendrimer.

FIG. 31: Generation 3 anionic carboxylic acid terminated (i.e., 16 peripheral carboxylic acid groups) polypropyletherimine dendrimer glucosamine with a 12.5% surface loading of glucosamine (i.e., 2 glucosamine molecules) with a zero length amide bond between the dendrimer and the glucosamine. The glucosamine molecules are evenly spaced on the surface of this symmetrical dendrimer as illustrated by each of the black stars. Each of the arcs (n=2) represents the eight carboxylic acid groups to one of which is covalently attached a glucosamine molecule. This analytical chemistry observation is consistent with higher occupied molecular orbital and lowest occupied molecular orbital calculations that were performed using the frontier molecular orbital theory. In the case of a generation 3 anionic carboxylic acid terminated (i.e., 16 peripheral carboxylic acid groups) polypropyletherimine dendrimer, the incremental addition of each glucosamine proceeds in a energy favourable manner until 2 glucosamine molecules have been attached to 2 of the 16 peripheral carboxylic acid groups available. Thereafter, the higher occupied molecular orbital energy values rapidly become unfavourable to the addition of any further glucosamine molecules. This suggests that the divergent approach to the synthesis of dendrimer glucosamine leads to the optimum addition of 2 glucosamine molecules on the 16 carboxylic acid groups of a generation 3 anionic carboxylic acid terminated polypropyletherimine dendrimer. This equates to one glucosamine molecule per eight peripheral carboxylic acid groups.

FIG. 32: Generation 3 anionic carboxylic acid terminated polypropyletherimine dendrimer glucosamine. This figure shows its overall molecular surface. This dendrimer does not have internal cavities. It is therefore not suitable for drug delivery purposes.

FIG. 33: Generation 3 anionic carboxylic acid terminated polypropyletherimine dendrimer glucosamine. This dendrimer glucosamine does not have internal cavities and is therefore not suitable for drug delivery purposes. This figure shows modeling of its hydrophilic surfaces.

FIG. 34: Cellular cytotoxicity was determined by an MTT assay performed on $10^5$ human monocytes in 96 well plates using 0 to 400 µg/ml of an endotoxin free generation 3 polypropyletherimine anionic carboxylic acid terminated dendrimer glucosamine No cytotoxic effect was observed. The biological effect of generation 3 polypropyletherimine anionic carboxylic acid terminated dendrimer glucosamine was determined in 24 well plates using $10^6$ peripheral blood mononuclear cells pretreated with 12.5 to 100 µg/ml endotoxin free dendrimer glucosamine for 1 h followed by challenge with 25 ng/ml *Salmonella* LPS. After 3 h, RNA was extracted and real-time RT PCR performed. When compared with the LPS control, generation 3 polypropyletherimine anionic carboxylic acid terminated dendrimer glucosamine lead to the following reductions in pro-inflammatory cytokines:—an 75-fold reduction in IL-6, a 390-fold reduction in TNF-alpha, a 75-fold reduction in IL-8, and a 165-fold reduction in MIP-1 beta at 100 µg/ml. In contrast, there was no change in the anti-inflammatory cytokines IL-10 and interferon-beta.

FIG. 35: Cellular cytotoxicity was determined by an MTT assay performed on $10^5$ human monocytes in 96 well plates using 0 to 400 µg/ml of an endotoxin free generation 3 polypropyletherimine anionic carboxylic acid terminated dendrimer glucosamine No cytotoxic effect was observed. The biological effect of generation 3 polypropyletherimine anionic carboxylic acid terminated dendrimer glucosamine was determined in 24 well plates using $10^6$ monocytes pretreated with 50 to 200 µg/ml endotoxin free dendrimer glucosamine for 1 h followed by challenge with 25 ng/ml *Salmonella* LPS. After 3 h, RNA was extracted and real-time RT PCR performed. When compared with the LPS control, generation 3 polypropyletherimine anionic carboxylic acid terminated dendrimer glucosamine lead to the following reductions in pro-inflammatory cytokines:—an 300-fold reduction in IL-6, a 135-fold reduction in TNF-alpha, a 5-fold reduction in IL-8, and a 100-fold reduction in MIP-1 beta at 100 µg/ml. In contrast, there was no change in the anti-inflammatory cytokines IL-10 and interferon-beta.

FIG. 36: Schematic cartoon of the possible truncation mutants of *Shigella* LPS. M90 is the wild type *Shigella flexneri*. gtrA is a mutant with reduced glucosylation. cld (chain length determinant) and rfB are 0-antigen truncated mutants. waal mutants only have the Lipid A and core sugars without the 0-antigen.

FIG. 37: The biological effect of generation 3 polypropyletherimine anionic carboxylic acid terminated dendrimer glucosamine was determined in 24 well plates using $10^6$ human monocytes pretreated with 25 to 200 µg/ml endotoxin free dendrimer glucosamine for 1 h followed by challenge with 25 ng/ml *Shigella* LPS. After 3 h, RNA was extracted and real-time RT PCR performed. When compared with the LPS control, generation 3 polypropyletherimine anionic carboxylic acid terminated dendrimer glucosamine lead to the following reductions in pro-inflammatory cytokines:—an 30-fold reduction in IL-6, a 4-fold reduction in TNF-alpha, a 15-fold reduction in IL-8, and a 6-fold reduction in MIP-1 beta at 100 µg/ml. In contrast, there was no change in the anti-inflammatory cytokines IL-10 and interferon-beta.

Figure 38:
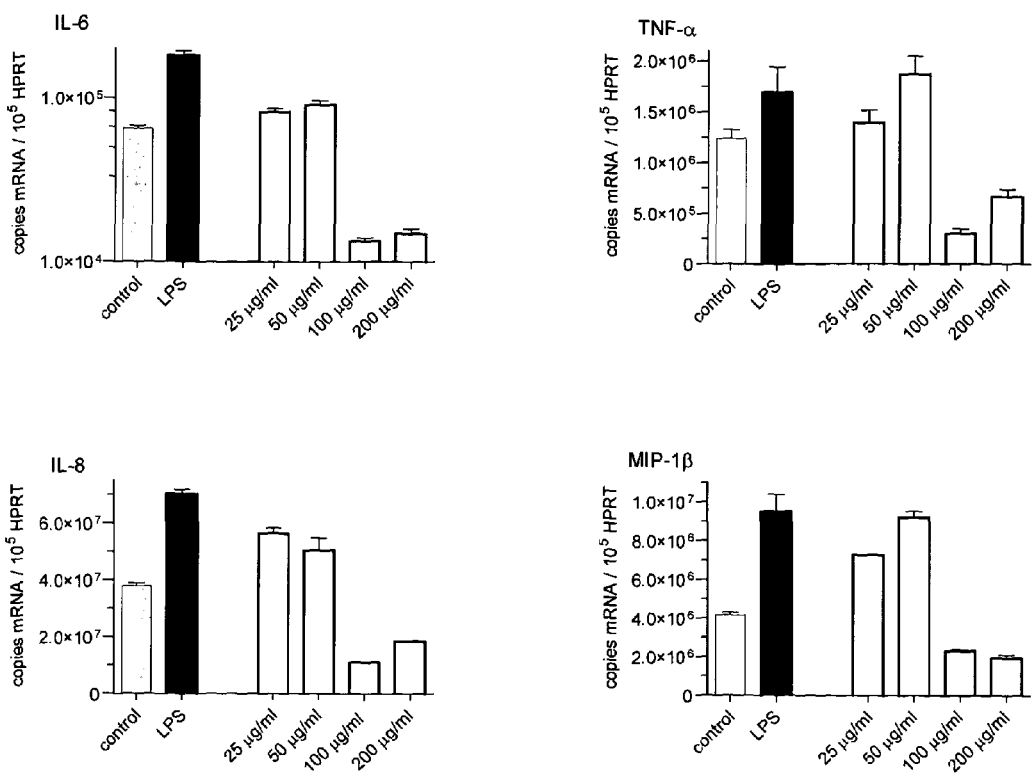

FIG. 38: The biological effect of generation 3 polypropyletherimine anionic carboxylic acid terminated dendrimer glucosamine was determined in 24 well plates using $10^6$ human monocytes pretreated with 25 to 200 µg/ml endotoxin free dendrimer glucosamine for 1 h followed by challenge with 25 ng/ml *Shigella* waaL LPS. After 3 h, RNA was extracted and real-time RT PCR performed. When compared with the LPS control, generation 3 polypropyletherimine anionic carboxylic acid terminated dendrimer glucosamine lead to the following reductions in pro-inflammatory cytokines:—a 12-fold reduction in IL-6, a 3-fold reduction in TNF-alpha, a 4-fold reduction in IL-8, and a 5-fold reduction in MIP-1 beta at 200 µg/ml. In contrast, there was no change in the anti-inflammatory cytokines IL-10 and interferon-beta.

FIG. 39: The biological effect of generation 3 polypropyletherimine anionic carboxylic acid terminated dendrimer glucosamine was determined in 24 well plates using $10^6$ human monocytes pretreated with 12.5 to 100 µg/ml endotoxin free dendrimer glucosamine for 1 h followed by challenge with:—(1) 25 ng/ml *Salmonella* LPS; (2) live *E. coli* bacteria (multiplicity of infection (MOI)=10); (3) live *Pseudomonas aeruginosa* bacteria (MOI=10); (4) live *Klebsiella pneumonia* bacteria (MOI=10); (5) live *S. aureus* bacteria (MOI=10); (6) live *E. faecalis* bacteria (MOI=10). After a 1 h incubation, gentamycin (100 µg/ml) was added to the monocyte cultures containing bacteria and the incubation was then continued for another 2 h, making a total of a 3 hour incubation. The RNA was then extracted and real-time RT PCR performed. In the case of every single stimulant used, generation 3 polypropyletherimine anionic carboxylic acid terminated dendrimer glucosamine lead to a significant reduction in the pro-inflammatory cytokines IL-6, TNF-alpha, and IL-8.

This figure summarises the results for IL-6. They show the following reductions:—(1) *Salmonella* LPS—a 925-fold reduction at 100 µg/ml; (2) live *E. coli* bacteria—a 30-fold reduction at 100 µg/ml; (3) live *Pseudomonas aerugenosa* bacteria—a 23-fold reduction at 100 µg/ml; (4) live *Klebsiella pneumonia* bacteria—a 48-fold reduction at 200 µg/ml; (5) live *S. aureus* bacteria—a 17-fold reduction at 100 µg/ml; (6) live *E. faecalis* bacteria—a 60-fold reduction at 200 µg/ml.

Figure 40:
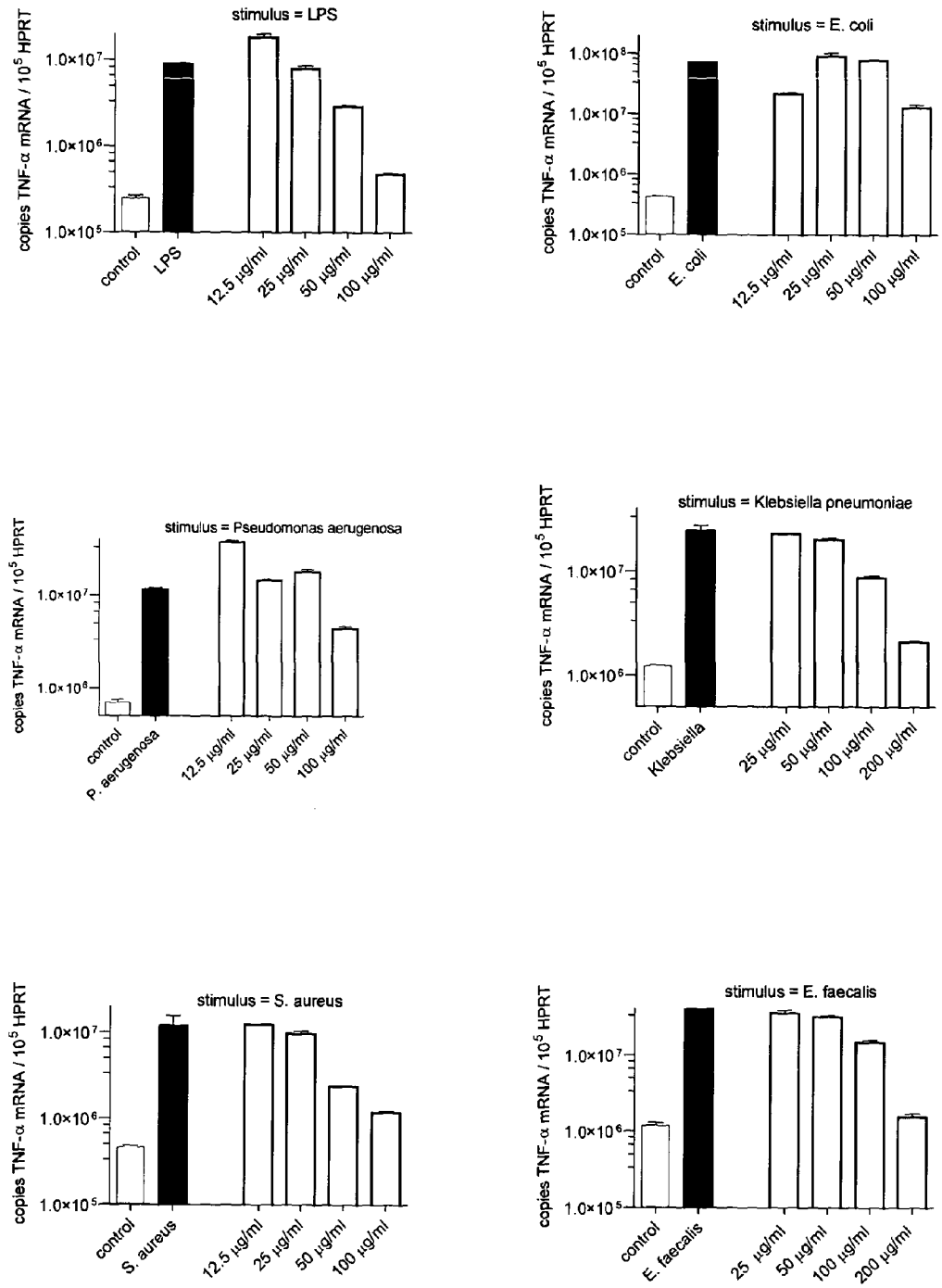

FIG. 40: The biological effect of generation 3 polypropyletherimine anionic carboxylic acid terminated dendrimer glucosamine was determined in 24 well plates using $10^6$ human monocytes pretreated with 12.5 to 100 µg/ml endotoxin free dendrimer glucosamine for 1 h followed by challenge with:—(1) 25 ng/ml *Salmonella* LPS; (2) live *E. coli* bacteria (multiplicity of infection (MOI)=10); (3) live *Pseudomonas aeruginosa* bacteria (MOI=10); (4) live *Klebsiella pneumonia* bacteria (MOI=10); (5) live *S. aureus* bacteria (MOI=10); (6) live *E. faecalis* bacteria (MOI=10). After a 1 h incubation, gentamycin (100 µg/ml) was added to the monocyte cultures containing bacteria and the incubation was then continued for another 2 h, making a total of a 3 hour incubation. The RNA was then extracted and real-time RT PCR performed. In the case of every single stimulant used, generation 3 polypropyletherimine anionic carboxylic acid terminated dendrimer glucosamine lead to a significant reduction in the pro-inflammatory cytokines IL-6, TNF-alpha, and IL-8.

This figure summarises the results for TNF-alpha. They show the following reductions:—(1) *Salmonella* LPS—an 20-fold reduction at 100 µg/ml; (2) live *E. coli* bacteria—a 6-fold reduction at 100 µg/ml; (3) live *Pseudomonas aeruginosa* bacteria—a 3-fold reduction at 100 µg/ml; (4) live *Klebsiella pneumonia* bacteria—a 12-fold reduction at 200 µg/ml; (5) live *S. aureus* bacteria—a 10-fold reduction at 100 µg/ml; (6) live *E. faecalis* bacteria—a 45-fold reduction at 200 µg/ml.

Figure 41:
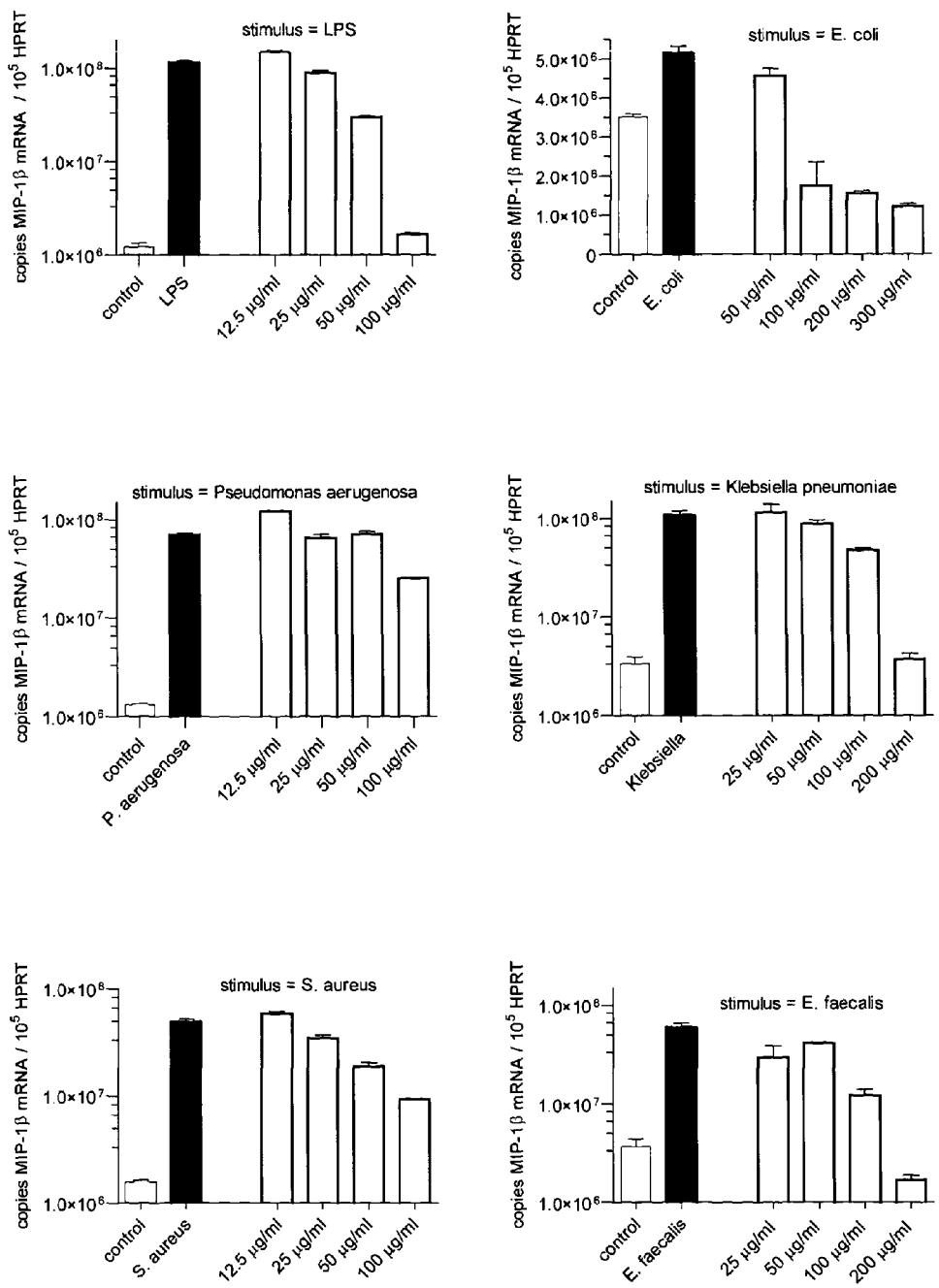

FIG. 41: The biological effect of generation 3 polypropyletherimine anionic carboxylic acid terminated dendrimer glucosamine was determined in 24 well plates using $10^6$ human monocytes pretreated with 12.5 to 100 µg/ml endotoxin free dendrimer glucosamine for 1 h followed by challenge with:—(1) 25 ng/ml *Salmonella* LPS; (2) live *E.* coli bacteria (multiplicity of infection (MOI)=10); (3) live *Pseudomonas aeruginosa* bacteria (MOI=10); (4) live *Klebsiella pneumonia* bacteria (MOI=10); (5) live *S. aureus* bacteria (MOI=10); (6) live *E. faecalis* bacteria (MOI=10). After a 1 h incubation, gentamycin (100 μg/ml) was added to the monocyte cultures containing bacteria and the incubation was then continued for another 2 h, making a total of a 3 hour incubation. The RNA was then extracted and real-time RT PCR performed. In the case of every single stimulant used, generation 3 polypropyletherimine anionic carboxylic acid terminated dendrimer glucosamine lead to a significant reduction in the pro-inflammatory cytokines IL-6, TNF-alpha, and IL-8.

This figure summarises the results for MIP-1 beta. They show the following reductions:—(1) *Salmonella* LPS—a 70-fold reduction at 100 μg/ml; (2) live *E. coli* bacteria—a 5-fold reduction at 300 μg/ml; (3) live *Pseudomonas* aerugenosa bacteria—a 3-fold reduction at 100 μg/ml; (4) live *Klebsiella pneumonia* bacteria—a 30-fold reduction at 200 μg/ml; (5) live *S. aureus* bacteria—a 5-fold reduction at 100 μg/ml; (6) live *E. faecalis* bacteria—a 35-fold reduction at 200 μg/ml.

FIG. 42: Shows the 1-D H-NMR spectrum for the polypropyletherimine core with 16-COOH's FIG. 43: Shows the 2-D H-COSY spectrum for the polypropyletherimine core with 16-COOH's.

FIG. 44: Shows the $^{13}$C-NMR spectrum for the polypropyletherimine core with 16-COOH's.

FIG. 45: Shows the Distortionless Enhancement by Polarization Transfer 135 $^{13}$CNMR spectrum for the polypropyletherimine core with 16 terminal carboxylic acids.

FIG. 46: Shows the MALDI mass spectrum for the polypropyletherimine core with 16-COOH's.

Figure 47:
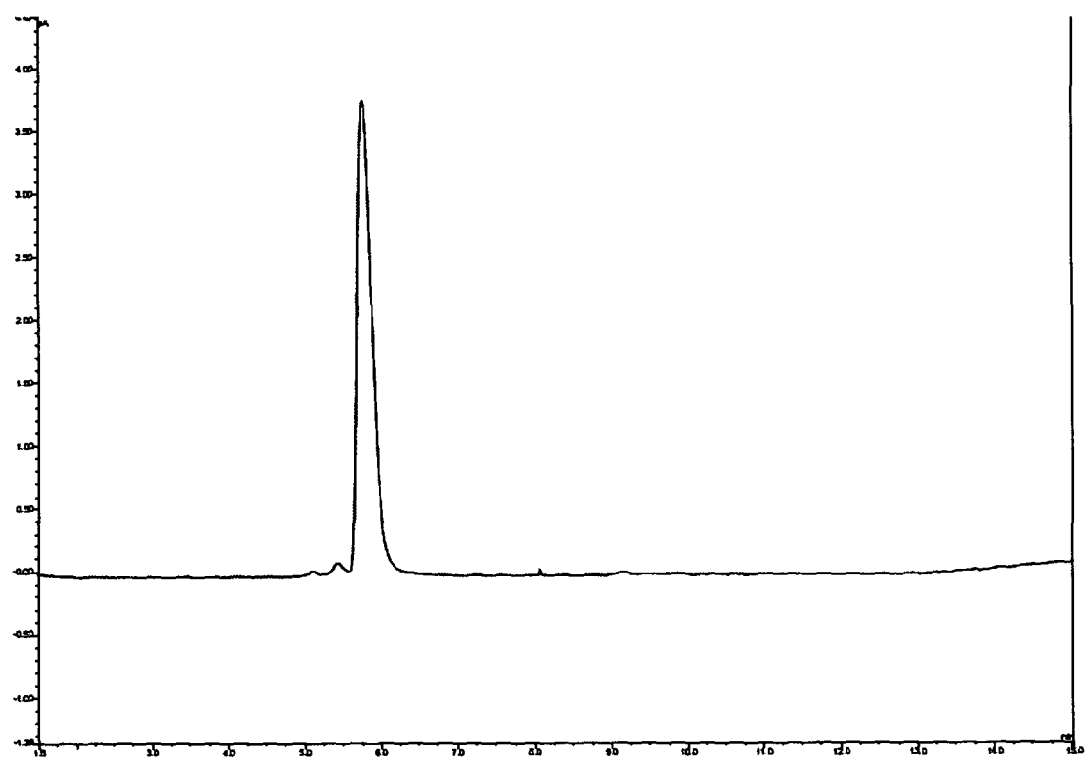

FIG. 47: Shows the HPLC charged aerosol detection trace for the polypropyletherimine core with 16-COOH terminal carboxylic acids.

Figure 48:
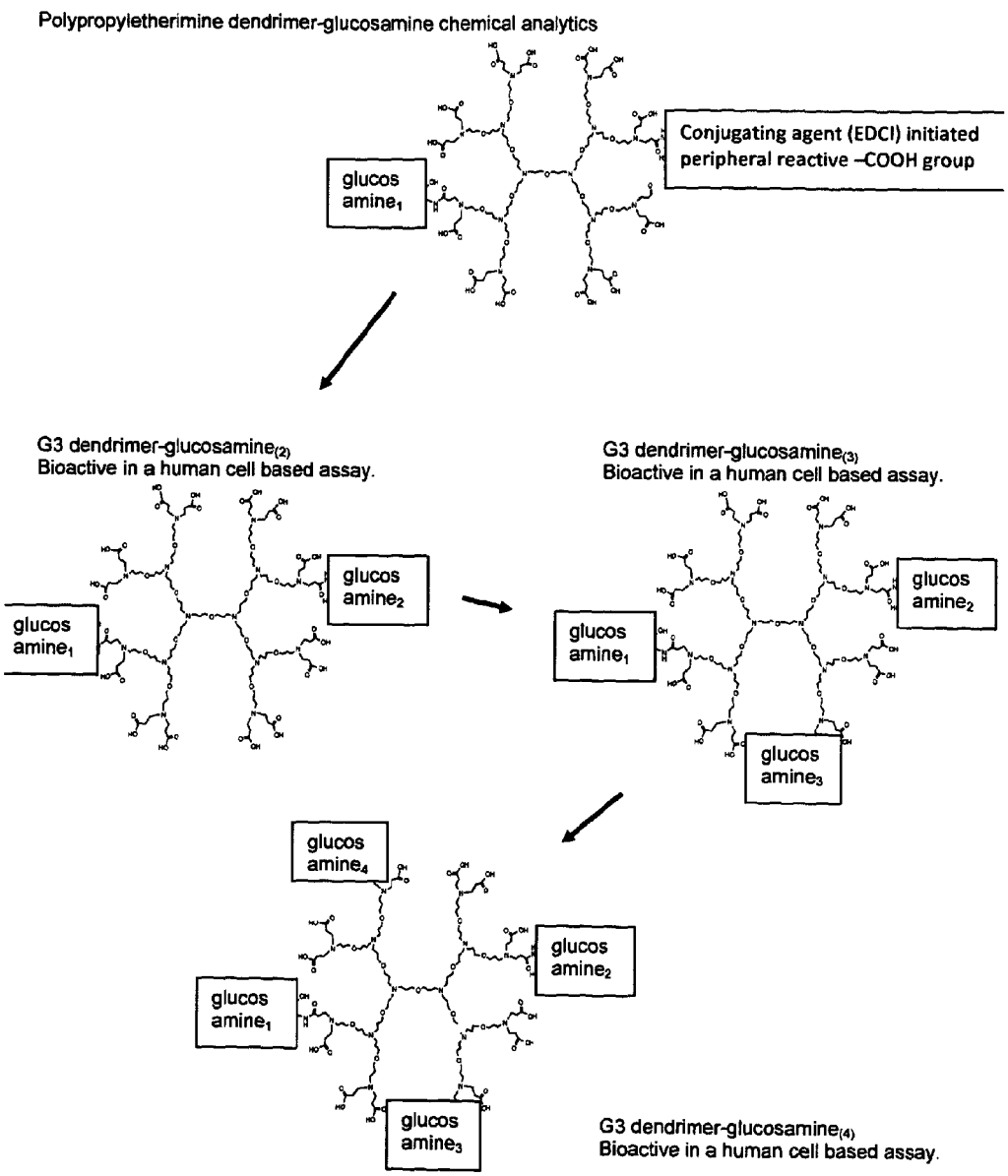
Figure 50:
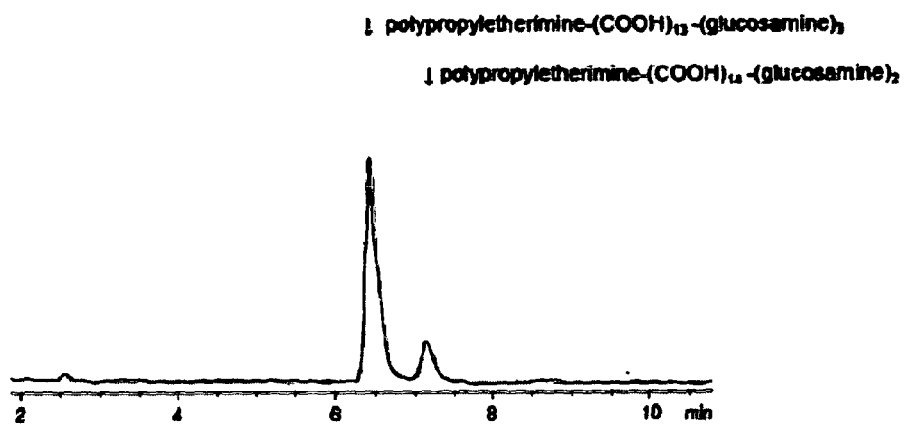
Figure 51:
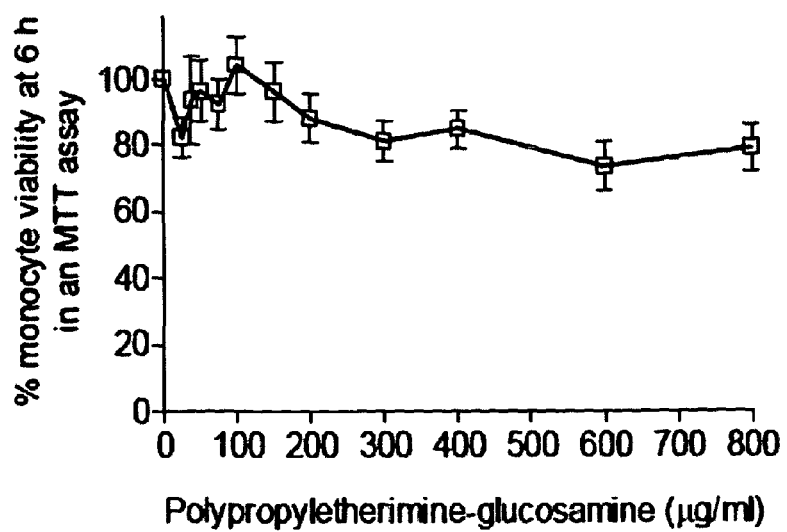

FIG. 48: Shows a diagrammatic representation of polypropyletherimine conjugation to glucosamine FIG. 49*a*: Shows the H-NMR spectrum for the G3 polypropyletherimine dendrimer glucosamine FIG. 49*b*: Shows the $^{13}$C-NMR spectrum for the G3 polypropyletherimine dendrimer glucosamine FIG. 50: Shows the HPLC-UV trace for the G3 polypropyletherimine dendrimer glucosamine FIG. 51: Show G3 polypropyletherimine glucosamine is not cytotoxic to primary human monocytes as determined using the MTT method (see Example 2A for method details).

FIG. 52: Shows that high purity (95%) G3 polypropyletherimine glucosamine was bioactive at 50 μg/ml when tested using human monocytes and *shigella* LPS (see Example 2B for method details).

FIG. 53: Shows that high purity (95%) G3 polypropyletherimine glucosamine was bioactive at 100 μg/ml when tested using human monocytes & *E. coli* bacteria (see Example 2D for method details).

FIG. 54: Shows that G3 polypropyletherimine glucosamine remained bioactive at 100 μg/ml after storage at 37° C. & 100% humidity in a sealed vial (under argon and moisture free) for 42 days when tested using human monocytes and *salmonella* LPS (see Example 2D for method details).

FIG. 55: Shows that G3 polypropyletherimine glucosamine does not have antimicrobial properties.

FIG. 56 Shows the biological effect of G3 polypropyletherimine dendrimer glucosamine 6-sulfate was determined in 24 well plates using $10^6$ human monocytes pretreated with 50 to 150 μg/ml endotoxin free dendrimer glucosamine 6-sulfate for 1 h followed by challenge with 25 ng/ml *Salmonella* LPS. After 3 h, RNA was extracted and real-time RT PCR performed. When compared with the LPS control, generation 3 polypropyletherimine dendrimer glucosamine 6-sulfate did not lead to a reduction in the pro-inflammatory cytokine TNF-alpha or the pro-inflammatory chemokine MIP-1 beta.

The invention claimed is:

1. A glycodendrimer comprising:
    a) a non-toxic generation 3 dendrimer polypropyletherimine core supporting 16 terminal carboxylic acid groups, wherein the dendrimer polypropyletherimine core has a central atom which is oxygen, and
    b) conjugated to said core 2, 3, 4 or 5 glucosamine molecures, wherein each glucosamine molecule is linked directly through a zero length amide bond with a residue of a terminal carboxylic acid group.

2. The glycodendrimer according to claim 1 wherein 2, 3, or 4 glucosamine molecules are conjugated to said core.

3. A population of glycodendrimers wherein the average properties of the population are as defined in claim 1.

4. A pharmaceutical formulation comprising (a) the glycodendrimer as defined in claim 1 or (b) population of glycodendrimers, wherein the average properties of the population are as defined in claim 1 and a pharmaceutically acceptable excipient.

5. The pharmaceutical formulation according to claim 4, which is formulated for topical administration, for infusion or direct injection, or for oral administration.

6. The pharmaceutical formulation according to claim 4, wherein one dose contains in range of 10 μg to 1 g of (a) glycodendrimer or (b) the population of glycodendrimers.

7. A method of treating an inflammatory response mediated by increased levels of one or more cytokines selected from the group consisting of IL-6, TNF-α, IL-8, IL-1 β, and MIP-1 α and β, wherein the inflammatory response is caused by infection of a bacterium selected from the group consisting of *Escherichia coli, Klebsiella aeruginosa, Staphylococcus aureus, Escherichia faecalis, Pseudomonas aeruginosa, Shigella* sp., *Salmonella* sp, *Campylobacter* sp., and *Clostridium difficile*, comprising administering to a patient in need thereof a therapeutically effective amount of the glycodendrimer according to claim 1, a population of glycodendrimers wherein the average properties of the population are as defined in claim 1, or a pharmaceutical formulation comprising the glycodendrimer or the population.

8. The method according to claim 7, wherein the infection causes diarrhoea.

9. The method according to claim 7, wherein the infection is caused by *Escherichia coli, Klebsiella aeruginosa, Staphylococcus aureus, Escherichia faecalis,* and/or *Pseudomonas aeruginosa.*

10. The method according to claim 7, wherein the infection is caused by *Shigella* sp., *Salmonella* sp, *Campylobacter* sp., and/or *Clostridium difficile.*

11. A method of treating a pro-inflammatory cytokine response caused by inflammatory bowel disease, comprising administering to a patient in need thereof a therapeutically effective amount of the glycodendrimer according to claim 1, a population of glycodendrimers wherein the average properties of the population are as defined in claim 1, or a pharmaceutical formulation comprising the glycodendrimer or the population.

12. The method according to claim 11, wherein the inflammatory bowel disease involves an excessive stimulation of Toll Like receptors by gut bacteria.

* * * * *